United States Patent
Tang et al.

(10) Patent No.: US 9,566,277 B2
(45) Date of Patent: Feb. 14, 2017

(54) METHODS OF USING PHTHALAZINONE KETONE DERIVATIVES

(71) Applicant: Jiangsu Hansoh Pharmaceutical Co., Ltd., Lianyungang, Jiangsu (CN)

(72) Inventors: Peng Cho Tang, Shanghai (CN); Xin Li, Shanghai (CN); Xiangqin Li, Shanghai (CN); Yang Chen, Shanghai (CN); Bin Wang, Shanghai (CN); Zhe Zhu, Shanghai (CN)

(73) Assignee: Jiangsu Hansoh Pharmaceutical Co., Ltd., Lianyungang, Jiangsu (CN)

( * ) Notice: Subject to any disclaimer, the term of this patent is extended or adjusted under 35 U.S.C. 154(b) by 0 days.

(21) Appl. No.: 15/016,986

(22) Filed: Feb. 5, 2016

(65) Prior Publication Data

US 2016/0151367 A1 Jun. 2, 2016

Related U.S. Application Data

(62) Division of application No. 13/811,957, filed as application No. PCT/CN2011/001223 on Jul. 26, 2011, now Pat. No. 9,273,052.

(30) Foreign Application Priority Data

Aug. 9, 2010 (CN) .......................... 2010 1 0248307

(51) Int. Cl.
| | | |
|---|---|---|
| A61K 31/502 | (2006.01) | |
| C07D 487/04 | (2006.01) | |
| A61K 45/00 | (2006.01) | |
| A61K 31/4188 | (2006.01) | |
| A61K 31/495 | (2006.01) | |
| A61K 31/5377 | (2006.01) | |

(52) U.S. Cl.
CPC ......... *A61K 31/502* (2013.01); *A61K 31/4188* (2013.01); *A61K 31/495* (2013.01); *A61K 31/5377* (2013.01); *A61K 45/00* (2013.01); *C07D 487/04* (2013.01)

(58) Field of Classification Search
None
See application file for complete search history.

(56) References Cited

U.S. PATENT DOCUMENTS

| | | |
|---|---|---|
| 7,981,889 B2 | 7/2011 | Barr Martin et al. |
| 8,188,084 B2 | 5/2012 | Jones et al. |
| 8,207,161 B2 | 6/2012 | Tang et al. |
| 2008/0161280 A1 | 7/2008 | Gandhi et al. |

FOREIGN PATENT DOCUMENTS

| | | |
|---|---|---|
| CN | 1788000 A | 6/2006 |
| CN | 101501006 A | 8/2009 |
| CN | 101641014 A | 2/2010 |
| WO | 0236576 A1 | 5/2002 |
| WO | 2004080958 A2 | 9/2004 |
| WO | 2004080976 A1 | 9/2004 |
| WO | 2006021801 A1 | 3/2006 |
| WO | 2009025784 A1 | 2/2009 |
| WO | 2009082881 A1 | 7/2009 |
| WO | 2009090055 A1 | 7/2009 |

OTHER PUBLICATIONS

Benafif et al (OncoTargets and Therapy 8:519-528, 2015).*
Int'l Search Report issued Oct. 27, 2011 in Int'l Application No. PCT/CN2011/001223.
D'Amours et al, "Poly(ADP-ribosyl)ation reactions in the regulation of nuclear functions", Biochemical Journal, vol. 342, pp. 249-268 (1999).
Plummer, "Inhibition of poly(ADP-ribose) polymerase in cancer", Current Opinion in Parmacology, vol. 6, pp. 364-368 (2006).
Ratnam et al, "Current Development of Clinical Inhibitors of Poly(ADP-Ribose) Polymerase in Oncology", Clinical Cancer Research, vol. 13, pp. 1383-1388 (2007).
Tentori et al, "Potential Clinical Application of Poly(ADP-Ribose) Polymerase (PARP) Inhibitors", Pharmacological Research, vol. 45, No. 2, pp. 73-85 (2002).
Horvath et al, "Poly(ADP-ribose) Polymerase as a Drug Target for Cardiovascular Disease and Cancer: An Update", Drug News Perspectives, vol. 20, No. 3, pp. 171-181 (Apr. 2007).
Faro et al, "Myocardial Protection by PJ34, a Novel Potent Poly (ADP-Ribose) Synthetase Inhibitor", The Annals of Thoracic Surgery, vol. 73, pp. 575-581 (2002).
Kumaran et al, "Benzamide protects delayed neuronal death and behavioural impairment in a mouse model of global cerebral ischemia", Behavioural Brain Research, vol. 192, pp. 178-184 (2008).
Kim et al, "(2R)-4-Oxo-4-3[-(Trifluoromethyl)-5,6-dihydro[1,2,4]triazolo[4,3-alpha]pyrazin-7(8H)-yl]-1-(2,4,5-trifluorophenyl)butan-2-amine: A Potent, Orally Active Dipeptidyl Peptidase IV Inhibitor for the Treatment of Type 2 Diabetes", Journal of Medicinal Chemistry, vol. 48, pp. 141-151 (2005).
Anderson (Chem and Biol 10:787-797, 2003).
Thiel (Nature Biotechnol 2:513-519, 2004).

* cited by examiner

Primary Examiner — Craig Ricci
(74) Attorney, Agent, or Firm — Panitch Schwarze Belisario & Nadel LLP

(57) ABSTRACT

A phthalazinone ketone derivative as represented by formula (I), a preparation method thereof, a pharmaceutical composition containing the derivative, a use thereof as a poly (ADP-ribose) polymerase (PARP) inhibitor, and a cancer treatment method thereof are described.

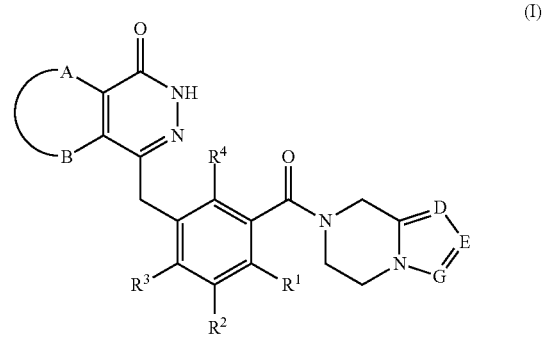

18 Claims, No Drawings

METHODS OF USING PHTHALAZINONE KETONE DERIVATIVES

CROSS-REFERENCE TO RELATED APPLICATIONS

This application is a divisional of U.S. application Ser. No. 13/811,957, filed Jan. 24, 2013, which is a Section 371 of International Application No. PCT/CN2011/001223, filed on Jul. 26, 2011, which was published in the Chinese language on Feb. 16, 2012, under International Publication No. WO 2012/019427 A1, and the disclosures of which are incorporated herein by reference.

FIELD OF THE INVENTION

The present invention relates to a novel phthalazinone ketone derivative as represented by formula (I), the preparation methods thereof, the pharmaceutical composition containing the derivative, and the use thereof as a therapeutic agent, especially as the poly (ADP-ribose) polymerase (PARP) inhibitor.

BACKGROUND OF THE INVENTION

Chemotherapy and radiation therapy are two common methods to treat cancer. Both treatments can induce single-stranded and/or double-stranded DNA breakage to produce cytotoxicity, then the targeted tumor cells will die due to chromosomal damage. An important result in response to DNA damage signal is that the signal of the cell cycle in regulation site is activated, the purpose of which is to protect cells from mitosis in the case of DNA damage thereby preventing cell damage. In most cases, the tumor cells exhibit the defects of regulation signal in the cell cycle and have high proliferation rate. So it can be predicted that the tumor cells have specific DNA repair mechanisms, which can respond quickly to repair chromosome damage relevant to proliferation regulation, thereby saving them from cytotoxic effects of some treatment and keep alive.

In the clinical application, the effective concentration of the chemotherapeutical drug or therapeutic radiation intensity can fight these DNA repair mechanism to ensure the killing effect on the target tumor cells. However, the tumor cells can develop tolerance for treatment by enhancing its DNA damage repair mechanisms, and survive from the lethal DNA damage. In order to overcome the tolerance, it is usually necessary to increase the dosage of the therapeutic drug or radiation intensity. This approach will produce adverse effects on the normal tissue nearby the lesions, and then make the treatment course complicated by severe adverse reactions, thereby increasing the risk of treatment. At the same time, the ever-increasing tolerance will reduce the therapeutic effect, so it can be concluded that the cytotoxicity of the DNA damage agents can be improved in the way of tumor cell-specificity by controlling the repair mechanism promoted by the signal of DNA damage.

PARPs (Poly (ADP-ribose) polymerases), characterized by poly ADP-ribosylation activity, are constituted by the superfamily of 18 nucleus enzymes and cytoplasmic enzymes. Such poly ADP-ribosylation effect can adjust the activity of the targeted protein and the interaction between proteins, and regulate other many fundamental biological processes, including DNA repair and cell death. In addition, genomic stability is also associated with the poly ADP-ribosylation (see D'Amours et al. *Biochem. J*, 1999, 342, 249).

The activity of PARP-1 accounts for about 80% of the total cellular PARP activity. PARP-1, together with PARP-2, which is most similar to PARP-1, are the members having the DNA damage repair capacity in the PARP family. As a sensor and a signaling protein of DNA damage, PARP-1 can detect the DNA damage sites quickly and bond to them directly, and then induce the aggregation of various proteins required for DNA repair, thereby enabling the DNA damage to be repaired. When the cells lack PARP-1, PARP-2 can realize the repair of the DNA damage instead of PARP-1.

Studies have shown that, compared with normal cells, the expression of PARPs protein in solid tumors is generally enhanced. In addition, the tumors (such as breast cancer and ovarian cancer), whose DNA repair related gene is missing (such as BRCA-1 or BRCA-2), show extreme sensitivity to PARP-1 inhibitors. This suggests the potential uses of PARP inhibitors as a single agent in the treatment of a tumor, which can be called triple negative breast cancer (see Plummer, E. R. *Curr. Opin. Pharmacol.* 2006, 6, 364; Ratnam, et al; *Clin. Cancer Res.* 2007, 13, 1383). At the same time, because DNA damage repair mechanism is the main mechanism of tumor cells response to the tolerance produced by chemotherapeutic drugs and ionizing radiation treatment, PARP-1 is considered to be an effective target to explore the new methods of cancer therapy.

PARP inhibitors were initially developed and designed using nicotinamide of $NAD^+$, which can be used as PARP catalytic substrate, as a template to develop its analogs. As competitive inhibitors of $NAD^+$, these inhibitors compete with $NAD^+$ for PARP catalytic sites, thereby preventing the synthesis of the poly (ADP-ribose) chain. PARP without poly (ADP-ribosylation) modification cannot be dissociated from the DNA damage sites, which will lead other proteins involved in the repair into the damage site, thereby preventing performance of the repair process. Therefore, in the effect of the cytotoxic drugs or radiation, PARP inhibitor will eventually kill tumor cells with DNA damage.

In addition, the $NAD^+$, which is consumed as the PARP catalytic substrate, is the essential factor in the ATP synthesis process of the cells. Under the high level of PARP activity, intracellular $NAD^+$ levels will significantly decrease, thereby affecting the intracellular ATP level. Due to lack of intracellular ATP content, the cells cannot achieve programmed ATP-dependent cell death process, and can only turn to necrosis, a special apoptosis process. During the necrosis, a lot of inflammatory cytokines will be released, thereby producing toxic effects on other organs and tissues (Horvath E M et al. *Drug News Perspect,* 2007, 20, 171-181). Therefore, PARP inhibitors can also be used for the treatment of a variety of diseases related to this mechanism, including neurodegenerative diseases (such as Alzheimer's disease, Huntington's disease, Parkinson's disease), diabetes, concurrent diseases in the ischemia or ischemia-reperfusion process, such as myocardial infarction and acute renal failure, circulatory system diseases, such as septic shock and inflammatory diseases, such as chronic rheumatism, etc (see Tentori L, et al. *Pharmacol. Res.,* 2002, 45, 73-85; Horvath E M et al. *Drug News Perspect.,* 2007, 20, 171; Faro R, et al. *Ann. Thorac. Surg.,* 2002, 73, 575; Kumaran D, et al. *Brain Res.,* 2008, 192, 178).

Currently, a series of patent application have been disclosed on phthalazinone ketone PARP inhibitor, including WO2002036576, WO2004080976 and WO2006021801.

Although there are a series of PARP inhibitors for tumor treatment that have been disclosed, there remains a need to develop new compounds with better efficacy and pharmacokinetics results. After continuous efforts, the present invention designs a series of compounds of formula (I), and finds that the compounds having such structure exhibit an excellent effect and function.

SUMMARY OF THE INVENTION

The present invention is directed to a phthalazinone ketone derivative of formula (I) or a tautomer, enantiomer, diastereomer, racemate, or pharmaceutically acceptable salt thereof, as well as a metabolite, metabolic precursor or prodrug thereof:

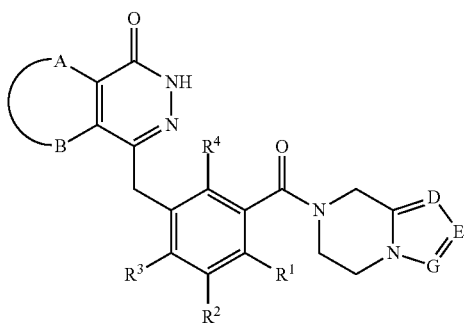

(I)

wherein:

A and B are taken together with the attached carbon atoms to form a cycloalkyl, heterocyclyl, aryl or heteroaryl, wherein said cycloalkyl, heterocyclyl, aryl or heteroaryl is each independently and optionally substituted with one or more groups selected from the group consisting of alkyl, halogen, hydroxyl, alkoxyl, cycloalkyl, heterocyclyl, aryl, heteroaryl, —C(O)OR$^5$, —OC(O)R$^5$, —O(CH$_2$)$_n$C(O)OR$^5$, —C(O)R$^5$, —NHC(O)R$^5$, —NR$^6$R$^7$, —OC(O)NR$^6$R$^7$ and —C(O)NR$^6$R$^7$;

R$^1$, R$^2$, R$^3$ or R$^4$ is each independently selected from the group consisting of hydrogen, halogen, alkyl, cyano and alkoxyl, wherein said alkyl or alkoxyl is each independently and optionally substituted with one or more groups selected from the group consisting of halogen, hydroxyl, alkyl and alkoxyl;

D, E, or G is each independently selected from the group consisting of nitrogen atom and C(R$^8$);

R$^5$ is selected from the group consisting of hydrogen, alkyl, cycloalkyl, heterocyclyl, aryl and heteroaryl, wherein said alkyl, cycloalkyl, heterocyclyl, aryl or heteroaryl is each independently and optionally substituted with one or more groups selected from the group consisting of alkyl, halogen, hydroxyl, alkoxyl, cycloalkyl, heterocyclyl, aryl, heteroaryl, carboxyl and alkoxycarbonyl;

R$^6$ or R$^7$ is each independently selected from the group consisting of hydrogen, alkyl, cycloalkyl, heterocyclyl, aryl and heteroaryl, wherein said alkyl, cycloalkyl, heterocyclyl, aryl or heteroaryl is each independently and optionally substituted with one or more groups selected from the group consisting of alkyl, halogen, hydroxyl, alkoxyl, cycloalkyl, heterocyclyl, aryl, heteroaryl, carboxyl and alkoxycarbonyl;

or, R$^6$ and R$^7$ are taken together with the attached N atom to form heterocyclyl, wherein said heterocyclyl contains one or more N, O or S(O)$_m$ heteroatoms, and said heterocyclyl is optionally substituted with one or more groups selected from the group consisting of alkyl, halogen, hydroxyl, alkoxyl, cycloalkyl, heterocyclyl, aryl, heteroaryl, carboxyl and alkoxycarbonyl;

R$^8$ is selected from the group consisting of hydrogen, alkyl, halogen, hydroxyl, cyano, alkoxyl, cycloalkyl, heterocyclyl, aryl, heteroaryl, benzyl, —C(O)OR$^5$, —OC(O)R$^5$, —O(CH$_2$)$_n$C(O)OR$^5$, —(CH$_2$)$_n$NR$^6$R$^7$, —C(O)R$^5$, —NHC(O)R$^5$, —NR$^6$R$^7$, —OC(O)NR$^6$R$^7$ and —C(O)NR$^6$R$^7$, wherein said alkyl, alkoxyl, cycloalkyl, heterocyclyl, aryl, heteroaryl or benzyl is each independently and optionally substituted with one or more groups selected from the group consisting of alkyl, halogen, hydroxyl, alkoxyl, cycloalkyl, heterocyclyl, aryl, heteroaryl, oxo, —C(O)OR$^5$, —OC(O)R$^5$, —O(CH$_2$)$_n$C(O)OR$^5$, —C(O)R$^5$, —NHC(O)R$^5$, —NR$^6$R$^7$, —OC(O)NR$^6$R$^7$ and —C(O)NR$^6$R$^7$;

m is selected from the group consisting of 0, 1 and 2; and
n is selected from the group consisting of 0, 1 and 2.

A preferable embodiment of the invention relates to a compound of formula (I) or its pharmaceutically acceptable salt, wherein A and B are taken together with the attached carbon atoms to form an aryl, preferably said aryl is phenyl.

Preferably, in the compound of formula (I) or its pharmaceutically acceptable salt, R$^1$ is hydrogen.

Preferably, in the compound of formula (I) or its pharmaceutically acceptable salt, R$^1$ is halogen, preferably fluorine atom.

Preferably, in the compound of formula (I) or its pharmaceutically acceptable salt, R$^1$ is halogen, preferably fluorine atom.

Preferably, in the compound of formula (I) or its pharmaceutically acceptable salt, R$^1$, R$^2$, R$^3$ or R$^4$ is each independently selected from hydrogen atom.

Preferably, in the compound of formula (I) or its pharmaceutically acceptable salt, R$^8$ is selected from the group consisting of hydrogen, alkyl, halogen, cyano, —C(O)OR$^5$, —(CH$_2$)$_n$NR$^6$R$^7$ and —C(O)NR$^6$R$^7$, wherein said alkyl is optionally substituted with one or more halogen atoms.

Preferably, in the compound of formula (I) or its pharmaceutically acceptable salt, R$^8$ is trifluoromethyl.

The compound of formula (I) may contain asymmetric carbon atoms, therefore it can exist in the form of optically pure diastereomer, diastereomeric mixture, diastereomeric racemate, a mixture of diastereomeric racemate or as a meso-compound. The present invention includes all these forms. Diastereomeric mixture, diastereomeric racemate or the mixture of diastereomeric racemate can be isolated by conventional methods, such as column chromatography, thin layer chromatography and high performance liquid chromatography.

The equivalent can be understood by an ordinary person skilled in the art that the compound of formula (I) may also have tautomers. The tautomeric forms of the compound (I) include, but are not limited to, the structure represented by the following formula (II):

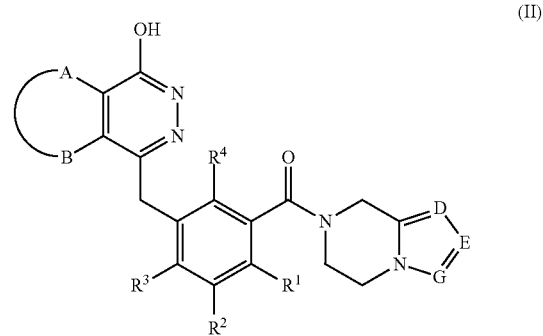

(II)

The compounds of the invention include, but are not limited to, the following:

| Example No. | Structure and Name |
|---|---|
| 1 | 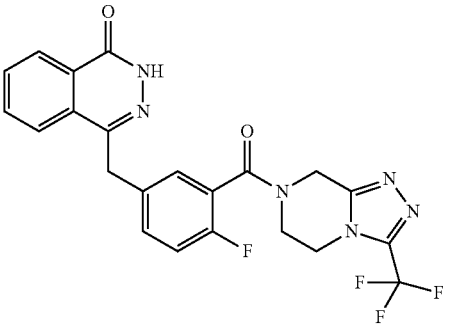 [SMILES: O=C(c1cc(Cc2n[nH]c(=O)c3ccccc23)ccc1F)N1CCn2c(nnc2C(F)(F)F)C1]4-[[4-fluoro-3-[3-(trifluoromethyl)-6,8-dihydro-5H-[1,2,4]triazolo[4,3-a]pyrazine-7-carbonyl]-phenyl]methyl]-2H-phthalazin-1-one |
| 2 | 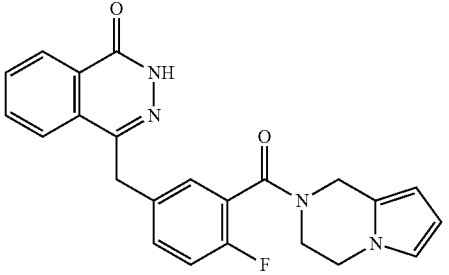 [SMILES: O=C(c1cc(Cc2n[nH]c(=O)c3ccccc23)ccc1F)N1CCn2cccc2C1]4-[[3-(3,4-dihydro-1H-pyrrolo[1,2-a]pyrazine-2-carbonyl)-4-fluoro-phenyl]methyl]-2H-phthalazin-1-one |
| 3 | 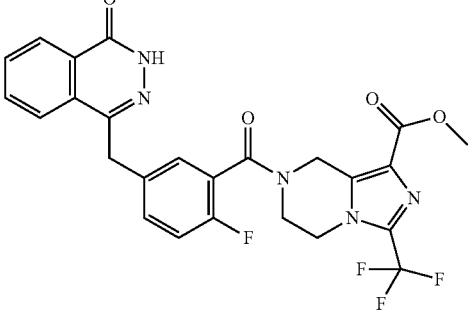methyl 7-[2-fluoro-5-[(4-oxo-3H-phthalazin-1-yl)methyl]benzoyl]-3-(trifluoromethyl)-6,8-dihydro-5H-imidazo[1,5-a]pyrazine-1-carboxylate |
| 4 | 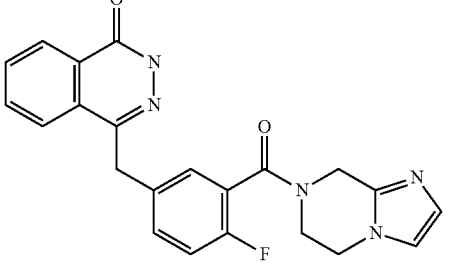4-[[3-(6,8-dihydro-5H-imidazo[1,2-a]pyrazine-7-carbonyl)-4-fluoro-phenyl]methyl]-2H-phthalazin-1-one |
| 5 | 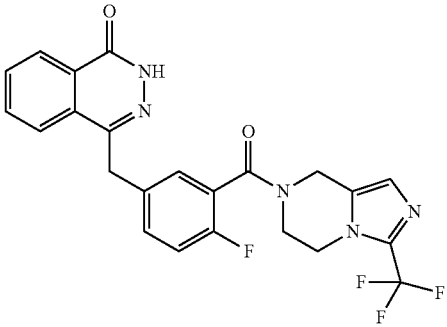 [SMILES: O=C(c1cc(Cc2n[nH]c(=O)c3ccccc23)ccc1F)N1CCn2c(cnc2C(F)(F)F)C1]4-[[4-fluoro-3-[3-(trifluoromethyl)-6,8-dihydro-5H-imidazo[1,5-a]pyrazine-7-carbonyl]phenyl]methyl]-2H-phthalazin-1-one |
| 6 | 4-[[4-fluoro-3-[1-(hydroxymethyl)-3-(trifluoromethyl)-6,8-dihydro-5H-imidazo[1,5-a]pyrazine-7-carbonyl]phenyl]methyl]-2H-phthalazin-1-one |
| 7 | 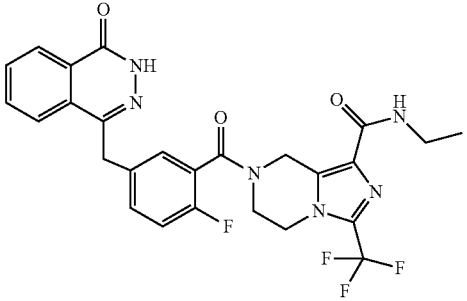 [SMILES: CCNC(=O)c1nc(C(F)(F)F)n2c1CN(C(=O)c1cc(Cc3n[nH]c(=O)c4ccccc34)ccc1F)CC2]N-ethyl-7-[2-fluoro-5-[(4-oxo-3H-phthalazin-1-yl)methyl]benzoyl]-3-(trifluoromethyl)-6,8-dihydro-5H-imidazo[1,5-a]pyrazine-1-carboxamide |

| Example No. | Structure and Name |
|---|---|
| 8 | 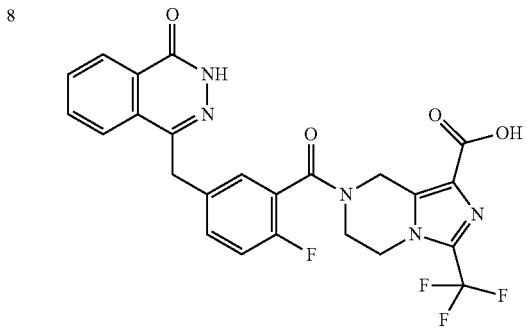
7-[2-fluoro-5-[(4-oxo-3H-phthalazin-1-yl)methyl]benzoyl]-3-(trifluoromethyl)-6,8-dihydro-5H-imidazo[1,5-a]pyrazine-1-carboxylic acid |
| 9 | 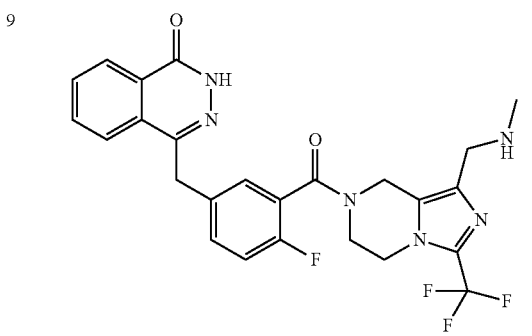
4-[[4-fluoro-3-[1-(methylaminomethyl)-3-(trifluoromethyl)-6,8-dihydro-5H-imidazo[1,5-a]pyrazine-7-carbonyl]phenyl]methyl]-2H-phthalazin-1-one |
| 10 | 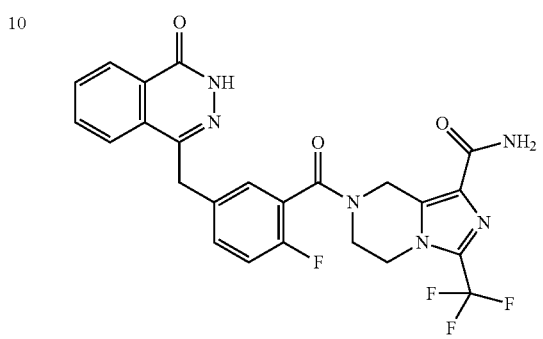
7-[2-fluoro-5-[(4-oxo-3H-phthalazin-1-yl)methyl]benzoyl]-3-(trifluoromethyl)-6,8-dihydro-5H-imidazo[1,5-a]pyrazine-1-carboxamide |

| Example No. | Structure and Name |
|---|---|
| 11 | 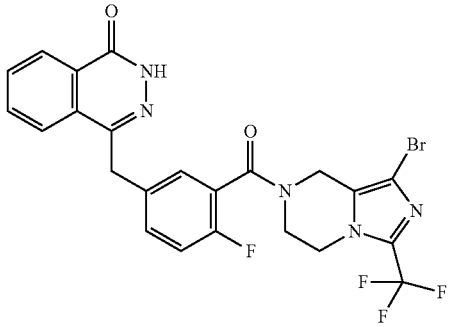 [SMILES: O=C(c1cc(Cc2n[nH]c(=O)c3ccccc23)ccc1F)N1CCn2c(C(F)(F)F)nc(Br)c2C1]
4-[[3-[1-bromo-3-(trifluoromethyl)-6,8-dihydro-5H-imidazo[1,5-a]pyrazine-7-carbonyl]-4-fluoro-phenyl]methyl]-2H-phthalazin-1-one |
| 12 | 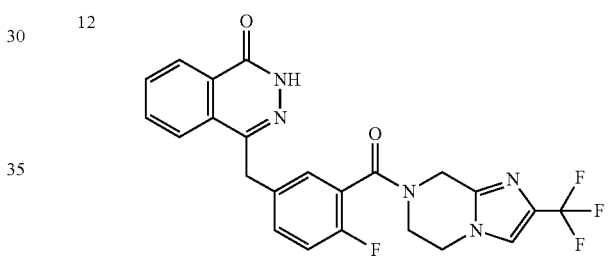
4-[[4-fluoro-3-[2-(trifluoromethyl)-6,8-dihydro-5H-imidazo[1,2-a]pyrazine-7-carbonyl]phenyl]methyl]-2H-phthalazin-1-one |
| 13 | 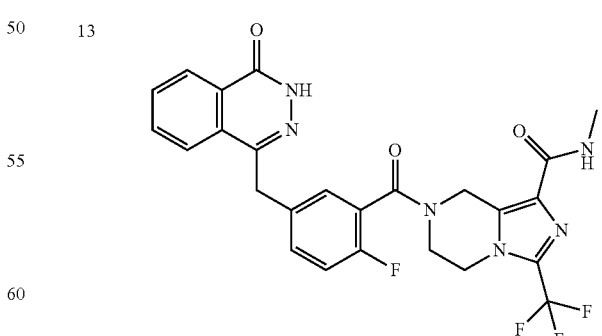
7-[2-fluoro-5-[(4-oxo-3H-phthalazin-1-yl)methyl]benzoyl]-N-methyl-3-(trifluoromethyl)-6,8-dihydro-5H-imidazo[1,5-a]pyrazine-1-carboxamide |

| Example No. | Structure and Name |
|---|---|
| 14 | 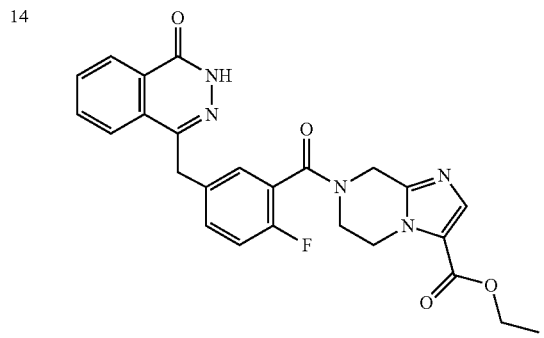<br>ethyl 7-[2-fluoro-5-[(4-oxo-3H-phthalazin-1-yl)methyl]benzoyl]-6,8-dihydro-5H-imidazo[1,2-a]pyrazine-3-carboxylate |
| 15 | 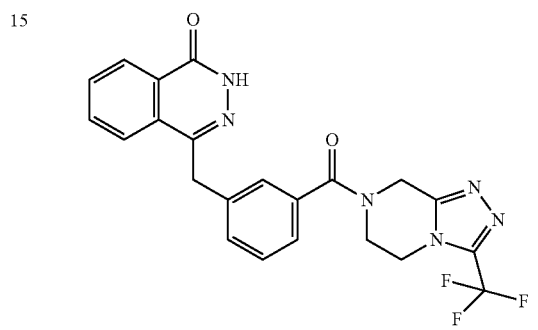<br>4-[[3-[3-(trifluoromethyl)-6,8-dihydro-5H-[1,2,4]triazolo[4,3-a]pyrazine-7-carbonyl]phenyl]methyl]-2H-phthalazin-1-one |
| 16 | 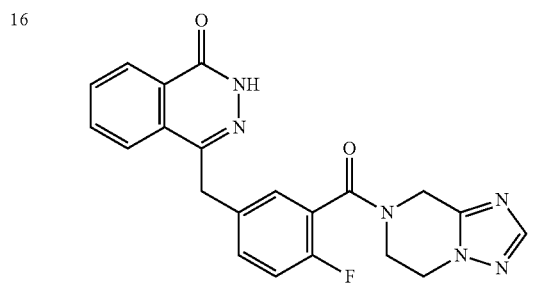<br>4-[[3-(6,8-dihydro-5H-[1,2,4]triazolo[1,5-a]pyrazine-7-carbonyl)-4-fluoro-phenyl]methyl]-2H-phthalazin-1-one |
| 17 | 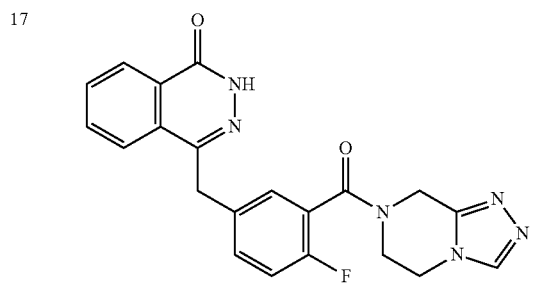<br>4-[[3-(6,8-dihydro-5H-[1,2,4]triazolo[4,3-a]pyrazine-7-carbonyl)-4-fluoro-phenyl]methyl]-2H-phthalazin-1-one |

| Example No. | Structure and Name |
|---|---|
| 18 | 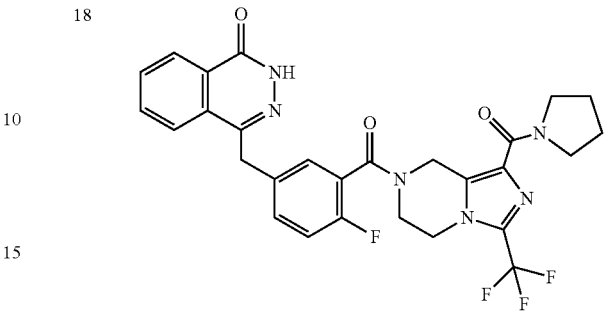<br>4-[[4-fluoro-3-[1-(pyrrolidine-1-carbonyl)-3-(trifluoromethyl)-6,8-dihydro-5H-imidazo[1,5-a]pyrazine-7-carbonyl]phenyl]methyl]-2H-phthalazin-1-one |
| 19 | 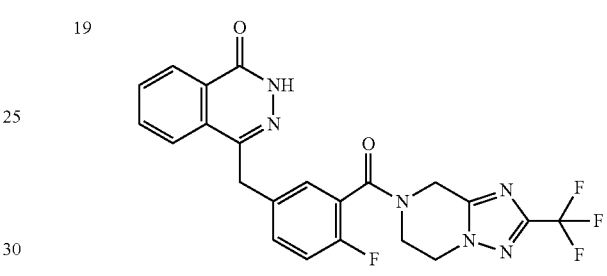<br>4-[[4-fluoro-3-[2-(trifluoromethyl)-6,8-dihydro-5H-[1,2,4]triazolo[1,5-a]pyrazine-7-carbonyl]phenyl]methyl]-2H-phthalazin-1-one |
| 20 | 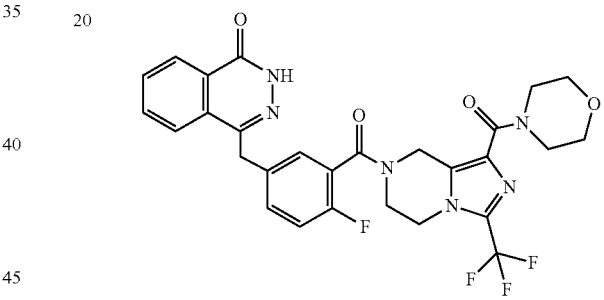<br>4-[[4-fluoro-3-[1-(morpholine-4-carbonyl)-3-(trifluoromethyl)-6,8-dihydro-5H-imidazo[1,5-a]pyrazine-7-carbonyl]phenyl]methyl]-2H-phthalazin-1-one |
| 21 | 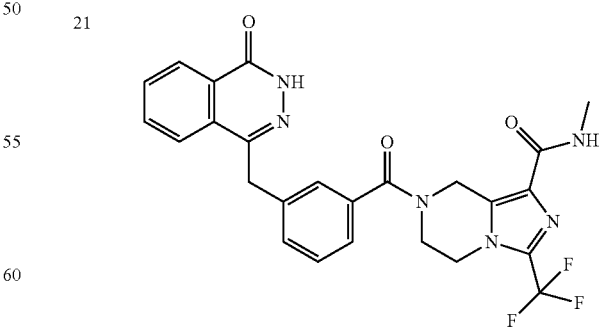<br>N-methyl-7-[3-[(4-oxo-3H-phthalazin-1-yl)methyl]benzoyl]-3-(trifluoromethyl)-6,8-dihydro-5H-imidazo[1,5-a]pyrazine-1-carboxamide |

| Example No. | Structure and Name |
|---|---|
| 22 | 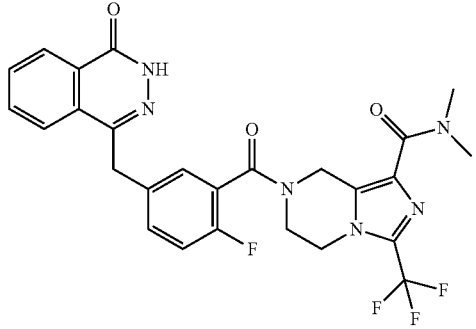<br>7-[2-fluoro-5-[(4-oxo-3H-phthalazin-1-yl)methyl]benzoyl]-N,N-dimethyl-3-(trifluoromethyl)-6,8-dihydro-5H-imidazo[1,5-a]pyrazine-1-carboxamide |
| 23 | 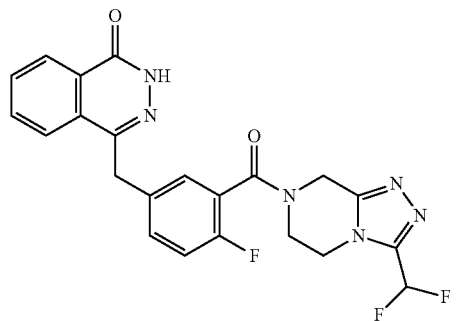<br>4-[[3-[3-(difluoromethyl)-6,8-dihydro-5H-[1,2,4]triazolo[4,3-a]pyrazine-7-carbonyl]-4-fluoro-phenyl]methyl]-2H-phthalazin-1-one |
| 24 | 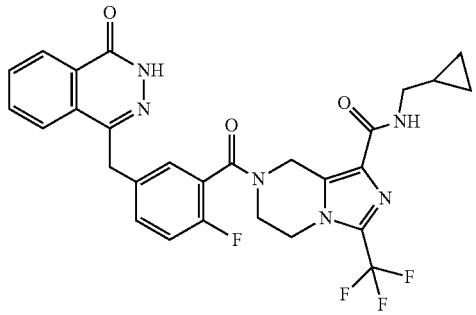<br>N-(cyclopropylmethyl)-7-[2-fluoro-5-[(4-oxo-3H-phthalazin-1-yl)methyl]benzoyl]-3-(trifluoromethyl)-6,8-dihydro-5H-imidazo[1,5-a]pyrazine-1-carboxamide |
| 25 | 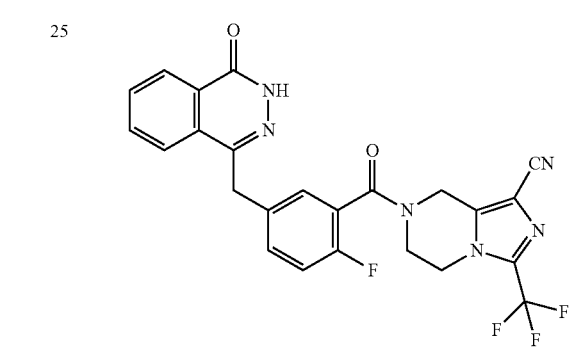<br>7-[2-fluoro-5-[(4-oxo-3H-phthalazin-1-yl)methyl]benzoyl]-3-(trifluoromethyl)-6,8-dihydro-5H-imidazo[1,5-a]pyrazine-1-carbonitrile |
| 26 | 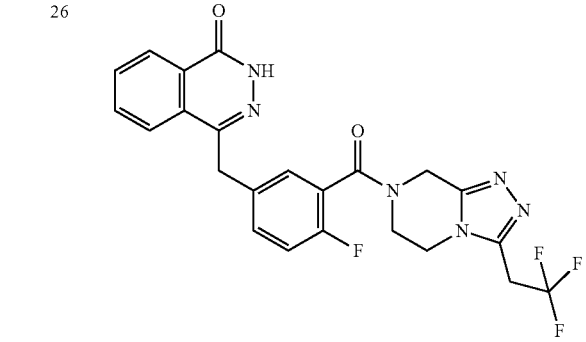<br>4-[[4-fluoro-3-[3-(2,2,2-trifluoroethyl)-6,8-dihydro-5H-[1,2,4]triazolo[4,3-a]pyrazine-7-carbonyl]phenyl]methyl]-2H-phthalazin-1-one | or pharmaceutically acceptable salts thereof.

This invention relates to a preparation process for a compound of formula (I) or a pharmaceutically acceptable salt thereof, comprising the steps of:

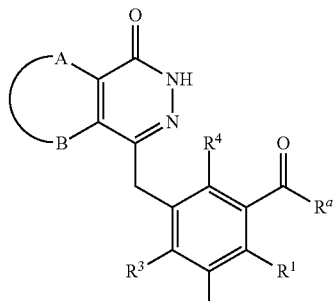

(IA)

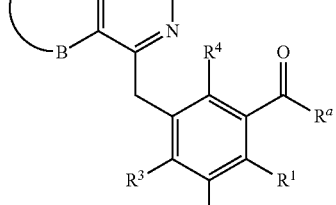

(IB)

optionally hydrolyzing a compound of formula (IA) to a carboxylic acid, reacting the carboxylic acid with a compound of formula (IB) or a salt thereof in the presence of a condensing agent such as benzotriazole-N,N,N',N'-tetramethyl urea hexafluorophosphate under an alkaline condition to obtain the compound of formula (I);

wherein:

$R^a$ is selected from the group consisting of hydroxyl, halogen and alkoxyl;

A, B, D, E, G and $R^1$ to $R^4$ are defined as those in formula (I).

In another aspect, this present invention relates to the use of the compounds of formula (I) or the pharmaceutically acceptable salt thereof in the preparation of the PARP inhibitors.

In another aspect, this present invention relates to a method for inhibiting PARP, comprising administering to a subject in need thereof a therapeutically effective amount of a compound of formula (I) or a pharmaceutically acceptable salt thereof.

In another aspect, this present invention relates to the use of a compound of formula (I) or a pharmaceutically acceptable salt thereof in the preparation of an adjuvant in the treatment of cancer or a medicament causing tumor cells to become sensitive to ionizing radiation or chemotherapy.

In another aspect, this present invention relates to a compound of formula (I) or a pharmaceutically acceptable salt thereof, for use as an adjuvant in the treatment of cancer or causing tumor cells to become sensitive to ionizing radiation or chemotherapy.

In another aspect, this present invention relates to a compound of formula (I) or a pharmaceutically acceptable salt thereof, for use as a PARP inhibitor.

In another aspect, this present invention relates to the use of a compound of formula (I) or a pharmaceutically acceptable salt thereof in the preparation of a medicament for the treatment of cancer, wherein said cancer is selected from the group consisting of breast cancer, ovarian cancer, pancreatic cancer, prostate cancer, liver cancer and colon cancer, wherein said medicament is further co-administered with a therapeutically effective amount of a drug selected from the group consisting of Temozolomide, Adriamycin, Taxol, Cisplatin, Carboplatin, Dacarbazine, Topotecan, Irinotecan, Gemcitabine and Bevacizumab.

In another aspect, this present invention relates to a method for treating cancer, comprising administering to a subject in need thereof a therapeutically effective amount of a compound of formula (I) or a pharmaceutically acceptable salt thereof, wherein said cancer is selected from the group consisting of breast cancer, ovarian cancer, pancreatic cancer, prostate cancer, liver cancer and colon cancer, wherein said compound of formula (I) or the pharmaceutically acceptable salt thereof is further co-administered with a therapeutically effective amount of a drug selected from the group consisting of Temozolomide, Adriamycin, Taxol, Cisplatin, Carboplatin, Dacarbazine, Topotecan, Irinotecan, Gemcitabine and Bevacizumab.

In another aspect, this present invention relates to a compound of formula (I) or a pharmaceutically acceptable salt thereof, for use as a medicament for the treatment of cancer, wherein said cancer is selected from the group consisting of breast cancer, ovarian cancer, pancreatic cancer, prostate cancer, liver cancer and colon cancer, wherein said medicament is further co-administered with a therapeutically effective amount of a drug selected from the group consisting of Temozolomide, Adriamycin, Taxol, Cisplatin, Carboplatin, Dacarbazine, Topotecan, Irinotecan, Gemcitabine and Bevacizumab.

Furthermore, the present invention also relates to a pharmaceutical composition, comprising a therapeutically effective amount of a compound of formula (I) or a pharmaceutically acceptable salt thereof according to the present invention, and a pharmaceutically acceptable carrier or excipient. The present invention relates to the pharmaceutical composition, for use as a PARP inhibitor, or as an adjuvant in the treatment of cancer or a medicament causing tumor cells to become sensitive to ionizing radiation or chemotherapy, or as a medicament for the treatment of cancer. The present invention relates to the use of the said pharmaceutical composition in the preparation of a PARP inhibitor. The present invention relates to the use of the pharmaceutical composition in the preparation of an adjuvant in the treatment of cancer or a medicament causing tumor cells to become sensitive to ionizing radiation or chemotherapy. The present invention relates to the use of the pharmaceutical composition in the preparation of a medicament for the treatment of cancer, wherein said cancer is selected from the group consisting of breast cancer, ovarian cancer, pancreatic cancer, prostate cancer, liver cancer and colon cancer, wherein said pharmaceutical composition is further co-administered with a therapeutically effective amount of a drug selected from the group consisting of Temozolomide, Adriamycin, Taxol, Cisplatin, Carboplatin, Dacarbazine, Topotecan, Irinotecan, Gemcitabine and Bevacizumab.

DETAILED DESCRIPTION OF THE INVENTION

Unless otherwise stated, the terms used in the specification and claims have the meanings described below.

"Alkyl" refers to a saturated aliphatic hydrocarbon group including C1-C20 straight chain and branched chain groups. Preferably an alkyl group is an alkyl having 1 to 12 carbon atoms. Representative examples include, but are not limited to methyl, ethyl, n-propyl, isopropyl, n-butyl, isobutyl, tert-butyl, sec-butyl, n-pentyl, 1,1-dimethyl propyl, 1,2-dimethyl propyl, 2,2-dimethyl propyl, 1-ethyl propyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and the isomers of branched chain thereof. More preferably an alkyl group is a lower alkyl having 1 to 6 carbon atoms. Representative examples include, but are not limited to methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl and etc. The alkyl group may be substituted or unsubstituted. When substituted, the substituent group(s) may be substituted at any available connection point, preferably the substituent group(s) is one or more groups independently selected from the group consisting of alkyl, alkenyl, alkynyl, alkyxoyl, alkylsulfo, alkylamino, halogen, thiol, hydroxyl, nitro, cyano, cycloalkyl, heterocyclic alkyl, aryl, heteroaryl, cycloalkyoxyl, heterolyic alkyoxyl, cycloalkylthio, heterolyic alkylthio, oxo, —C(O)OR$^5$, —OC(O)R$^5$, —O(CH$_2$)$_n$C(O)OR$^5$, —C(O)R$^5$, —NHC(O)R$^5$, —NR$^6$R$^7$, —OC(O)NR$^6$R$^7$ and —C(O)NR$^6$R$^7$.

"Cycloalkyl" refers to a saturated and/or partially unsaturated monocyclic or polycyclic hydrocarbon group and have 3 to 20 carbon atoms, preferably 3 to 12 carbon atoms, more preferably 3 to 10 carbon atoms. Representative examples of monocyclic cycloalkyl include, but are not limited to cyclopropyl, cyclobutyl, cyclopentyl, cyclopentenyl, cyclohexyl, cyclohexenyl, cyclohexadienyl, cycloheptyl, cycloheptatrienyl, cyclooctyl and etc. Polycyclic cycloalkyl includes the cycloalkyl having spiro ring, fused ring and bridged ring.

"Spiro Cycloalkyl" refers to a 5 to 20 membered polycyclic group with rings connected through one common carbon atom (called as spiro atom), wherein one or more rings may contain one or more double bonds, but none of the rings has a completely conjugated pi-electron system. Preferably a spiro cycloalkyl is 6 to 14 membered, more preferably 7 to 10 membered. According to the number of the common spiro atom, spiro cycloalkyl is divided into mono-spirocyclic ring, di-spirocyclic ring or poly-spirocyclic ring, preferably refers to mono-spirocyclic ring or di-spirocyclic ring. More preferably spiro cycloalkyl is 4-membered/4-membered, 4-membered/5-membered, 4-membered/6-membered, 5-membered/5-membered, or 5-membered/6-membered monocyclic spiro ring. Representative examples of spiro cycloalkyl include, but are not limited to the following groups:

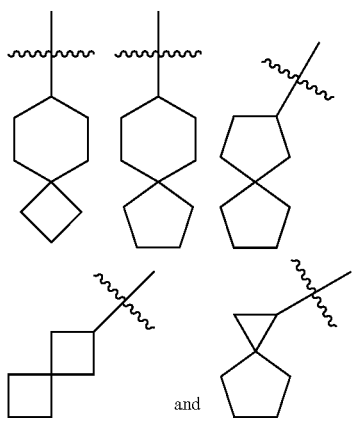

"Fused Cycloalkyl" refers to a 5 to 20 membered polycyclic hydrocarbon group, wherein each ring in the group shares an adjacent pair of carbon atoms with another ring in the group, wherein one or more rings can contain one or more double bonds, but none of the rings has a completely conjugated pi-electron system. Preferably a fused cycloalkyl group is 6 to 14 membered, more preferably 7 to 10 membered. According to the number of carbons in each membered ring, a fused cycloalkyl can be oriented into a bicyclic ring, tricyclic ring, tetracyclic ring or polycyclic ring fused cycloalkyl, preferably fused bicyclic ring or tricyclic ring fused cycloalkyl. More preferably the fused cycloalkyl is a 5-membered/5-membered, or 5-membered/6-membered bicyclic ring fused cycloalkyl. Representative examples of fused cycloalkyl include, but are not limited to, the following groups:

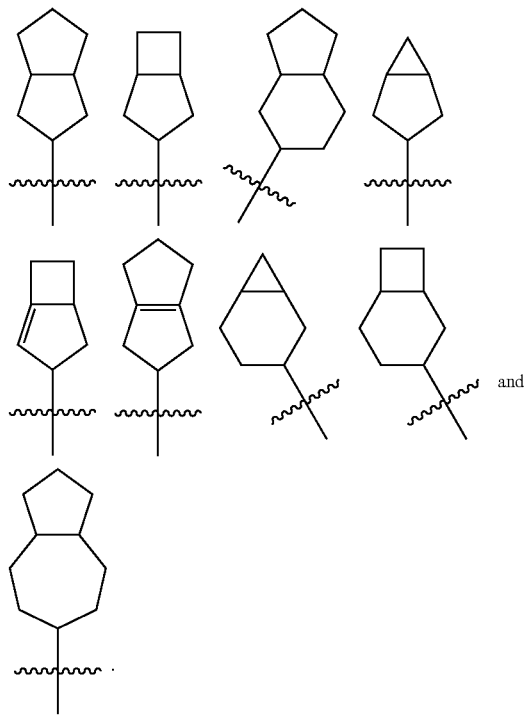

"Bridged Cycloalkyl" refers to a 5 to 20 membered polycyclic hydrocarbon group, wherein any two rings in the group share two disconnected carbon atoms. The rings can have one or more double bonds but have no completely conjugated pi-electron system. Preferably a bridged cycloalkyl is 6 to 14 membered, more preferably 7 to 10 membered. According to the number of membered ring, bridged cycloalkyl is divided into bridged bicyclic ring, tricyclic ring, tetracyclic ring or polycyclic ring, preferably refers to bicyclic ring, tricyclic ring or tetracyclic ring bridged cycloalkyl, more preferably bicyclic ring or tricyclic ring bridged cycloalkyl. Representative examples of bridged cycloalkyl include, but are not limited to the following groups:

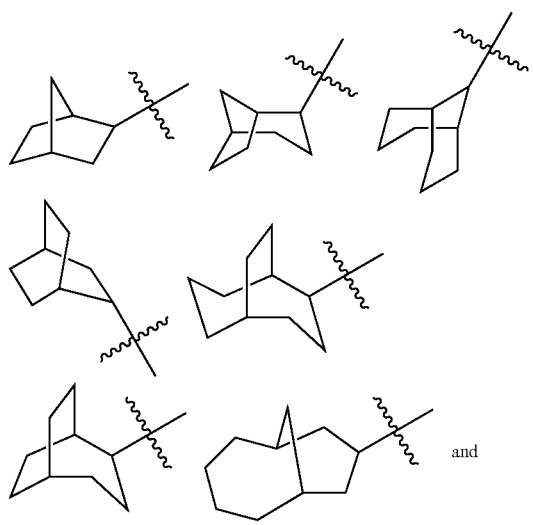

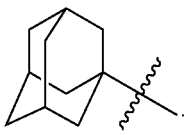

The said cycloalkyl can be fused to the ring of aryl, heteroaryl or heterocyclic alkyl, wherein the ring connected with parent structure is cycloalkyl. Representative examples include, but are not limited to indanylacetic, tetrahydronaphthalene, benzocydoheptyl and so on. The said cycloalkyl may be optionally substituted or unsubstituted. When substituted, the substituent group(s) is preferably one or more groups independently selected from the group consisting of alkyl, alkenyl, alkynyl, alkyxoyl, alkylsulfo, alkylamino, halogen, thiol, hydroxyl, nitro, cyano, cycloalkyl, heterocyclic alkyl, aryl, heteroaryl, cycloalkyoxyl, heterocylic alkyoxyl, cycloalkylthio, heterocylic alkylthio, oxo, —C(O)OR$^5$, —OC(O)R$^5$, —O(CH$_2$)$_n$C(O)OR$^5$, —C(O)R$^5$, —NHC(O)R$^5$, —NR$^6$R$^7$, —OC(O)NR$^6$R$^7$ and —C(O)NR$^6$R$^7$.

"Alkenyl" refers to an alkyl defined as above that have at least two carbon atoms and at least one carbon-carbon double bond. For example, vinyl, 1-propenyl, 2-propenyl, 1-, 2- or 3-butenyl and etc. The alkenyl group may be substituted or unsubstituted. When substituted, the substituent group(s) is preferably one or more group(s) independently selected from the group consisting of alkyl, alkenyl, alkynyl, alkyxoyl, alkylsulfo, alkylamino, halogen, thiol, hydroxyl, nitro, cyano, cycloalkyl, heterocyclic alkyl, aryl, heteroaryl, cycloalkyoxyl, heterocylic alkyoxyl, cycloalkylthio, heterocylic alkylthio, —C(O)OR$^5$, —OC(O)R$^5$, —O(CH$_2$)$_n$C(O)OR$^5$, —C(O)R$^5$, —NHC(O)R$^5$, —NR$^6$R$^7$, —OC(O)NR$^6$R$^7$ and —C(O)NR$^6$R$^7$.

"Alkynyl" refers to an alkyl defined as above that have at least two carbon atoms and at least one carbon-carbon triple bond. For example, ethynyl, 1-propynyl, 2-propynyl, 1-, 2- or 3-butynyl and etc. The alkynyl group may be substituted or unsubstituted. When substituted, the substituent group(s) is preferably one or more group(s) independently selected from the group consisting of alkyl, alkenyl, alkynyl, alkyxoyl, alkylsulfo, alkylamino, halogen, thiol, hydroxyl, nitro, cyano, cycloalkyl, heterocyclic alkyl, aryl, heteroaryl, cycloalkyoxyl, heterocylic alkyoxyl, cycloalkylthio, heterocylic alkylthio, —C(O)OR$^5$, —OC(O)R$^5$, —O(CH$_2$)$_n$C(O)OR$^5$, —C(O)R$^5$, —NHC(O)R$^5$, —NR$^6$R$^7$, —OC(O)NR$^6$R$^7$ and —C(O)NR$^6$R$^7$.

"Heterocyclyl" refers to 3 to 20 membered saturated and/or partially unsaturated monocyclic or polycyclic hydrocarbon group having one or more heteroatoms selected from the group consisting of N, O, or S(O)m (wherein m is 0, 1 or 2) as ring atoms, but excluding —O—O—, —O—S— or —S—S— in the ring, the remaining ring atoms being C. Preferably, heterocyclyl is 3 to 12 membered having 1 to 4 said heteroatoms; more preferably 3 to 10 membered. Representative examples of monocyclic heterocyclyl include, but are not limited to pyrrolidyl, piperidyl, piperazinyl, morpholinyl, sulfo-morpholinyl, homopiperazinyl and so on. Polycyclic heterocyclyl includes the heterocyclyl having spiro ring, fused ring and bridged ring. "Spiro heterocyclyl" refers to 5 to 20 membered polycyclic heterocyclyl with rings connected through one common carbon atom (called as spiro atom), wherein said rings have one or more heteroatoms selected from the group consisting of N, O, and S(O)$_p$ (wherein p is 0, 1 or 2) as ring atoms, the remaining ring atoms being C, wherein one or more rings may contain one or more double bonds, but none of the rings has a completely conjugated pi-electron system. Preferably a spiro heterocyclyl is 6 to 14 membered, more preferably 7 to 10 membered. According to the number of common spiro atoms, spiro heterocyclyl is divided into mono-spiro heterocyclyl, di-spiro heterocyclyl or poly-spiro heterocyclyl, preferably refers to mono-spiro heterocyclyl and di-spiro heterocyclyl. More preferably spiro heterocyclyl is 4-membered/4-membered, 4-membered/5-membered, 4-membered/6-membered, 5-membered/5-membered, or 5-membered/6-membered mono-spiro heterocyclyl. Representative examples of spiro heterocyclyl include, but are not limited to the following groups:

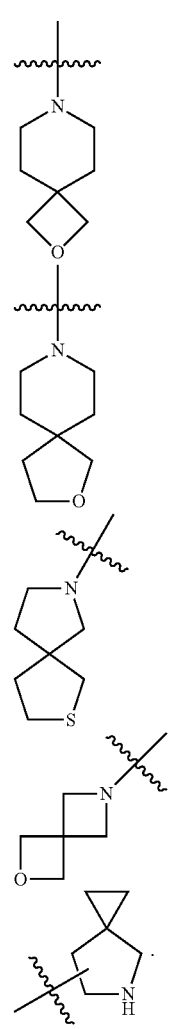

and

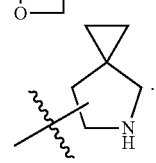

"Fused Heterocyclyl" refers to a 5 to 20 membered polycyclic heterocyclyl group, wherein each ring in the group shares an adjacent pair of carbon atoms with another ring in the group, wherein one or more rings can contain one or more double bonds, but none of the rings has a completely conjugated pi-electron system, and wherein said rings have one or more heteroatoms selected from the group consisting of N, O, and S(O)$_p$ (wherein p is 0, 1 or 2) as ring atoms, the remaining ring atoms being C. Preferably a fused heterocyclyl is 6 to 14 membered, more preferably 7 to 10 membered. According to the number of membered ring, the fused heterocyclyl is divided into bicyclic ring, tricyclic ring, tetracyclic ring or polycyclic ring fused heterocyclyl, preferably refers to bicyclic ring or tricyclic ring fused heterocyclyl. More preferably fused heterocyclyl is 5-membered/5-membered, or 5-membered/6-membered bicyclic ring fused heterocyclyl. Representative examples of fused heterocyclyl include, but are not limited to the following groups:

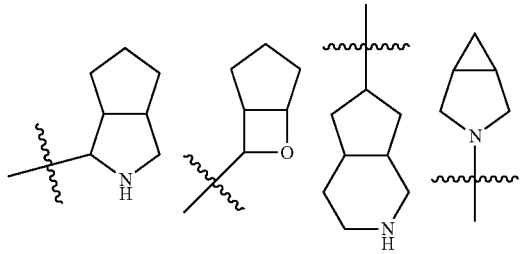

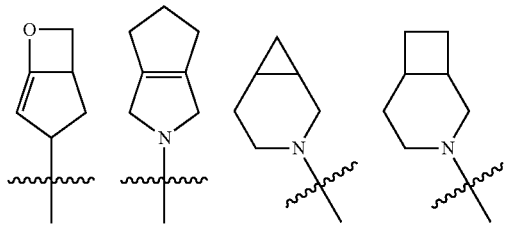

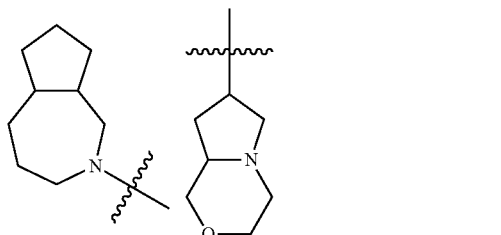

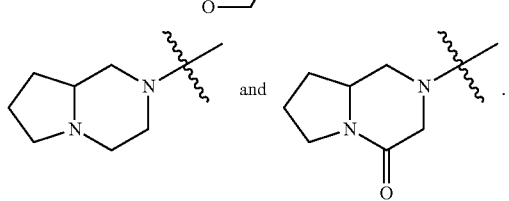

"Bridged Heterocyclyl" refers to a 5 to 14 membered polycyclic heterocyclyl group, wherein any two rings in the group share two disconnected atoms, the rings can have one or more double bonds but have no completely conjugated pi-electron system, and the rings have one or more heteroatoms selected from the group consisting of N, O, and S(O)$_m$ (wherein m is 0, 1 or 2) as ring atoms, the remaining ring atoms being C. Preferably a bridged heterocyclyl is 6 to 14 membered, more preferably 7 to 10 membered. According to the number of membered ring, bridged heterocyclyl is divided into bicyclic ring, tricyclic ring, tetracyclic ring or polycyclic ring bridged heterocyclyl, preferably refers to bicyclic ring, tricyclic ring or tetracyclic ring bridged heterocyclyl, more preferably bicyclic ring or tricyclic ring bridged heterocyclyl. Representative examples of bridged heterocyclyl include, but are not limited to the following groups:

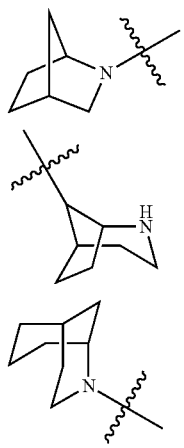

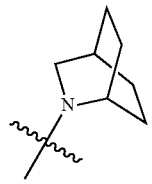

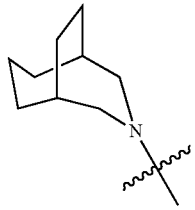

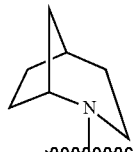

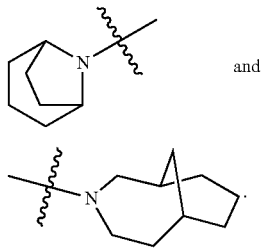

The said ring of heterocyclyl can be fused to the ring of aryl, heteroaryl or cycloalkyl, wherein the ring connected with parent structure is heterocyclyl. Representative examples include, but are not limited to, the following groups:

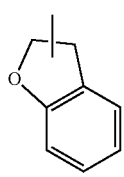

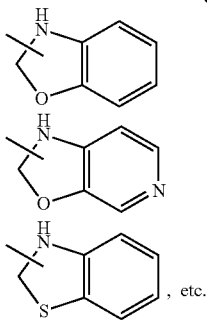

The heterocyclyl may be optionally substituted or unsubstituted. When substituted, the substituent group(s) is preferably one or more group(s) independently selected from the group consisting of alkyl, alkenyl, alkynyl, alkyxoyl, alkylsulfo, alkylamino, halogen, thiol, hydroxyl, nitro, cyano, cycloalkyl, heterocyclic alkyl, aryl, heteroaryl, cycloalkyoxyl, heterocylic alkyoxyl, cycloalkylthio, heterocylic alkylthio, oxo, —C(O)OR$^5$, —OC(O)R$^5$, —O(CH$_2$)$_n$C(O)OR$^5$, —C(O)R$^5$, —NHC(O)R$^5$, —NR$^6$R$^7$, —OC(O)NR$^6$R$^7$ and —C(O)NR$^6$R$^7$.

"Aryl" refers to a 6 to 14 membered all-carbon monocyclic ring or a polycyclic fused ring (a "fused" ring system means that each ring in the system shares an adjacent pair of carbon atoms with other ring in the system) group, and has a completely conjugated pi-electron system. Preferably aryl is 6 to 10 membered, such as phenyl and naphthyl. The said aryl can be fused to the ring of heteroaryl, heterocyclyl or cycloalkyl, wherein the ring connected with parent structure is aryl. Representative examples include, but are not limited to, the following groups:

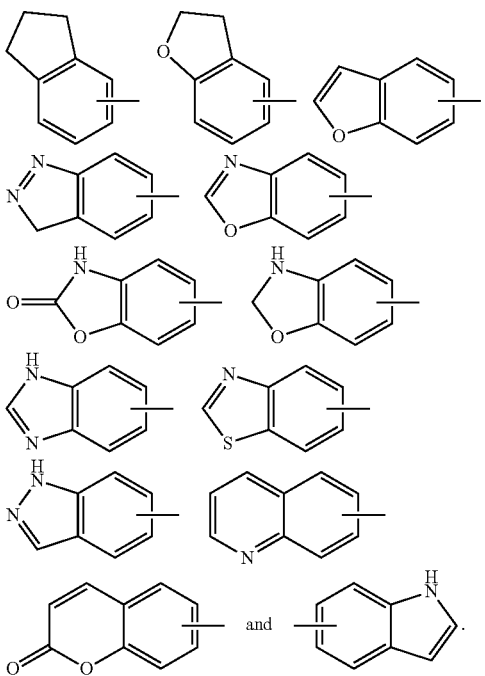

The aryl group may be substituted or unsubstituted. When substituted, the substituent group(s) is preferably one or more groups independently selected from the group consisting of alkyl, alkenyl, alkynyl, alkyxoyl, alkylsulfo, alkylamino, halogen, thiol, hydroxyl, nitro, cyano, cycloalkyl, heterocyclic alkyl, aryl, heteroaryl, cycloalkyoxyl, heterocylic alkyoxyl, cycloalkylthio, heterocylic alkylthio, —C(O)OR$^5$, —OC(O)R$^5$, —O(CH$_2$)$_n$C(O)OR$^5$, —C(O)R$^5$, —NHC(O)R$^5$, —NR$^6$R$^7$, —OC(O)NR$^6$R$^7$ and —C(O)NR$^6$R$^7$.

"Heteroaryl" refers to a heteroaryl system having 1 to 4 heteroatoms selected from the group consisting of O, S and N as ring atoms and having 5 to 14 annular atoms. Preferably heteroaryl is 5- to 10-membered. More preferably heteroaryl is 5- or 6-membered. The examples of heteroaryl groups include furyl, thienyl, pyridyl, pyrrolyl, N-alkyl pyrrolyl, pyrimidinyl, pyrazinyl, imidazolyl, tetrazolyl, and the like. The said heteroaryl can be fused with the ring of aryl, heterocyclyl or cycloalkyl, wherein the ring connected with parent structure is heteroaryl. Representative examples include, but are not limited to the following groups,

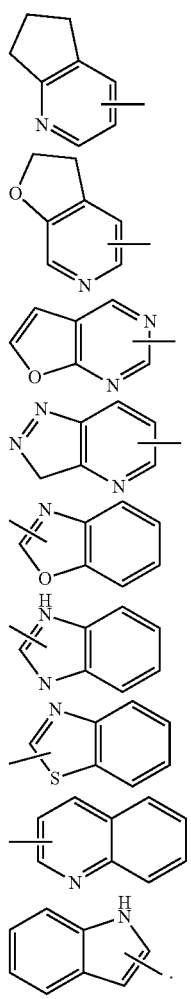

The heteroaryl group may be substituted or unsubstituted. When substituted, the substituent group(s) is preferably one or more groups independently selected from the group consisting of alkyl, alkenyl, alkynyl, alkyxoyl, alkylsulfo, alkylamino, halogen, thiol, hydroxyl, nitro, cyano, cycloalkyl, heterocyclic alkyl, aryl, heteroaryl, cycloalkyoxyl, heterocylic alkyoxyl, cycloalkylthio, heterocylic alkylthio, —C(O)OR⁵, —OC(O)R⁵, —O(CH₂)ₙC(O)OR⁵, —C(O)R⁵, —NHC(O)R⁵, —NR⁶R⁷, —OC(O)NR⁶R⁷ and —C(O)NR⁶R⁷.

"Alkoxyl" refers to both an —O-(alkyl) and an —O-(unsubstituted cycloalkyl) group, wherein the alkyl is defined as above. Representative examples include, but are not limited to, methoxy, ethoxy, propoxy, butoxy, cyclopropyloxy, cyclobutyloxy, cyclopentyloxy, cyclohexyloxy, and the like. The alkoxyl may be optionally substituted or unsubstituted. When substituted, the substituent is preferably one or more groups independently selected from the group consisting of alkyl, alkenyl, alkynyl, alkyxoyl, alkylsulfo, alkylamino, halogen, thiol, hydroxyl, nitro, cyano, cycloalkyl, heterocyclic alkyl, aryl, heteroaryl, cycloalkyoxyl, heterocylic alkyoxyl, cycloalkylthio, heterocylic alkylthio, —C(O)OR⁵, —OC(O)R⁵, —O(CH₂)ₙC(O)OR⁵, —C(O)R⁵, —NHC(O)R⁵, —NR⁶R⁷, —OC(O)NR⁶R⁷ and —C(O)NR⁶R⁷.

"Hydroxy" refers to an —OH group.

"Halogen" refers to a fluoro, chloro, bromo or iodo atom.

"Amino" refers to a —NH₂ group.

"Cyano" refers to a —CN group.

"Nitro" refers to a —NO₂ group.

"Benzyl" refers to a —CH₂-(phenyl) group.

"Oxo" refers to an =O group.

"Carboxyl" refers to a —C(O)OH group.

"Alkoxycarbonyl" refers to a —C(O)O(alkyl) or (cycloalkyl) group, wherein the alkyl and cycloalkyl are defined as above.

"Optional" or "optionally" means that the event or circumstance described subsequently may, but need not to occur, and the description includes the instances of the event or circumstance may or may not occur. For example, "the heterocyclic group optionally substituted by an alkyl" means that an alkyl group may be, but need not to be present, and the description includes the case of the heterocyclic group being substituted with an alkyl and the heterocyclic group being not substituted with an alkyl.

"Substituted" refers to one or more hydrogen atoms in the group, preferably up to 5, more preferably 1 to 3 hydrogen atoms independently substituted with a corresponding number of substituents. It goes without saying that the substituents exist in their only possible chemical position. The person skilled in the art is able to determine if the substitution is possible or impossible without paying excessive efforts by experiment or theory. For example, the combination of amino or hydroxyl group having free hydrogen and carbon atoms having unsaturated bonds (such as olefinic) may be unstable.

A "pharmaceutical composition" refers to a mixture of one or more of the compounds described in the present invention or physiologically/pharmaceutically acceptable salts or prodrugs thereof and other chemical components such as physiologically/pharmaceutically acceptable carriers and excipients. The purpose of a pharmaceutical composition is to facilitate administration of a compound to an organism, which is conducive to the absorption of the active ingredient and thus displaying biologically activity.

m, n and R⁵ to R⁷ are defined as those in the compounds of formula (I).

Synthesis Method of the Compound in the Present Invention

In order to complete the purpose of the invention, the present invention applies the following technical solution:

A preparation method of a compound of formula (I) of the invention or a pharmaceutically acceptable salt thereof, comprising the steps of:

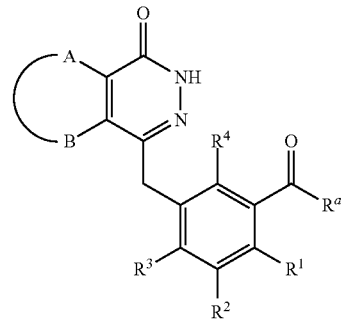

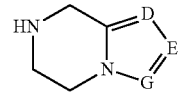

optionally hydrolyzing a compound of formula (IA) to a carboxylic acid, then reacting the carboxylic acid with a compound of formula (IB) or salt thereof in the presence of a condensing reagent such as benzotriazole-N,N,N',N'-tetramethyl urea hexafluorophosphate under an alkaline condition to obtain the compound of formula (I);

wherein:

Rᵃ is selected from the group consisting of hydroxyl, halogen and alkoxyl;

A, B, D, E, G and R¹ to R⁴ are defined as those in the formula (I).

The above condensation reaction is carried out between an acid compound and an amine compound in the presence of a condensing agent under basic condition, wherein the condensing agent is selected from the group consisting of N,N'-dicyclohexylcarbodiimide, N,N'-Diisopropylcarbodiimide and O-(benzotriazol-1-yl)-N,N,N',N'-tetramethyluronium tetrafluoroborate (TBTU), preferably O-(benzotriazol-1-yl)-N,N,N',N'-tetramethyluronium tetrafluoroborate (TBTU); alkaline condition is provided by an organic or inorganic base, wherein the organic base is selected from the group consisting of diisopropyl ethylamine, pyridine, triethylamine, hexahydropyridine, N-methyl-piperazine, 4-dimethylamino pyridine, etc., preferably diisopropyl ethylamine; wherein the solvent used is selected from the group consisting of toluene, benzene, dichloromethane, tetrahydrofuran, chloroform, N,N-dimethyl formamide, or the mixture of the solvents above, preferably N,N-dimethyl formamide; the reaction temperature is controlled between −80° C. and 100° C., preferably between 0° C. and 60° C.; reaction time is usually controlled between 1 minute and 72 hours, preferably between 15 minutes and 24 hours.

PREFERRED EMBODIMENTS

The following examples serve to illustrate the invention, but the examples should not be considered as limiting the scope of the invention.

EXAMPLES

The compound's structure was indentified by NMR and/or MS. NMR chemical shifts (δ) were given in 10⁻⁶ (ppm). NMR is determined by a Bruker AVANCE-400 machine. The solvents were deuterated-dimethyl sulfoxide (DMSO-d₆), deuterated-chloroform (CDCl₃) and deuterated-methanol (CD₃OD) with tetramethylsilane (TMS) as an internal standard.

MS was determined by a FINNIGAN LCQAd (ESI) mass spectrometer (manufacturer: Thermo, type: Finnigan LCQ advantage MAX).

HPLC was determined on an Agilent 1200DAD high pressure liquid chromatography spectrometer (Sunfire C18 150×4.6 mm chromatographic column) and a Waters 2695-2996 high pressure liquid chromatography spectrometer (Gimini C18 150×4.6 mm chromatographic column).

$IC_{50}$ was determined by a NovoStar ELIASA (BMG Co., German);

The thin-layer silica gel used Yantai Huanghai HSGF254 or Qingdao GF254 silica gel plate. The dimension of the plates used in TLC was 0.15 mm to 0.2 mm, and the dimension of the plates used in thin-layer chromatography for product purification was 0.4 mm to 0.5 mm.

Column chromatography generally used Yantai Huanghai 200 to 300 mesh silica gel as carrier.

The known starting material of the invention can be prepared by the conventional synthesis method in the prior art, or be purchased from ABCR GmbH & Co. KG, Acros Organics, Aldrich Chemical Company, Accela ChemBio Inc or Dari chemical Company, etc.

Unless otherwise stated in the examples, the following reactions were placed under argon atmosphere or nitrogen atmosphere.

The term "argon atmosphere" or "nitrogen atmosphere" refers to that a reaction flask is equipped with a balloon having 1 L of argon or nitrogen.

In hydrogenation reactions, the reaction system was generally vacuumed and filled with hydrogen, and the above operation was repeated for three times.

Microwave reactions were performed with a CEM Discover-S 908860 microwave reactor.

Unless otherwise stated in the examples, the solution used in following reactions refers to an aqueous solution.

Unless otherwise stated in the examples, the reaction temperature in the following reaction was room temperature.

Room temperature was the most proper reaction temperature, which was 20° C. to 30° C.

The reaction process was monitored by thin layer chromatography (TLC), the system of developing solvent included: A: dichloromethane and methanol system, B: n-hexane and ethyl acetate system, C: petroleum ether and ethyl acetate system, D: acetone. The ratio of the volume of the solvent was adjusted according to the polarity of the compounds.

The elution system for purifying the compounds by column chromatography and thin layer chromatography included: A: dichloromethane and methanol system, B: n-hexane and ethyl acetate system, the ratio of the volume of the solvent was adjusted according to the polarity of the compounds, and sometimes a little alkaline reagent such as triethylamine or an acidic reagent such as acetic acid was also can be added.

Example 1

4-[[4-fluoro-3-[3-(trifluoromethyl)-6,8-dihydro-5H-[1,2,4]triazolo[4,3-a]pyrazine-7-carbonyl]phenyl]methyl]-2H-phthalazin-1-one

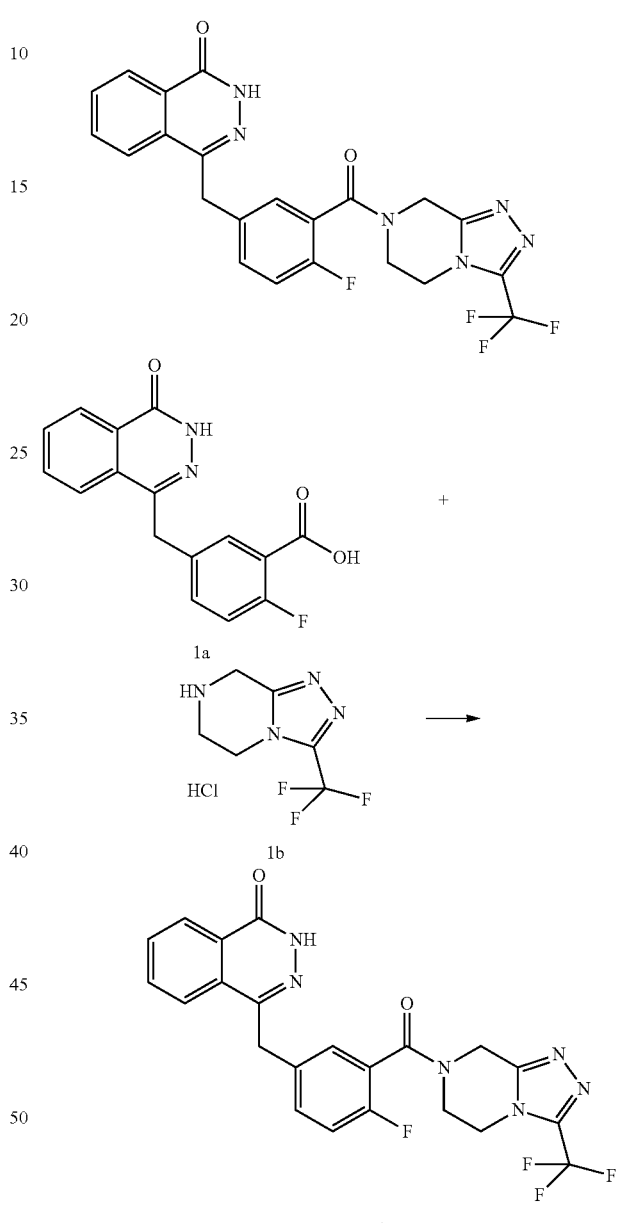

2-Fluoro-5-[(4-oxo-3H-phthalazin-1-yl)methyl]benzoic acid 1a (150 mg, 0.50 mmol, prepared according to a known method disclosed by "patent application WO2004080976") was dissolved in 2 mL of N,N-dimethylformamide, followed by addition of O-(1-benzotriazolyl)-N,N,N',N'-tetramethyluronium hexafluorophosphate (284 mg, 0.75 mmol), 3-(trifluoromethyl)-5,6,7,8-tetrahydro-[1,2,4]triazolo[4,3-a]pyrazine hydrochloride 1b (138 mg, 0.60 mmol, prepared according to a known method disclosed by "patent application WO2004080958") and N, N-diisopropylethylamine (0.2 mL, 1 mmol). After stirring for 12 hours, the reaction mixture was concentrated under reduced pressure and the resulting residue was purified by thin layer chromatography with elution system A to obtain 4-[[4-fluoro-3-[3-(trifluoromethyl)-6,8-dihydro-5H-[1,2,4]triazolo[4,3-a]pyrazine-7-carbonyl]phenyl]methyl]-2H-phthalazin-1-one 1 (25 mg, yield 10.6%) as a white solid.

MS m/z (ESI): 473.2 [M+1]

¹H NMR (400 MHz, CDCl₃): δ 10.04 (br. s, 1H), 8.48 (d, 1H), 7.80 (m, 3H), 7.55 (m, 1H), 7.40 (m, 1H), 7.15 (m, 1H), 4.29 (s, 2H), 4.23 (m, 2H), 3.74 (m, 2H), 3.20 (m, 2H)

Example 2

4-[[3-(3,4-dihydro-1H-pyrrolo[1,2-a]pyrazine-2-carbonyl)-4-fluoro-phenyl]methyl]-2H-phthalazin-1-one

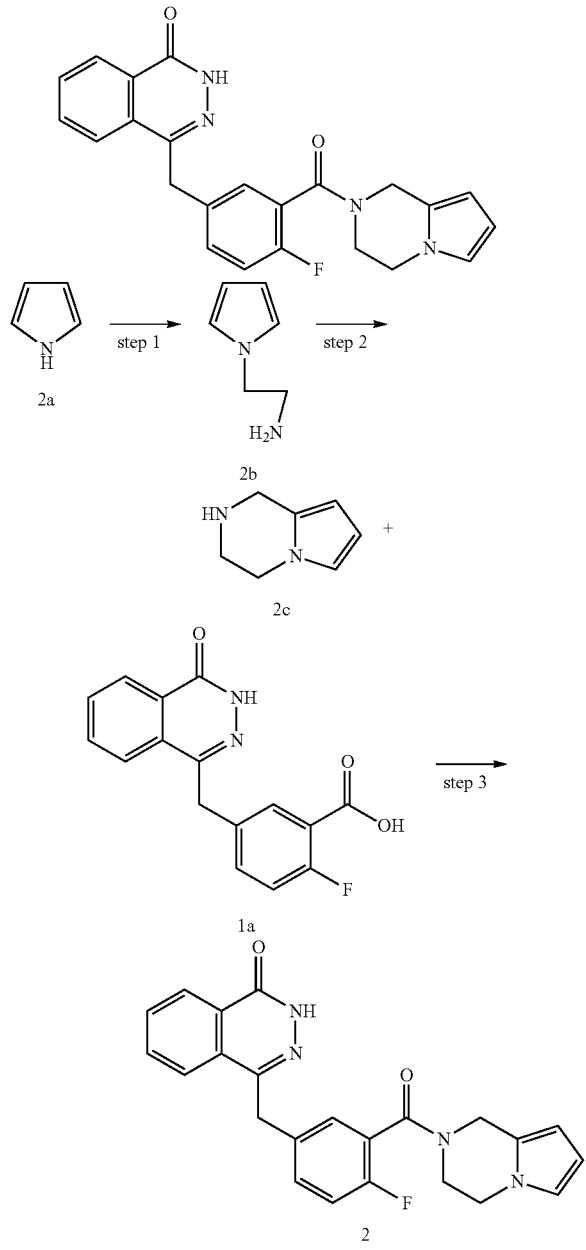

Step 1

2-pyrrol-1-yl-ethanamine

Pyrrole 2a (12 g, 17.90 mmol) was dissolved in 150 mL of acetonitrile, followed by addition of 2-chloroethylamine hydrochloride (24.60 g, 21.20 mmol), sodium hydroxide (0.50 g, 4 mmol) and tetrabutyl ammonium hydrogen sulfate (2.40 g, 7 mmol). After stirring for 4 hours under reflux condition, the reaction mixture was heated to 50° C. and reacted for 12 hours. The reaction mixture was concentrated under reduced pressure to obtain 2-pyrrol-1-yl-ethanamine 2b (8 g, yield 41.0%) as a light yellow oil.

Step 2

1,2,3,4-tetrahydropyrrolo[1,2-a]pyrazine

2-Pyrrol-1-yl-ethanamine 2b (2 g, 18 mmol) was dissolved in 40 mL of ethanol, followed by addition of formaldehyde solution (40%, 1.5 mL, 18 mmol) and a slow dropwise addition of 1 mL of trifluoroacetic acid. The reaction mixture was heated to 50° C. for 15 minutes, then cooled to room temperature and stirred for 12 hours. The reaction mixture was concentrated under reduced pressure, added with 50 mL of ethyl acetate, washed with saturated sodium bicarbonate solution (50 mL), dried over anhydrous sodium sulfate and filtered. The filtrate was concentrated under reduced pressure to obtain 1,2,3,4-tetrahydropyrrolo[1,2-a]pyrazine 2c (1.60 g, yield 72.7%) as a light yellow oil.

Step 3

4-[[3-(3,4-dihydro-1H-pyrrolo[1,2-a]pyrazine-2-carbonyl)-4-fluoro-phenyl]methyl]-2H-phthalazin-1-one 2-Fluoro-5-[(4-oxo-3H-phthalazin-1-yl)methyl]benzoic acid 1a (300 mg, 1 mmol) was dissolved in 3 mL of N,N-dimethylformamide, followed by addition of O-(1-benzotriazolyl)-N,N,N',N'-tetramethyluronium hexafluorophosphate (568 mg, 1.50 mmol), 1,2,3,4-tetrahydropyrrolo[1,2-a]pyrazine 2c (210 mg, 1.50 mmol) and N,N-diisopropylethylamine (350 μL, 2 mmol). After stirring for 12 hours, the reaction mixture was concentrated under reduced pressure and the resulting residue was purified by thin layer chromatography with elution system A to obtain 4-[[3-(3,4-dihydro-1H-pyrrolo[1,2-a]pyrazine-2-carbonyl)-4-fluoro-phenyl]methyl]-2H-phthalazin-1-one 2 (15 mg, yield 3.7%) as a white solid.

MS m/z (ESI): 403.1 [M+1]

¹H NMR (400 MHz, CDCl₃): δ 10.19 (br. s, 1H), 8.51 (d, 1H), 7.82 (m, 3H), 7.41 (m, 2H), 7.13 (m, 1H), 6.65 (m, 1H), 6.24 (m, 1H), 5.81 (m, 1H), 4.97 (s, 1H), 4.59 (s, 1H), 4.33 (s, 2H), 4.13 (m, 1H), 4.00 (m, 1H), 3.71 (m, 1H), 2.85 (m, 1H)

Example 3 methyl 7-[2-fluoro-5-[(4-oxo-3H-phthalazin-1-yl)methyl]benzoyl]-3-(trifluoromethyl)-6,8-dihydro-5H-imidazo[1,5-a]pyrazine-1-carboxylate

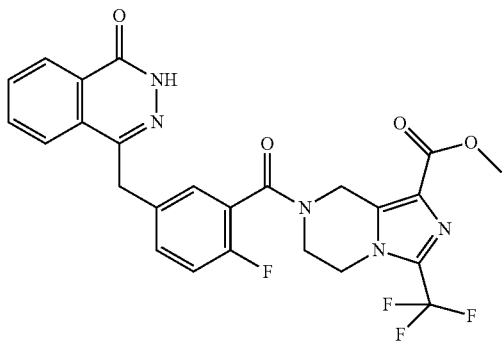

3a

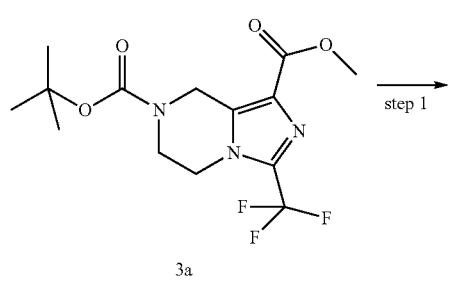

3b

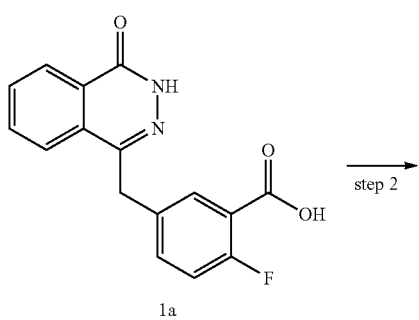

1a

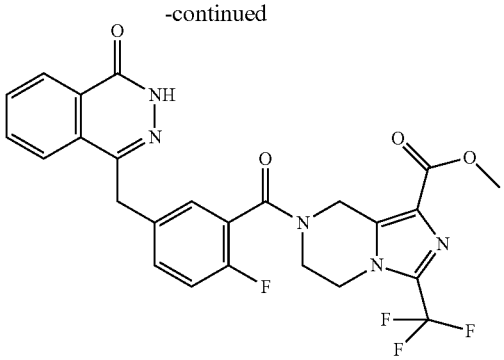

3

Step 1 methyl 3-(trifluoromethyl)-5,6,7,8-tetrahydroimidazo[1,5-a]pyrazine-1-carboxylate O-7-tert-butyl-O-1-methyl-3-(trifluoromethyl)-6,8-dihydro-5H-imidazo[1,5-a]pyrazine-1,7-dicarboxylate 3a (600 mg, 1.72 mmol, prepared according to a known method disclosed by "patent application WO2009082881") was dissolved in 20 mL of a solution of hydrogen chloride in 1,4-dioxane (2 M). After stirring for 5 hours, the reaction mixture was concentrated under reduced pressure and added with 50 mL of dichloromethane. Saturated sodium bicarbonate solution was added dropwise to the reaction mixture until the pH is 8. The organic phase was separated, dried over anhydrous sodium sulfate and filtered. The filtrate was concentrated under reduced pressure to obtain crude methyl 3-(trifluoromethyl)-5,6,7,8-tetrahydroimidazo[1,5-a]pyrazine-1-carboxylate 3b (430 mg) as a white solid. The product was used directly in the next reaction without purification.

Step 2 methyl 7-[2-fluoro-5-[(4-oxo-3H-phthalazin-1-yl)methyl]benzoyl]-3-(trifluoromethyl)-6,8-dihydro-5H-imidazo[1,5-a]pyrazine-1-carboxylate 2-Fluoro-5-[(4-oxo-3H-phthalazin-1-yl)methyl]benzoic acid 1a (300 mg, 1 mmol) was dissolved in 2 mL of N,N-dimethylformamide, followed by addition of O-(1-benzotriazolyl)-N,N,N',N'-tetramethyluronium hexafluorophosphate (568 mg, 1.50 mmol), crude methyl 3-(trifluoromethyl)-5,6,7,8-tetrahydroimidazo[1,5-a]pyrazine-1-carboxylate 3b (300 mg, 1.50 mmol) and N,N-diisopropylethylamine (0.4 mL, 2 mmol). After stirring for 12 hours, the reaction mixture was concentrated under reduced pressure and the resulting residue was purified by thin layer chromatography with elution system A to obtain methyl 7-[2-fluoro-5-[(4-oxo-3H-phthalazin-1-yl)methyl]benzoyl]-3-(trifluoromethyl)-6,8-dihydro-5H-imidazo[1,5-a]pyrazine-1-carboxylate 3 (120 mg, yield 23.0%) as a light yellow solid.

MS m/z (ESI): 530.1 [M+1]

$^1$H NMR (400 MHz, CDCl$_3$): δ 10.48 (br. s, 1H), 8.52 (d, 1H), 7.87 (m, 3H), 7.43 (m, 2H), 7.30 (m, 1H), 5.02 (m, 2H), 4.34 (s, 2h), 4.17 (m, 2H), 3.99 (m, 2H), 3.00 (s, 3H)

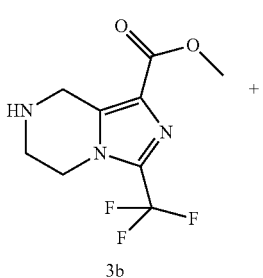

Example 4

4-[[3-(6,8-dihydro-5H-imidazo[1,2-a]pyrazine-7-carbonyl)-4-fluoro-phenyl]methyl]-2H-phthalazin-1-one

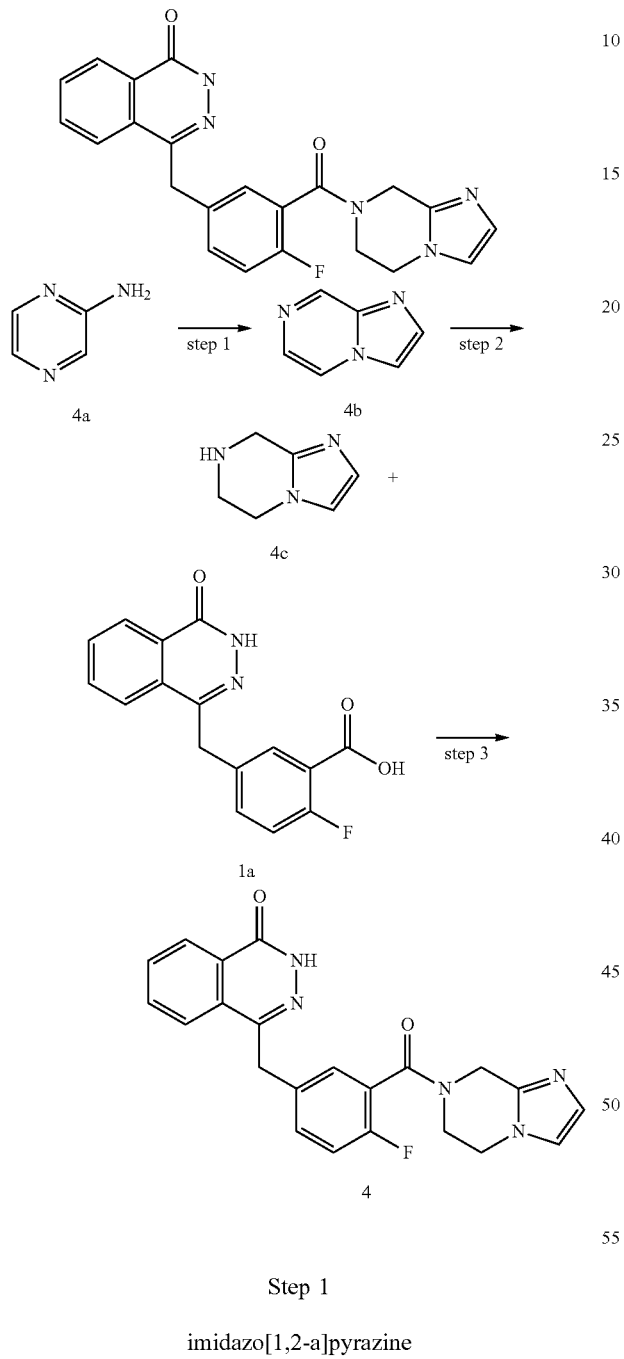

Step 1 imidazo[1,2-a]pyrazine

Pyrazin-2-amine 4a (5 g, 52 mmol) was dissolved in a 40% 2-chloroacetaldehyde solution (15 mL, 78 mmol), followed by addition of sodium bicarbonate (6.60 g, 78 mmol). After stirring for 48 hours at 100° C., the reaction mixture was cooled to room temperature, added with 100 mL of a saturated potassium carbonate solution, and extracted with dichloromethane (100 mL×3). The organic phase was combined, dried over anhydrous sodium sulfate and filtered. The filtrate was concentrated under reduced pressure to obtain imidazo[1,2-a]pyrazine 4b (3 g, yield 50.0%) as a brown solid.

MS m/z (ESI): 120.1 [M+1]

Step 2

5,6,7,8-tetrahydroimidazo[1,2-a]pyrazine

Imidazo[1,2-a]pyrazine 4b (500 mg, 4.20 mmol) was dissolved in 5 mL of 2-methoxyethanol, followed by addition of platinum dioxide (100 mg, 0.36 mmol), and the reactor was purged with hydrogen for three times. After stirring for 12 hours, the reaction mixture was filtered. The filtrate was concentrated under reduced pressure to obtain 5,6,7,8-tetrahydroimidazo[1,2-a]pyrazine 4c (200 mg, yield 38.7%) as a yellow oil.

MS m/z (ESI): 124.1 [M+1]

Step 3

4-[[3-(6,8-dihydro-5H-imidazo[1,2-a]pyrazine-7-carbonyl)-4-fluoro-phenyl]methyl]-2H-phthalazin-1-one 2-Fluoro-5-[(4-oxo-3H-phthalazin-1-yl)methyl]benzoic acid 1a (323 mg, 1.08 mmol) was dissolved in 5 mL of N,N-dimethylformamide, followed by addition of O-(1-benzotriazolyl)-N,N,N',N'-tetramethyluronium hexafluorophosphate (614 mg, 1.63 mmol), 5,6,7,8-tetrahydroimidazo[1,2-a]pyrazine 4c (200 mg, 1.63 mmol) and N,N-diisopropylethylamine (0.4 mL, 2.16 mmol). After stirring for 12 hours, the reaction mixture was concentrated under reduced pressure and the resulting residue was purified by thin layer chromatography with elution system A to obtain 4-[[3-(6,8-dihydro-5H-imidazo[1,2-a]pyrazine-7-carbonyl)-4-fluoro-phenyl]methyl]-2H-phthalazin-1-one 4 (10 mg, yield 2.3%) as a white solid.

MS m/z (ESI): 404.1 [M+1]

$^1$H NMR (400 MHz, CDCl$_3$): δ 10.07 (br. s, 1H), 8.53 (d, 1H), 7.96 (m, 1H), 7.83 (m, 3H), 7.51 (m, 1H), 7.30 (m, 2H), 6.01 (t, 1H), 4.73 (d, 2H), 4.35 (s, 2H), 1.60 (m, 2H), 1.34 (m, 2H)

Example 5

4-[[4-fluoro-3-[3-(trifluoromethyl)-6,8-dihydro-5H-imidazo[1,5-a]pyrazine-7-carbonyl]phenyl]methyl]-2H-phthalazin-1-one

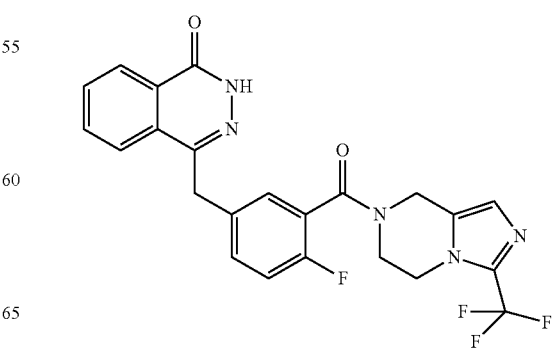

33
-continued

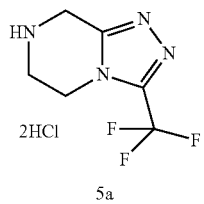

5a

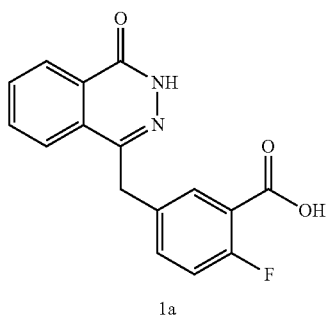

1a

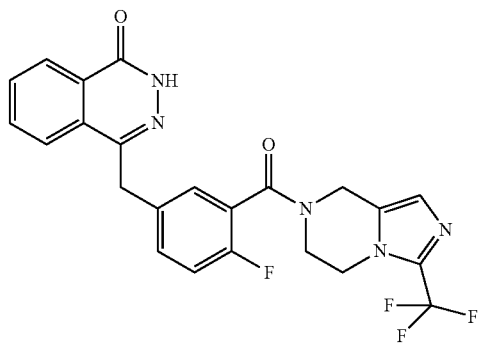

5

2-Fluoro-5-[(4-oxo-3H-phthalazin-1-yl)methyl]benzoic acid 1a (500 mg, 1.68 mmol) was dissolved in 5 mL of N,N-dimethylformamide, followed by addition of O-(1-benzotriazolyl)-N,N,N',N'-tetramethyluronium hexafluorophosphate (955 mg, 2.52 mmol), 3-trifluoromethyl-5,6,7,8-tetraahydroimidazo[1,5-a]pyrazine hydrochloride 5a (457 mg, 2 mmol, prepared according to a known method disclosed by "patent application WO2009082881") and N,N-diisopropylethylamine (0.6 mL, 3.36 mmol). After stirring for 12 hours, the reaction mixture was concentrated under reduced pressure and the resulting residue was purified by thin layer chromatography with elution system A to obtain 4-[[4-fluoro-3-[3-(trifluoromethyl)-6,8-dihydro-5H-imidazo[1,5-a]pyrazine-7-carbonyl]phenyl]methyl]-2H-phthalazin-1-one 5 (400 mg, yield 50.5%) as a white solid.

MS m/z (ESI): 472.1 [M+1]

¹H NMR (400 MHz, CDCl₃): δ 10.81 (br. s, 1H), 8.49 (m, 1H), 7.79 (m, 3H), 7.42 (m, 2H), 7.08 (m, 1H), 5.00 (m, 1H), 4.64 (m, 1H), 4.32 (m, 2H), 4.16 (m, 3H), 3.75 (m, 1H), 3.49 (s, 1H)

34
Example 6

4-[[4-fluoro-3-[1-(hydroxymethyl)-3-(trifluoromethyl)-6,8-dihydro-5H-imidazo[1,5-a]pyrazine-7-carbonyl]phenyl]methyl]-2H-phthalazin-1-one

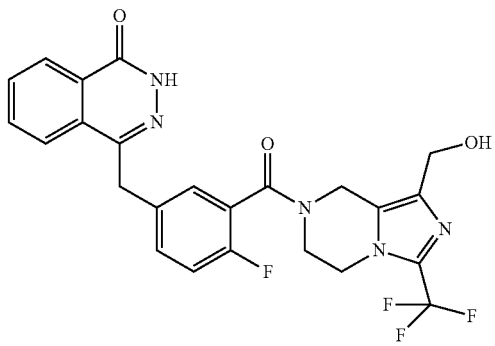

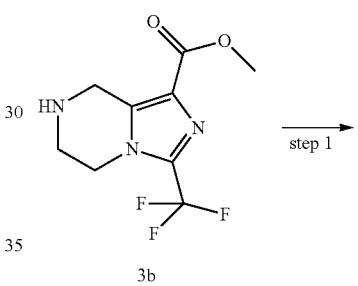

3b

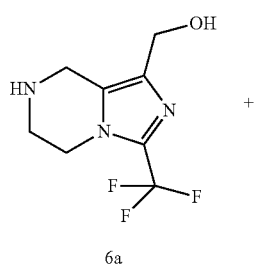

6a

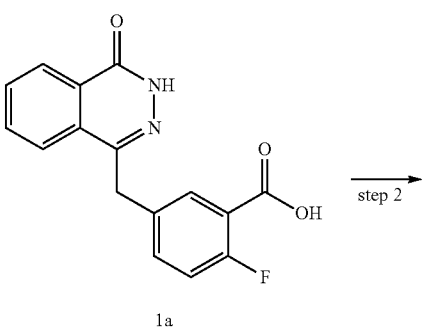

1a step 1 step 2

-continued

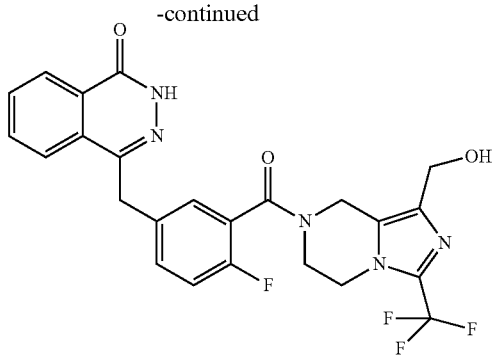

6

Step 1

[3-(trifluoromethyl)-5,6,7,8-tetrahydroimidazo[1,5-a]pyrazin-1-yl]methanol

Methyl 3-(trifluoromethyl)-5,6,7,8-tetrahydroimidazo[1,5-a]pyrazine-1-carboxylate 3b (315 mg, 1.26 mmol) was dissolved in 10 mL of ethanol, followed by addition of sodium borohydride (240 mg, 6.33 mmol). After stirring for 12 hours, the reaction mixture was added dropwise with 2 M hydrochloric acid until no gas was generated in the reaction mixture. The reaction mixture was concentrated under reduced pressure to obtain the crude [3-(trifluoromethyl)-5,6,7,8-tetrahydroimidazo[1,5-a]pyrazin-1-yl]methanol 6a (230 mg) as a white solid. The product was used directly in the next reaction without purification.

Step 2

4-[[4-fluoro-3-[1-(hydroxymethyl)-3-(trifluoromethyl)-6,8-dihydro-5H-imidazo[1,5-a]pyrazine-7-carbonyl]phenyl]methyl]-2H-phthalazin-1-one 2-Fluoro-5-[(4-oxo-3H-phthalazin-1-yl)methyl]benzoic acid 1a (372 mg, 1.25 mmol) was dissolved in 5 mL of N,N-dimethylformamide, followed by addition of N-hydroxybenzotriazole (85 mg, 0.63 mmol), [3-(trifluoromethyl)-5,6,7,8-tetrahydroimidazo[1,5-a]pyrazin-1-yl]methanol 6a (277 mg, 1.25 mmol), 1-ethyl-(3-dimethylaminopropyl) carbodiimide hydrochloride (359 mg, 1.88 mmol) and triethylamine (0.3 mL, 2.5 mmol). After stirring for 12 hours, the reaction mixture was concentrated under reduced pressure and the resulting residue was purified by thin layer chromatography with elution system A to obtain 4-[[4-fluoro-3-[1-(hydroxymethyl)-3-(trifluoromethyl)-6,8-dihydro-5H-imidazo[1,5-a]pyrazine-7-carbonyl]phenyl]methyl]-2H-phthalazin-1-one 6 (400 mg, yield 64.0%) as a white solid.

MS m/z (ESI): 502.2 [M+1]

$^{1}$H NMR (400 MHz, CDCl$_3$): δ 10.81 (br. s, 1H), 8.47 (s, 1H), 7.83-7.75 (m, 3H), 7.42-7.36 (m, 2H), 7.14-7.12 (m, 1H), 5.31 (s, 1H), 5.04 (s, 1H), 4.69 (d, 1H), 4.50 (s, 1H), 4.32-4.25 (m, 4H), 4.16-4.10 (m, 1H), 2.05 (s, 1H)

Example 7

N-ethyl-7-[2-fluoro-5-[(4-oxo-3H-phthalazin-1-yl)methyl]benzoyl]-3-(trifluoromethyl)-6,8-dihydro-5H-imidazo[1,5-a]pyrazine-1-carboxamide

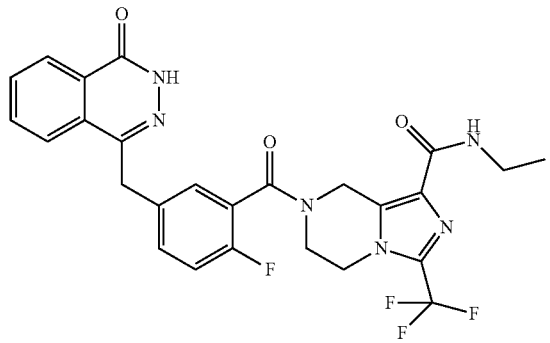

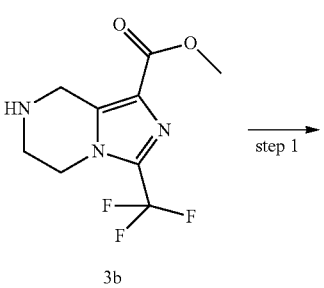

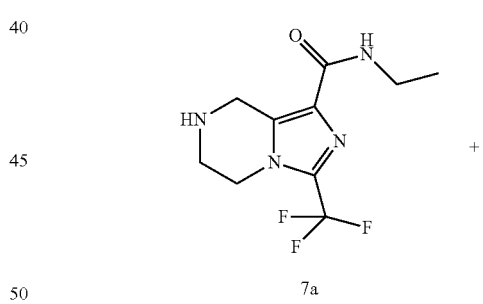

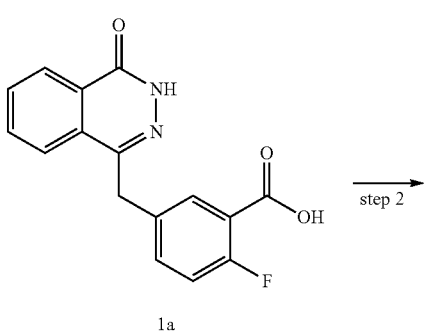

37
-continued

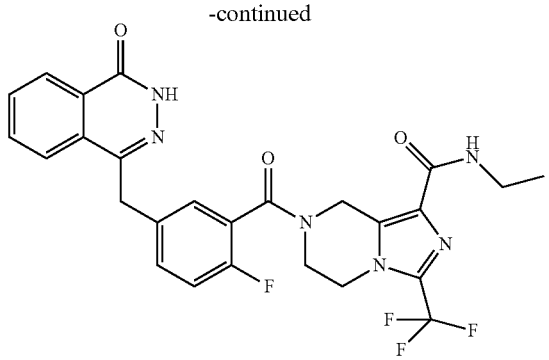

7

Step 1

N-ethyl-3-(trifluoromethyl)-5,6,7,8-tetrahydroimidazo[1,5-a]pyrazine-1-carboxamide Methyl 3-(trifluoromethyl)-5,6,7,8-tetrahydroimidazo[1,5-a]pyrazine-1-carboxylate 3b (1 g, 4 mmol) was dissolved in 40 mL of ethylamine solution (60%). After stirring at 50° C. for 12 hours, the reaction mixture was concentrated under reduced pressure to obtain the crude N-ethyl-3-(trifluoromethyl)-5,6,7,8-tetrahydroimidazo[1,5-a]pyrazine-1-carboxamide 7a (1.15 g) as a white solid. The product was used directly in the next reaction without purification.

MS m/z (ESI): 263.1 [M+1]

Step 2

N-ethyl-7-[2-fluoro-5-[(4-oxo-3H-phthalazin-1-yl)methyl]benzoyl]-3-(trifluoromethyl)-6,8-dihydro-5H-imidazo[1,5-a]pyrazine-1-carboxamide 2-Fluoro-5-[(4-oxo-3H-phthalazin-1-yl)methyl]benzoic acid 1a (250 mg, 0.84 mmol) was dissolved in 20 mL of N,N-dimethylformamide, followed by addition of O-(1-benzotriazolyl)-N,N,N',N'-tetramethyluronium hexafluorophosphate (480 mg, 1.26 mmol), crude N-ethyl-3-(trifluoromethyl)-5,6,7,8-tetrahydroimidazo[1,5-a]pyrazine-1-carboxamide 7a (242 mg, 0.92 mmol) and N,N-diisopropylethylamine (0.3 mL, 1.68 mmol). After stirring for 12 hours, the reaction mixture was added with 50 mL of $H_2O$, and extracted with dichloromethane (50 mL×3). The organic phase was combined, concentrated under reduced pressure, added with 100 mL of ethyl acetate, washed successively with saturated sodium bicarbonate solution (40 mL), saturated sodium chloride solution (40 mL), dried over anhydrous sodium sulfate and filtered. The filtrate was concentrated under reduced pressure and the resulting residue was purified by thin layer chromatography with elution system A to obtain N-ethyl-7-[2-fluoro-5-[(4-oxo-3H-phthalazin-1-yl)methyl]benzoyl]-3-(trifluoromethyl)-6,8-dihydro-5H-imidazo[1,5-a]pyrazine-1-carboxamide 7 (200 mg, yield 43.9%) as a white solid.

MS m/z (ESI): 543.2 [M+1]

$^1$H NMR (400 MHz, CDCl$_3$): δ 11.38 (br. s, 1H), 8.47 (m, 1H), 7.84 (m, 3H), 7.37 (m, 2H), 7.19 (m, 1H), 5.10 (s, 2H), 4.30 (s, 2H), 4.29 (m, 4H), 3.47 (m, 2H), 1.27 (m, 3H)

38
Example 8

7-[2-fluoro-5-[(4-oxo-3H-phthalazin-1-yl)methyl]benzoyl]-3-(trifluoromethyl)-6,8-dihydro-5H-imidazo[1,5-a]pyrazine-1-carboxylic acid

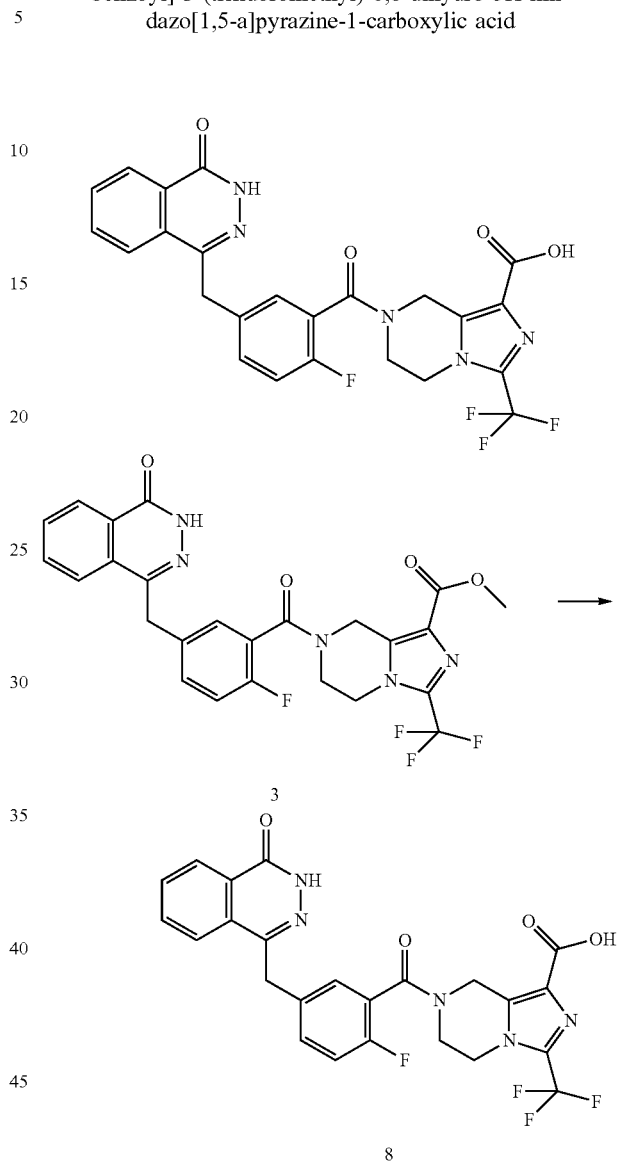

Methyl 7-[2-fluoro-5-[(4-oxo-3H-phthalazin-1-yl)methyl]benzoyl]-3-(trifluoromethyl)-6,8-dihydro-5H-imidazo[1,5-a]pyrazine-1-carboxylate 3 (30 mg, 0.057 mmol) was dissolved in 1.5 mL of a mixed solvent of tetrahydrofuran, methanol and water (V/V/V=1:1:1), followed by addition of sodium hydroxide (10 mg, 0.25 mmol). After stirring for 12 hours, concentrated hydrochloric acid was added dropwise to the reaction mixture until the pH was 2. The reaction mixture was extracted with dichloromethane (15 mL×2). The organic phase was combined, dried over anhydrous sodium sulfate and filtered. The filtrate was concentrated under reduced pressure and the resulting residue was purified by thin layer chromatography with elution system A to obtain 7-[2-fluoro-5-[(4-oxo-3H-phthalazin-1-yl)methyl]benzoyl]-3-(trifluoromethyl)-6,8-dihydro-5H-imidazo[1,5-a]pyrazine-1-carboxylic acid 8 (10 mg, yield 34.4%) as a light yellow solid.

MS m/z (ESI): 516.5 [M+1]

¹H NMR (400 MHz, CD₃OD): δ 8.36 (d, 1H), 7.93 (d, 1H), 7.83 (m, 2H), 7.60 (d, 1H), 7.29 (m, 1H), 6.97 (t, 1H), 4.32 (s, 2H), 3.41 (m, 6H)

Example 9

4-[[4-fluoro-3-[1-(methylaminomethyl)-3-(trifluoromethyl)-6,8-dihydro-5H-imidazo[1,5-a]pyrazine-7-carbonyl]phenyl]methyl]-2H-phthalazin-1-one

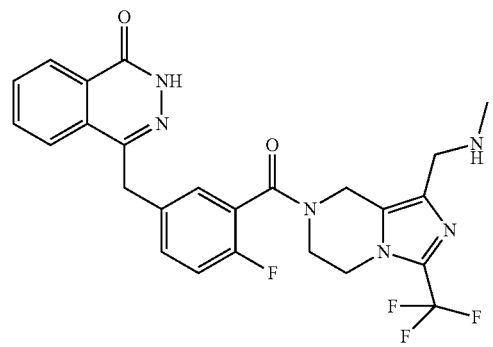

6

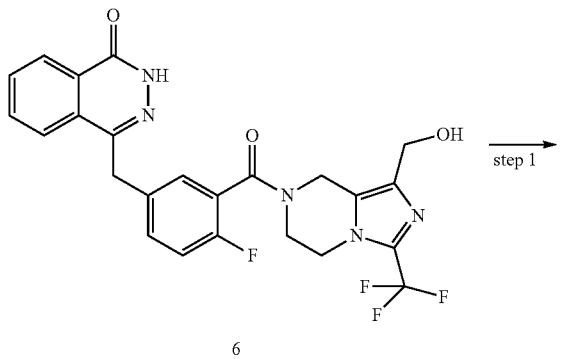

step 1

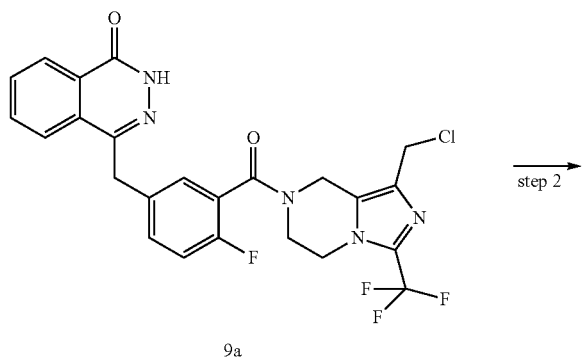

9a step 2

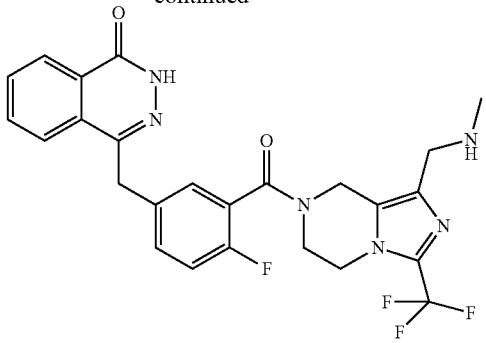

9

Step 1

4-[[3-[1-(chloromethyl)-3-(trifluoromethyl)-6,8-dihydro-5H-imidazo[1,5-a]pyrazine-7-carbonyl]-4-fluoro-phenyl]methyl]-2H-phthalazin-1-one 4-[[4-Fluoro-3-[1-(hydroxy methyl)-3-(trifluoromethyl)-6,8-dihydro-5H-imidazo[1, 5-a]pyrazine-7-carbonyl]phenyl]methyl]-2H-phthalazin-1-one 6 (200 mg, 0.40 mmol) was dissolved in 5 mL of thionyl chloride. The reaction mixture was heated to reflux for 4 hours. The reaction mixture was concentrated under reduced pressure, added with 10 mL of H₂O, extracted with dichloromethane (10 mL×3). The organic phase was combined, dried over anhydrous sodium sulfate and filtered. The filtrate was concentrated under reduced pressure to obtain 4-[[3-[1-(chloromethyl)-3-(trifluoromethyl)-6,8-dihydro-5H-imidazo[1,5-a]pyrazine-7-carbonyl]-4-fluoro-phenyl]methyl]-2H-phthalazin-1-one 9a (200 mg, yield 96.6%) as a yellow solid.

MS m/z (ESI): 520.1 [M+1]

Step 2

4-[[4-fluoro-3-[1-(methylaminomethyl)-3-(trifluoromethyl)-6,8-dihydro-5H-imidazo[1,5-a]pyrazine-7-carbonyl]phenyl]methyl]-2H-phthalazin-1-one 4-[[3-[1-(Chloromethyl)-3-(trifluoromethyl)-6,8-dihydro-5H-imidazo[1,5-a]pyrazine-7-carbonyl]-4-fluoro-phenyl]methyl]-2H-phthalazin-1-one 9a (372 mg, 1.25 mmol) was dissolved in 5 mL of acetonitrile, followed by addition of 0.6 mL of a 2 M solution of methylamine in tetrahydrofuran and potassium carbonate (159 mg, 1.15 mmol). The reaction mixture was heated to reflux for 6 hours. The reaction mixture was filtered. The filtrate was concentrated under reduced pressure and was purified by thin layer chromatography with elution system A to obtain 4-[[4-fluoro-3-[1-(methylaminomethyl)-3-(trifluoromethyl)-6,8-dihydro-5H-imidazo[1,5-a]pyrazine-7-carbonyl]phenyl]methyl]-2H-phthalazin-1-one 9 (20 mg, yield 10.1%) as a yellow solid.

MS m/z (ESI): 515.2 [M+1]

¹H NMR (400 MHz, CDCl₃): δ 11.87 (br. s, 1H), 8.35-8.42 (m, 1H), 7.72-7.81 (m, 3H), 7.35-7.43 (m, 1H), 6.96-7.06 (m, 1H), 5.01-5.02 (m, 1H), 3.99-4.28 (m, 6H), 3.71-3.72 (m, 1H), 3.47 (s, 1H), 2.74 (d, 3H), 2.03-2.05 (m, 1H)

Example 10

7-[2-fluoro-5-[(4-oxo-3H-phthalazin-1-yl)methyl]benzoyl]-3-(trifluoromethyl)-6,8-dihydro-5H-imidazo[1,5-a]pyrazine-1-carboxamide

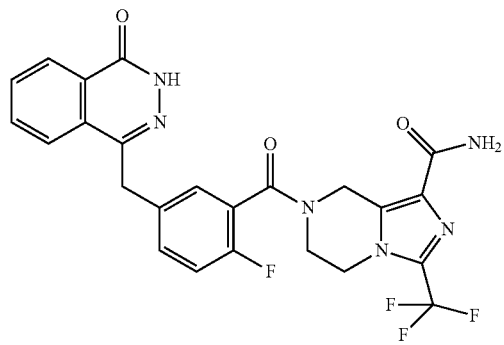

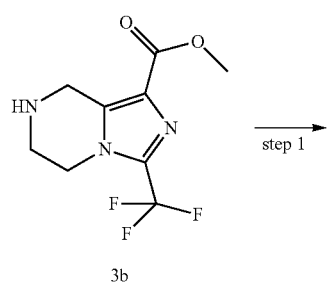

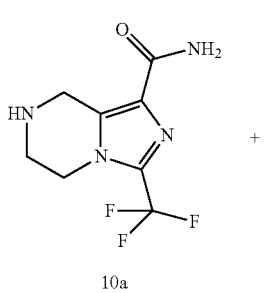

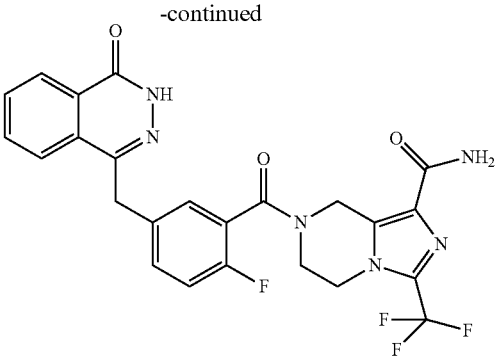

Step 1

3-(trifluoromethyl)-5,6,7,8-tetrahydroimidazo[1,5-a]pyrazine-1-carboxamide

Methyl 3-(trifluoromethyl)-5,6,7,8-tetrahydroimidazo[1,5-a]pyrazine-1-113 carboxylate 3b (250 mg, 1 mmol) and 10 mL of ammonium hydroxide were added in a 20 mL sealed tube. The reaction mixture was heated to 100° C. and reacted for 3 hours. The reaction mixture was concentrated under reduced pressure to obtain crude 3-(trifluoromethyl)-5,6,7,8-tetrahydroimidazo[1,5-a]pyrazine-1-carboxamide 10a (240 mg) as a white solid. The product was used directly in the next reaction without purification.

MS m/z (ESI): 235.1 [M+1]

Step 2

7-[2-fluoro-5-[(4-oxo-3H-phthalazin-1-yl)methyl]benzoyl]-3-(trifluoromethyl)-6,8-dihydro-5H-imidazo[1,5-a]pyrazine-1-carboxamide 2-Fluoro-5-[(4-oxo-3H-phthalazin-1-yl)methyl]benzoic acid 1a (150 mg, 0.50 mmol) was dissolved in 10 mL of N,N-dimethylformamide, followed by addition of O-(1-benzotriazolyl)-N,N,N',N'-tetramethyluronium hexafluorophosphate (285 mg, 0.75 mmol), crude 3-(trifluoromethyl)-5,6,7,8-tetrahydroimidazo[1,5-a]pyrazine-1-carboxamide 10a (130 mg, 0.55 mmol) and N, N-diisopropylethylamine (0.2 mL, 1 mmol). After stirring for 12 hours, the reaction mixture was added with 50 mL of $H_2O$ and extracted with dichloromethane (60 mL×3). The organic phase was combined, concentrated under reduced pressure, added with 100 mL of ethyl acetate, washed successively with $H_2O$ (40 mL) and saturated sodium chloride solution (40 mL), dried over anhydrous sodium sulfate and filtered. The filtrate was concentrated under reduced pressure and the resulting residue was purified by thin layer chromatography with elution system A to obtain 7-[2-fluoro-5-[(4-oxo-3H-phthalazin-1-yl)methyl]benzoyl]-3-(trifluoromethyl)-6,8-dihydro-5H-imidazo[1,5-a]pyrazine-1-carboxamide 10 (50 mg, yield 20.0%) as a white solid.

MS m/z (ESI): 515.1 [M+1]

$^1$H NMR (400 MHz, $CDCl_3$): δ 8.49 (m, 1H), 7.85 (m, 3H), 7.33 (m, 2H), 7.15 (m, 1H), 5.07 (s, 2H), 4.30 (s, 2H), 4.23 (m, 4H)

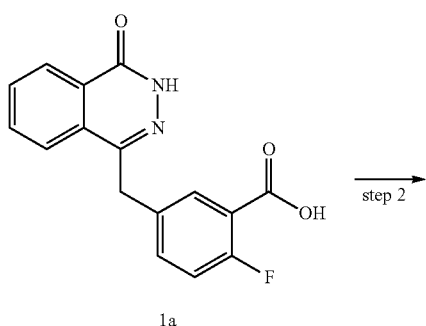

Example 11

4-[[3-[1-bromo-3-(trifluoromethyl)-6,8-dihydro-5H-imidazo[1,5-a]pyrazine-7-carbonyl]-4-fluoro-phenyl]methyl]-2H-phthalazin-1-one

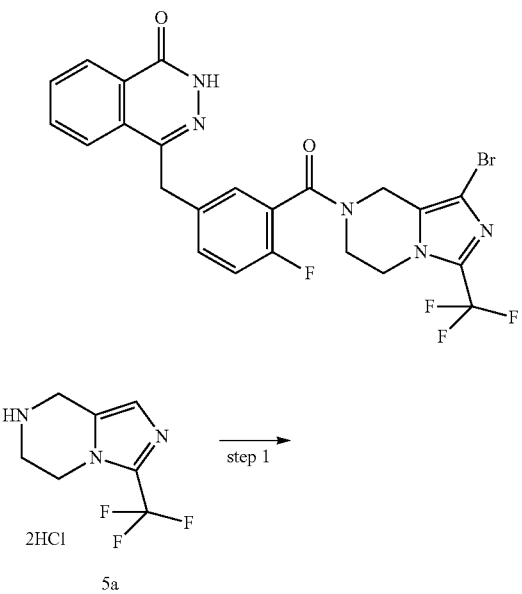

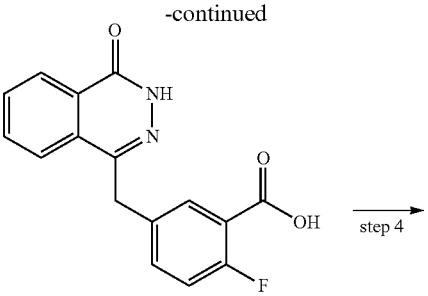

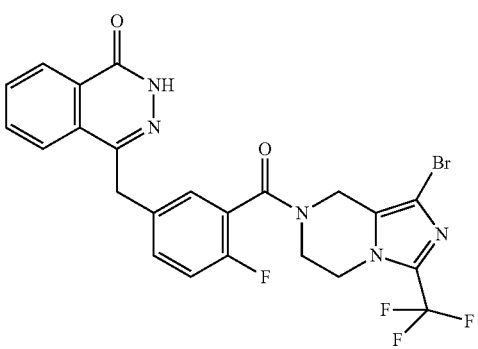

Step 1 tert-butyl 3-(trifluoromethyl)-6,8-dihydro-5H-imidazo[1,5-a]pyrazine-7-carboxylate 3-(Trifluoromethyl)-5,6,7,8-tetrahydroimidazo[1,5-a]pyrazine hydrochloride 5a (2.20 g, 8.30 mmol) was dissolved in 20 mL of dichloromethane, followed by addition of triethylamine (4.6 mL, 33.20 mmol) and di-tert-butyl dicarbonate (2.70 g, 12.50 mmol). After stirring for 12 hours, the reaction mixture was added with 50 mL of $H_2O$, extracted with dichloromethane (50 mL×3). The organic phase was combined, washed successively with saturated ammonium chloride solution (40 mL) and saturated sodium chloride solution (40 mL), dried over anhydrous sodium sulfate and filtered. The filtrate was concentrated under reduced pressure to obtain tert-butyl 3-(trifluoromethyl)-6,8-dihydro-5H-imidazo[1,5-a]pyrazine-7-carboxylate 11a (2.20 g, yield 91.7%) as a light brown solid.

MS m/z (ESI): 292.1 [M+1]

Step 2 tert-butyl 1-bromo-3-(trifluoromethyl)-6,8-dihydro-5H-imidazo[1,5-a]pyrazine-7-carboxylate Tert-butyl 3-(trifluoromethyl)-6,8-dihydro-5H-imidazo[1,5-a]pyrazine-7-carboxylate 11a (370 mg, 1.27 mmol) was dissolved in 30 mL of tetrahydrofuran, followed by addition of N-bromosuccinimide (453 mg, 2.54 mmol) under −78° C. After stirring for 1 hour, the reaction mixture was heated to room temperature and reacted for 12 hours. The reaction mixture was added with 50 mL of $H_2O$, extracted with ethyl acetate (60 mL×3). The organic phase was combined, washed with saturated sodium chloride solution (40 mL), dried over anhydrous sodium sulfate and filtered. The filtrate was concentrated under reduced pressure to obtain crude tert-butyl 1-bromo-3-(trifluoromethyl)-6,8-dihydro-5H-imidazo[1,5-a]pyrazine-7-carboxylate 11b (510 mg) as a light yellow oil. The product was used directly in the next reaction without purification.

MS m/z (ESI): 372.0 [M+1]

Step 3

1-bromo-3-(trifluoromethyl)-5,6,7,8-tetrahydroimidazo[1,5-a]pyrazine hydrochloride Crude tert-butyl 1-bromo-3-(trifluoromethyl)-6,8-dihydro-5H-imidazo[1,5-a]pyrazine-7-carboxylate 11b (470 mg, 1.27 mmol) was dissolved in 50 mL of a 2 M solution of hydrogen chloride in 1,4-dioxane. After stirring for 4 hours, the reaction mixture was concentrated under reduced pressure to obtain 1-bromo-3-(trifluoromethyl)-5,6,7,8-tetrahydroimidazo[1,5-a]pyrazine hydrochloride 11c (220 mg, yield 56.5%) as a light yellow oil.

Step 4

4-[[3-[1-bromo-3-(trifluoromethyl)-6,8-dihydro-5H-imidazo[1,5-a]pyrazine-7-carbonyl]-4-fluoro-phenyl]methyl]-2H-phthalazin-1-one 2-Fluoro-5-[(4-oxo-3H-phthalazin-1-yl)methyl]benzoic acid 1a (210 mg, 0.70 mmol) was dissolved in 30 mL of N,N-dimethylformamide, followed by addition of O-(1-N,N,N',N'-tetramethyluronium hexafluorophosphate (360 mg, 0.95 mmol), 1-bromo-3-(trifluoromethyl)-5,6,7,8-tetrahydroimidazo[1,5-a]pyrazine hydrochloride 11c (214 mg, 0.70 mmol) and N, N-diisopropylethylamine (0.4 mL, 2.10 mmol). After stirring for 12 hours, the reaction mixture was added with 50 mL of H₂O, extracted with dichloromethane (80 mL×3). The organic phase was combined, concentrated under reduced pressure, added with 100 mL of ethyl acetate, washed successively with saturated sodium carbonate solution (40 mL), H₂O (40 mL) and saturated sodium chloride solution (40 mL), dried over anhydrous sodium sulfate and filtered. The filtrate was concentrated under reduced pressure and the resulting residue was purified by thin layer chromatography with elution system A to obtain 4-[[3-[1-bromo-3-(trifluoromethyl)-6,8-dihydro-5H-imidazo[1,5-a]pyrazine-7-carbonyl]-4-fluoro-phenyl]methyl]-2H-phthalazin-1-one 11 (185 mg, yield 48.0%) as a white solid.

MS m/z (ESI): 552.0 [M+1]

¹H NMR (400 MHz, CDCl₃): δ 8.48 (m, 1H), 7.73 (m, 3H), 7.31 (m, 2H), 7.11 (m, 1H), 4.89 (s, 2H), 4.49 (s, 2H), 4.48 (m, 4H)

Example 12

4-[[4-fluoro-3-[2-(trifluoromethyl)-6,8-dihydro-5H-imidazo[1,2-a]pyrazine-7-carbonyl]phenyl]methyl]-2H-phthalazin-1-one

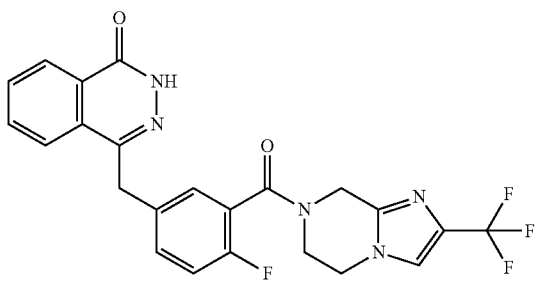

Step 1

2-(trifluoromethyl)imidazo[1,2-a]pyrazine

Pyrazin-2-amine 4a (5.25 g, 55.20 mmol) was dissolved in 120 mL of ethanol, followed by addition of 3-bromo-1,1,1-trifluoro-propan-2-one 12a (5.7 mL, 55.20 mmol). The reaction mixture was heated to reflux for 16 hours. The reaction mixture was concentrated under reduced pressure, added with 100 mL of ethyl acetate and 100 mL of saturated sodium bicarbonate solution and separated. The aqueous phase was extracted with ethyl acetate (50 mL×3). The organic phase was combined, washed with saturated sodium chloride solution (50 mL), dried over anhydrous sodium sulfate and filtered. The filtrate was concentrated under reduced pressure and the resulting residue was purified by silica gel column chromatography with elution system B to obtain 2-(trifluoromethyl)imidazo[1,2-a]pyrazine 12b (2.40 g, yield 22.8%) as a yellow solid.

MS m/z (ESI): 188.0 [M+1]

Step 2

2-(trifluoromethyl)-5,6,7,8-tetrahydroimidazo[1,2-a]pyrazine 2-(Trifluoromethyl)imidazo[1,2-a]pyrazine 12b (2.40 g, 12.55 mmol) was dissolved in 100 mL of methanol, followed by addition of Pd—C (10%, 480 mg), and the reactor was purged with hydrogen for three times. After stirring for 12 hours, the reaction mixture was filtered and the filter cake was washed with methanol. The filtrate was concentrated under reduced pressure to obtain 2-(trifluoromethyl)-5,6,7,8-tetrahydroimidazo[1,2-a]pyrazine 12c (2.30 g, yield 95.8%) as a yellow oil.

Step 3

4-[[4-fluoro-3-[2-(trifluoromethyl)-6,8-dihydro-5H-imidazo[1,2-a]pyrazine-7-carbonyl]phenyl]methyl]-2H-phthalazin-1-one 2-Fluoro-5-[(4-oxo-3H-phthalazin-1-yl)methyl]benzoic acid 1a (500 mg, 1.68 mmol) was dissolved in 10 mL of N,N-dimethylformamide, followed by addition of O-(1-benzotriazolyl)-N,N,N',N'-tetramethyluronium hexafluorophosphate (830 mg, 2.52 mmol), 2-(trifluoromethyl)-5,6,7,8-tetrahydroimidazo[1,2-a]pyrazine 12c (384 mg, 2 mmol) and N, N-diisopropylethylamine (1 mL, 5 mmol). After stirring for 12 hours, the resulting residue was purified by silica gel column chromatography with elution system A to obtain 4-[[4-fluoro-3-[2-(trifluoromethyl)-6,8-dihydro-5H-imidazo[1,2-a]pyrazine-7-carbonyl]phenyl]methyl]-2H-phthalazin-1-one 12 (200 mg, yield 25.0%) as a white solid.

MS m/z (ESI): 472.1[M+1]

$^1$H NMR (400 MHz, CDCl$_3$): δ 10.29 (br. s, 1H), 8.47 (m, 1H), 7.80 (m, 3H), 7.37 (m, 2H), 7.25 (m, 1H), 6.50 (m, 1H), 4.67 (s, 2H), 4.28 (m, 2H), 4.14 (m, 2H), 3.73 (m, 2H)

Example 13

7-[2-fluoro-5-[(4-oxo-3H-phthalazin-1-yl)methyl]benzoyl]-N-methyl-3-(trifluoromethyl)-6,8-dihydro-5H-imidazo[1,5-a]pyrazine-1-carboxamide

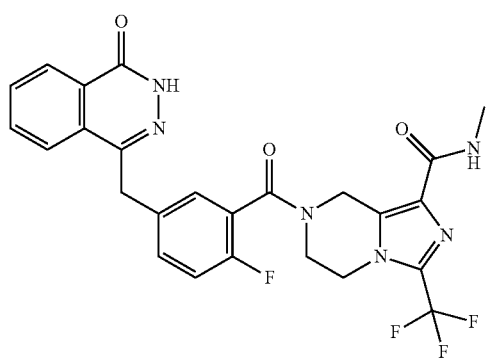

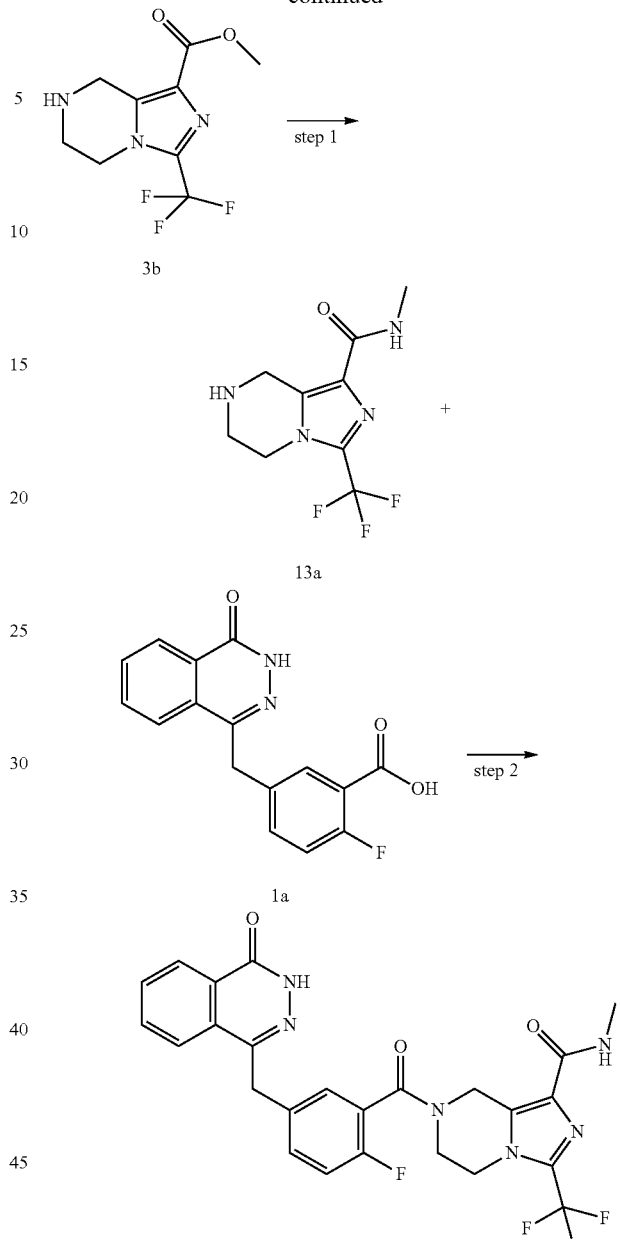

Step 1

N-methyl-3-(trifluoromethyl)-5,6,7,8-tetrahydroimidazo[1,5-a]pyrazine-1-carboxamide Methyl 3-(trifluoromethyl)-5,6,7,8-tetrahydroimidazo[1,5-a]pyrazine-1-carboxylate 3b (500 mg, 2 mmol) was dissolved in 8 mL of methylamine solution (20% to 30%) was added in a 20 mL sealed tube. After stirring at 60° C. for 6 hours, the reaction mixture was concentrated under reduced pressure to obtain the crude N-methyl-3-(trifluoromethyl)-5,6,7,8-tetrahydroimidazo[1,5-a]pyrazine-1-carboxamide 13a (498 mg) as a white solid. The product was used directly in the next reaction without purification.

MS m/z (ESI): 249.1 [M+1]

Step 2

7-[2-fluoro-5-[(4-oxo-3H-phthalazin-1-yl)methyl]benzoyl]-N-methyl-3-(trifluoromethyl)-6,8-dihydro-5H-imidazo[1,5-a]pyrazine-1-carboxamide 2-Fluoro-5-[(4-oxo-3H-phthalazin-1-yl)methyl]benzoic acid 1a (598 mg, 2 mmol) was dissolved in 10 mL of N,N-dimethylformamide, followed by addition of 1-hydroxybenzotriazole (135 mg, 1 mmol), crude N-methyl-3-(trifluoromethyl)-5,6,7,8-tetrahydroimidazo[1,5-a]pyrazine-1-carboxamide 13a (498 mg, 2 mmol), 1-ethyl-(3-dimethylaminopropyl) carbodiimide hydrochloride (573 mg, 3 mmol) and N, N-diisopropylethylamine (774 mg, 6 mmol). After stirring for 12 hours, the reaction mixture was concentrated under reduced pressure, added with 30 mL of H₂O, extracted with ethyl acetate (50 mL×3). The organic phase was combined, dried over anhydrous sodium sulfate and filtered. The filtrate was concentrated under reduced pressure and the resulting residue was purified by thin layer chromatography with elution system A to obtain 7-[2-fluoro-5-[(4-oxo-3H-phthalazin-1-yl)methyl]benzoyl]-N-methyl-3-(trifluoromethyl)-6,8-dihydro-5H-imidazo[1,5-a]pyrazine-1-carboxamide 13 (650 mg, yield 61.0%) as a white solid.

MS m/z (ESI): 529.1 [M+1]

¹H NMR (400 MHz, CD₃OD): δ 8.36-8.34 (t, 1H), 7.96-7.94 (d, 1H), 7.86-7.81 (m, 2H), 7.50-7.45 (m, 2H), 7.22-7.15 (dd, 1H), 5.23 (s, 1H), 4.95 (s, 1H), 4.39 (d, 2H), 4.32 (d, 1H), 4.21 (s, 1H), 4.14 (s, 1H), 3.76 (s, 1H), 2.85 (d, 3H)

Example 14 ethyl 7-[2-fluoro-5-[(4-oxo-3H-phthalazin-1-yl)methyl]benzoyl]-6,8-dihydro-5H-imidazo[1,2-a]pyrazine-3-carboxylate

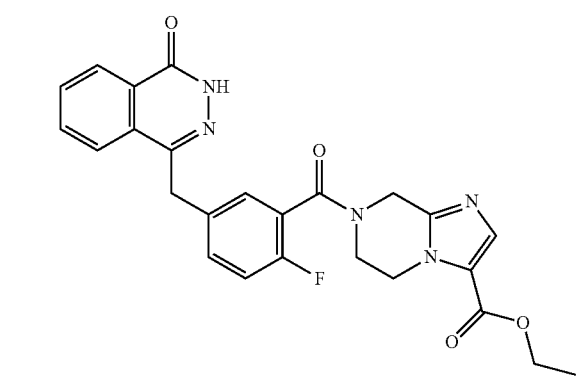

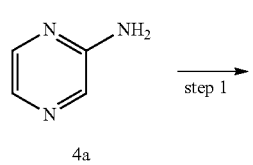

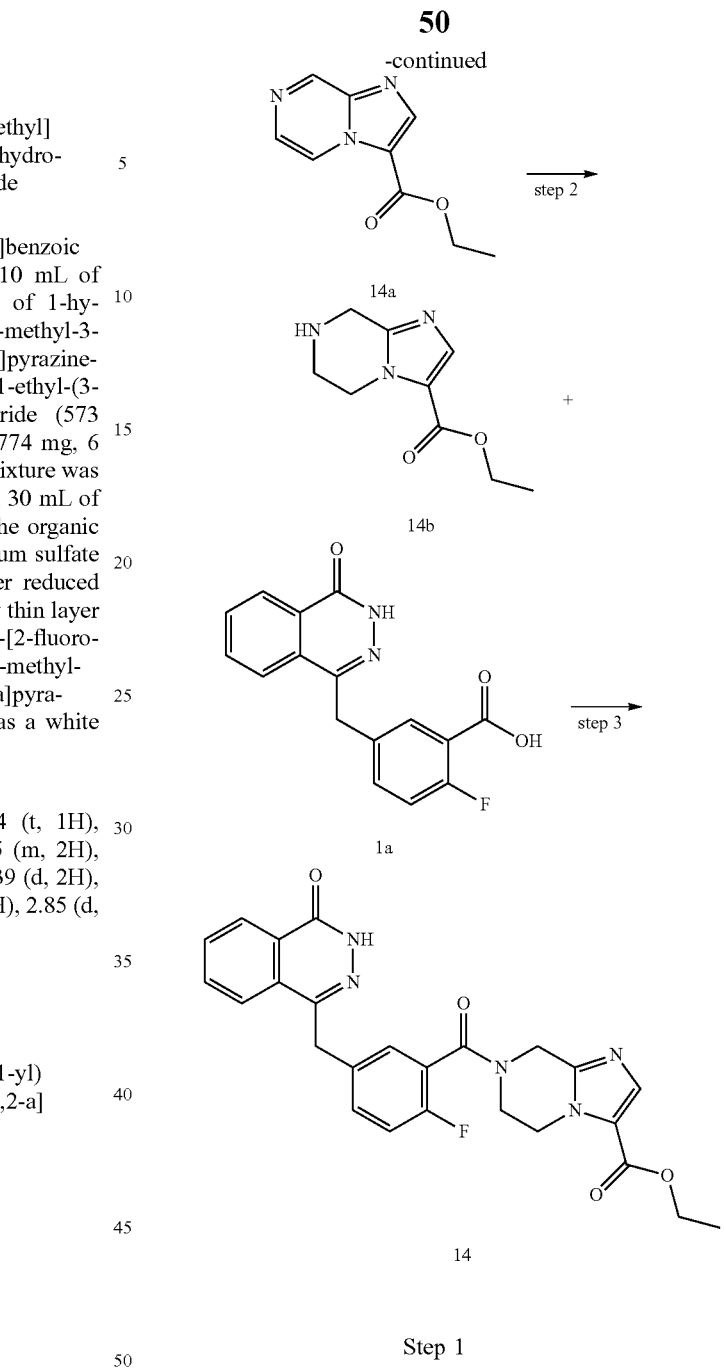

Step 1 ethyl imidazo[1,2-a]pyrazine-3-carboxylate

Pyrazin-2-amine 4a (1 g, 10 mmol) was dissolved in 50 mL of ethylene glycol dimethyl ether, followed by addition of 50 mL of methanol and 3-bromo-2-oxo-propionate (2.30 g, 12 mmol). After stirring for 4 hours at room temperature, the reaction mixture was cooled to 0° C. and stirred for 30 minutes until a solid precipitated. The reaction mixture was filtered, and the filter cake was washed with ether (10 mL×3). The solid was dissolved in 50 mL of anhydrous ethanol and the solution was refluxed for 4 hours. The reaction mixture was concentrated under reduced pressure, added with 100 mL of dichloromethane, washed successively with saturated sodium carbonate solution (40 mL) and saturated sodium chloride solution (40 mL), dried over anhydrous sodium sulfate and filtered. The filtrate was concentrated under reduced pressure to obtain ethyl imidazo[1,2-a]pyrazine-3-carboxylate 14a (0.55 g, yield 28.9%) as a brown solid.

MS m/z (ESI): 192.1 [M+1]

Step 2 ethyl 5,6,7,8-tetrahydroimidazo[1,2-a]pyrazine-3-carboxylate

Ethyl imidazo[1,2-a]pyrazine-3-carboxylate 14a (550 mg, 2.76 mmol) was dissolved in 30 mL of methanol, followed by addition of Pd—C (10%, 100 mg), and the reactor was purged with hydrogen for three times. After stirring for 3 hours, the reaction mixture was filtered and the filtrate was concentrated under reduced pressure to obtain ethyl 5,6,7,8-tetrahydroimidazo[1,2-a]pyrazine-3-carboxylate 14b (480 mg, yield 87.6%) as a yellow oil.

MS m/z (ESI): 196.1 [M+1]

Step 3 ethyl 7-[2-fluoro-5-[(4-oxo-3H-phthalazin-1-yl)methyl]benzoyl]-6,8-dihydro-5H-imidazo[1,2-a]pyrazine-3-carboxylate 2-Fluoro-5-[(4-oxo-3H-phthalazin-1-yl)methyl]benzoic acid 1a (300 mg, 1 mmol) was dissolved in 20 mL of N,N-dimethylformamide, followed by addition of O-(1-benzotriazolyl)-N,N,N',N'-tetramethyluronium hexafluorophosphate (570 mg, 1.50 mmol), ethyl 5,6,7,8-tetrahydroimidazo[1,2-a]pyrazine-3-carboxylate 14b (200 mg, 1 mmol) and N, N-diisopropylethylamine (0.3 mL, 2 mmol). After stirring for 12 hours, the reaction mixture was added with 50 mL of H₂O, extracted with dichloromethane (80 mL×3). The organic phase was combined, concentrated under reduced pressure, added with 100 mL of ethyl acetate, washed successively with saturated sodium carbonate solution (40 mL), H₂O (40 mL), saturated sodium chloride solution (40 mL), dried over anhydrous sodium sulfate and filtered. The filtrate was concentrated under reduced pressure and the resulting residue was purified by thin layer chromatography with elution system A to obtain ethyl 7-[2-fluoro-5-[(4-oxo-3H-phthalazin-1-yl)methyl]benzoyl]-6,8-dihydro-5H-imidazo[1,2-a]pyrazine-3-carboxylate 14 (280 mg, yield 58.6%) as a white solid.

MS m/z (ESI): 476.1 [M+1]

¹H NMR (400 MHz, CDCl₃): δ 10.53 (br. s, 1H), 8.46 (m, 1H), 7.76 (m, 3H), 7.59 (s, 1H), 7.36 (m, 2H), 7.08 (m, 1H), 4.69 (s, 2H), 4.37 (m, 2H), 4.31 (s, 2H), 4.27 (m, 4H), 1.26 (t, 3H)

Example 15

4-[[3-[3-(trifluoromethyl)-6,8-dihydro-5H-[1,2,4]triazolo[4,3-a]pyrazine-7-carbonyl]phenyl]methyl]-2H-phthalazin-1-one

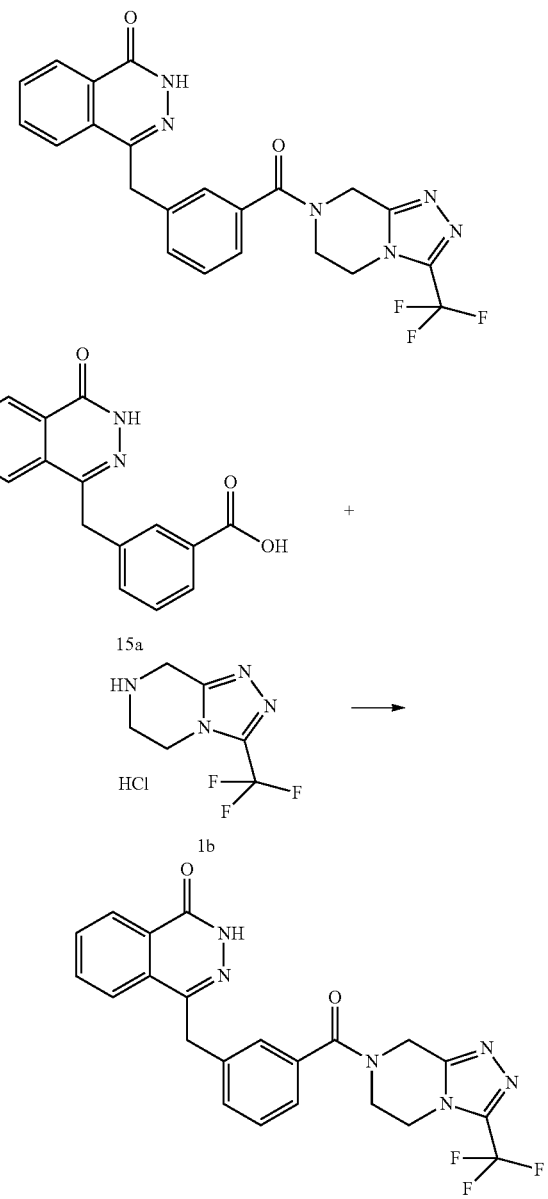

3-[(4-Oxo-3H-phthalazin-1-yl)methyl]benzoic acid 15a (300 mg, 1.07 mmol, prepared according to a known method disclosed by "patent application WO2004080976") was dissolved in 10 mL of N,N-dimethylformamide, followed by addition of O-(1-benzotriazolyl)-N,N,N',N'-tetramethyluronium hexafluorophosphate (730 mg, 1.93 mmol), 3-(trifluoromethyl)-5,6,7,8-tetrahydro-[1,2,4]triazolo[4,3-a]pyrazine hydrochloride 1b (269 mg, 1.40 mmol) and N, N-diisopropylethylamine (0.9 mL, 5.30 mmol). After stirring for 12 hours, the reaction mixture was added with 15 mL of H₂O, extracted with ethyl acetate (20 mL×3). The organic phase was combined, dried over anhydrous sodium sulfate and filtered. The filtrate was concentrated under reduced pressure and the resulting residue was purified by thin layer chromatography with elution system A to obtain 4-[[3-[3-(trifluoromethyl)-6,8-dihydro-5H-[1,2,4]triazolo[4,3-a]pyrazine-7-carbonyl]phenyl]methyl]-2H-phthalazin-1-one 15 (100 mg, yield 20.6%) as a white solid.

MS m/z (ESI): 455.1 [M+1]

$^1$H NMR (400 MHz, CDCl$_3$): δ 10.30 (br. s, 1H), 8.49 (d, 1H), 8.02 (m, 1H), 7.78 (m, 3H), 7.43 (m, 3H), 5.31 (s, 2H), 4.35 (s, 2H), 4.21 (m, 2H), 4.12 (m, 2H)

Example 16

4-[[3-(6,8-dihydro-5H-[1,2,4]triazolo[1,5-a]pyrazine-7-carbonyl)-4-fluoro-phenyl]methyl]-2H-phthalazin-1-one

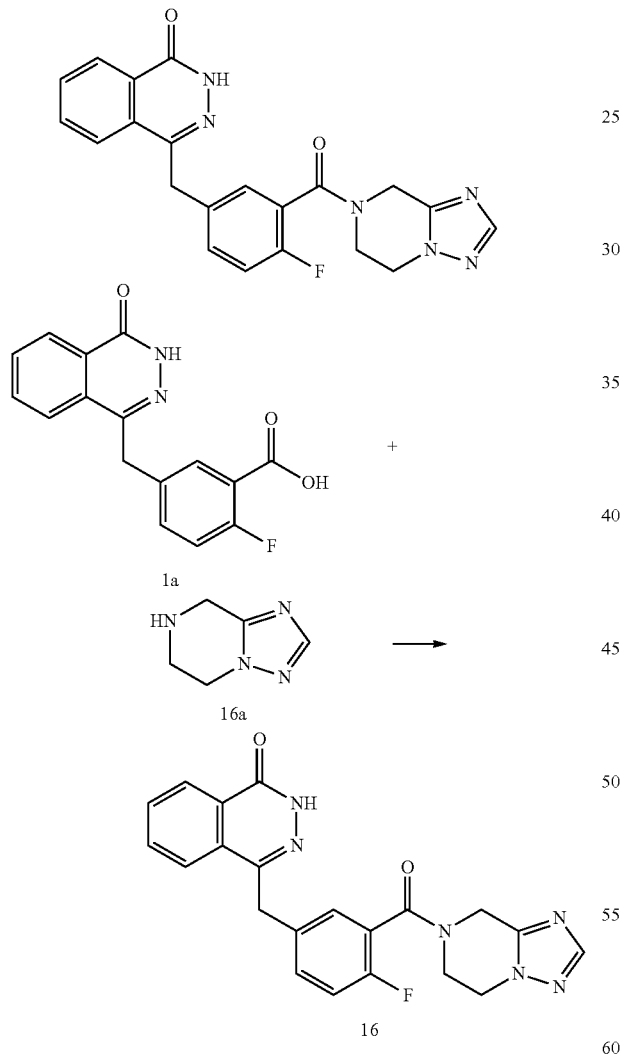

2-Fluoro-5-[(4-oxo-3H-phthalazin-1-yl)methyl]benzoic acid 1a (360 mg, 1.20 mmol) was dissolved in 10 mL of N,N-dimethylformamide, followed by addition of O-(1-benzotriazolyl)-N,N,N',N'-tetramethyluronium hexafluorophosphate (600 mg, 1.80 mmol), 5,6,7,8-tetrahydro-[1,2,4]triazolo[1,5-a]pyrazine 16a (150 mg, 1.20 mmol, prepared according to a known method disclosed by "patent application WO2009090055") and N, N-diisopropylethylamine (0.4 mL, 2.40 mmol). After stirring for 20 hours, the reaction mixture was concentrated under reduced pressure and the resulting residue was purified by thin layer chromatography with elution system A to obtain 4-[[3-(6,8-dihydro-5H-[1,2,4]triazolo[1,5-c]pyrazine-7-carbonyl)-4-fluoro-phenyl]methyl]-2H-phthalazin-1-one 16 (100 mg, yield 21.0%) as a yellow solid.

MS m/z (ESI): 405.1 [M+1]

$^1$H NMR (400 MHz, CDCl$_3$): δ 10.47 (br. s, 1H), 8.51-8.49 (m, 1H), 7.99-1.77 (m, 4H), 7.42-7.30 (m, 2H), 7.30-7.12 (m, 1H), 4.76 (m, 2H), 4.37-4.28 (m, 4H), 3.77-3.73 (m, 2H)

Example 17

4-[[3-(6,8-dihydro-5H-[1,2,4]triazolo[4,3-a]pyrazine-7-carbonyl)-4-fluoro-phenyl]methyl]-2H-phthalazin-1-one

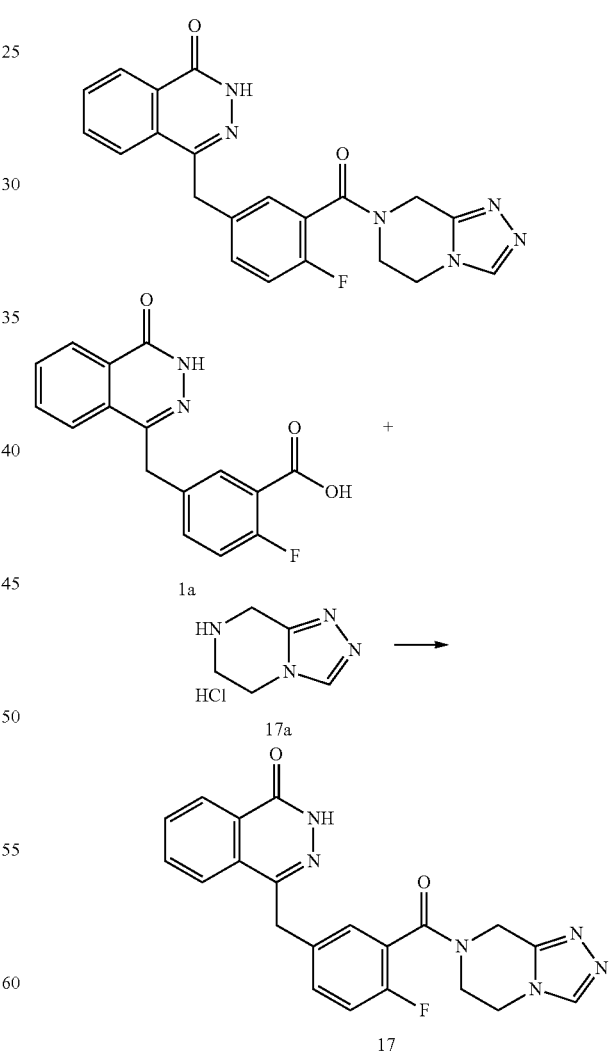

2-Fluoro-5-[(4-oxo-3H-phthalazin-1-yl)methyl]benzoic acid 1a (170 mg, 0.57 mmol) was dissolved in 10 mL of N,N-dimethylformamide, followed by addition of O-(1-N, N,N',N'-tetramethyluronium hexafluorophosphate (323 mg, 0.85 mmol), 5,6,7,8-tetrahydro-[1,2,4]triazolo[4,3-a]pyrazine hydrochloride 17a (100 mg, 0.63 mmol, prepared according to a known method "Journal of Medicinal Chemistry, 2005, 48(1), 141-151") and N, N-diisopropylethylamine (302 mg, 1.70 mmol). After stirring for 12 hours, the reaction mixture was concentrated under reduced pressure and the resulting residue was purified by thin layer chromatography with elution system A to obtain 4-[[3-(6,8-dihydro-5H-[1,2,4]triazolo[4,3-a]pyrazine-7-carbonyl)-4-fluorophenyl]methyl]-2H-phthalazin-1-one 17 (50 mg, yield 21.7%) as a light yellow solid.

MS m/z (ESI): 405.1 [M+1]

$^1$H NMR (400 MHz, CDCl$_3$): δ 10.87 (br. s, 1H), 8.46-8.45 (m, 1H), 8.18 (s, 1H), 7.80-7.76 (m, 3H), 7.40-7.38 (m, 2H), 7.12-7.07 (m, 1H), 4.79 (m, 2H), 4.31-4.20 (m, 4H), 3.75-3.62 (m, 2H)

Example 18

4-[[4-fluoro-3-[1-(pyrrolidine-1-carbonyl)-3-(trifluoromethyl)-6,8-dihydro-5H-imidazo[1,5-a]pyrazine-7-carbonyl]phenyl]methyl]-2H-phthalazin-1-one

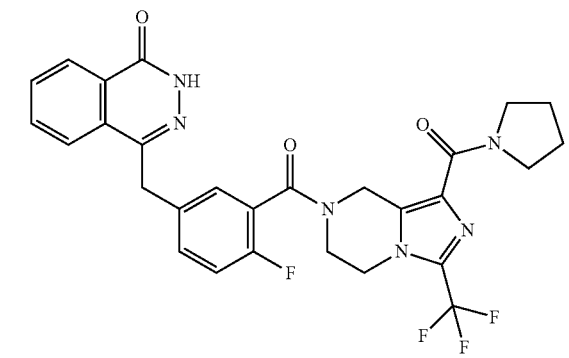

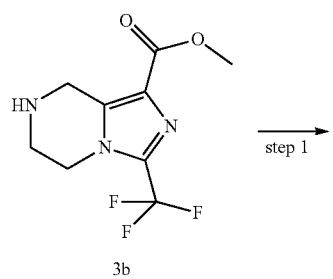

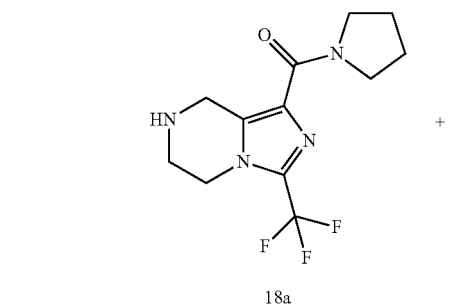

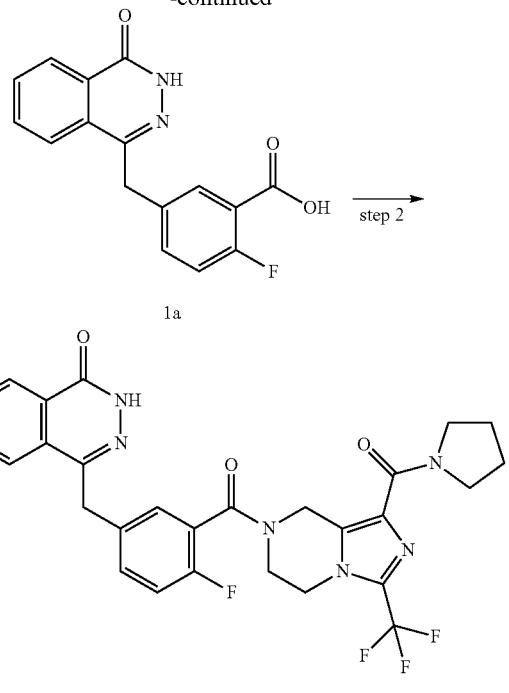

Step 1 pyrrolidin-1-yl-[3-(trifluoromethyl)-5,6,7,8-tetrahydroimidazo[1,5-a]pyrazin-1-yl]methanone Pyrrolidine (560 mg, 8 mmol), methyl 3-(trifluoromethyl)-5,6,7,8-tetrahydroimidazo[1,5-a]pyrazine-1-carboxylate 3b (400 mg, 1.60 mmol) and 0.4 mL of H$_2$O were mixed in a sealed tube. After stirring at 50° C. for 4 hours, the reaction mixture was concentrated under reduced pressure to obtain crude pyrrolidin-1-yl-[3-(trifluoromethyl)-5,6,7,8-tetrahydroimidazo[1,5-a]pyrazin-1-yl]methanone 18a (460 mg) as a light yellow solid. The product was used directly in the next reaction without purification.

MS m/z (ESI): 289.1 [M+1]

Step 2

4-[[4-fluoro-3-[1-(pyrrolidine-1-carbonyl)-3-(trifluoromethyl)-6,8-dihydro-5H-imidazo[1,5-a]pyrazine-7-carbonyl]phenyl]methyl]-2H-phthalazin-1-one 2-Fluoro-5-[(4-oxo-3H-phthalazin-1-yl)methyl]benzoic acid 1a (417 mg, 1.40 mmol) was dissolved in 5 mL of N,N-dimethylformamide, followed by addition of O-(1-N, N,N',N'-tetramethyluronium hexafluorophosphate (1 g, 2.80 mmol), crude pyrrolidin-1-yl-[3-(trifluoromethyl)-5,6,7,8-tetrahydroimidazo[1,5-a]pyrazin-1-yl]methanone 18a (400 mg, 1.40 mmol) and N, N-diisopropylethylamine (0.7 mL, 4.20 mmol). After stirring for 12 hours, the reaction mixture was concentrated under reduced pressure, added with 20 mL of H$_2$O, extracted with ethyl acetate (10 mL×3). The organic phase was combined, washed with saturated sodium chloride solution (10 mL), dried over anhydrous sodium sulfate and filtered. The filtrate was concentrated under reduced pressure and the resulting residue was purified by thin layer chromatography with elution system A to obtain 4-[[4-fluoro-3-[1-(pyrrolidine-1-carbonyl)-3-(trifluoromethyl)-6,8-dihydro-5H-imidazo[1,5-a]pyrazine-7-carbonyl]phenyl]methyl]-2H-phthalazin-1-one 18 (150 mg, yield 18.0%) as a light yellow solid.

MS m/z (ESI): 569.2 [M+1]

$^1$H NMR (400 MHz, DMSO-d$_6$): δ 12.57 (br. s, 1H), 8.26 (d, 1H), 7.83-7.93 (m, 3H), 7.46-7.50 (m, 2H), 7.26-7.31 (m, 1H), 5.07 (s, 1H), 4.84 (s, 1H), 4.27-4.34 (m, 2H), 4.26-4.27 (m, 1H), 4.07-4.17 (m, 2H), 3.89-3.92 (m, 2H), 3.66-3.68 (m, 1H), 3.48-3.49 (m, 1H), 3.36-3.38 (m, 1H), 1.76-1.91 (m, 4H)

Example 19

4-[[4-fluoro-3-[2-(trifluoromethyl)-6,8-dihydro-5H-[1,2,4]triazolo[1,5-a]pyrazine-7-carbonyl]phenyl]methyl]-2H-phthalazin-1-one

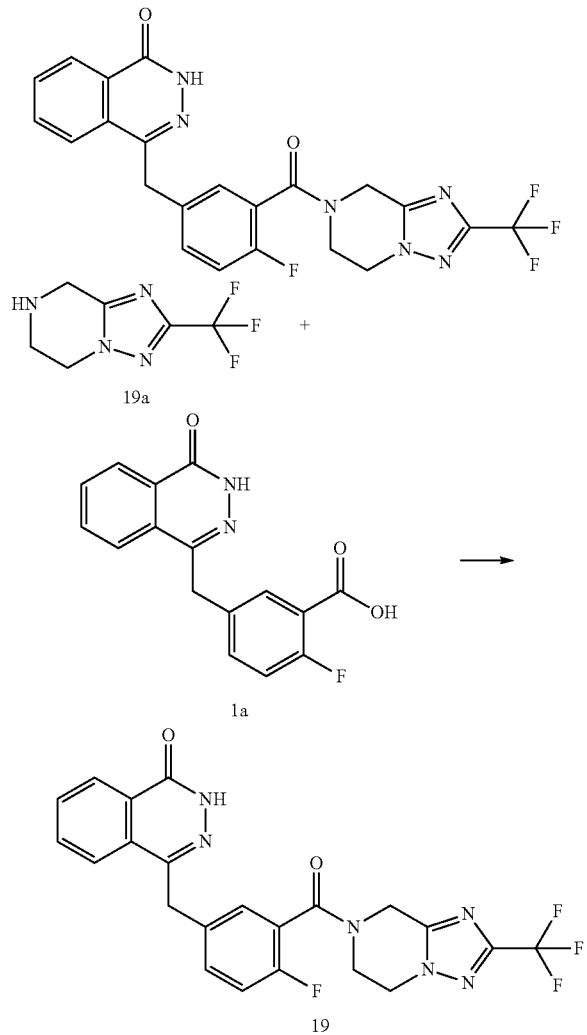

2-Fluoro-5-[(4-oxo-3H-phthalazin-1-yl)methyl]benzoic acid 1a (780 mg, 2.65 mmol) was dissolved in 15 mL of N,N-dimethylformamide, followed by addition of O-(1-benzotriazolyl)-N,N,N',N'-tetramethyluronium hexafluorophosphate (1.80 g, 4.77 mmol), 2-(trifluoromethyl)-5,6,7,8-tetrahydro-[1,2,4]triazolo[1,5-a]pyrazine 19a (560 mg, 2.92 mmol, prepared according to a known method disclosed by "patent application WO2009025784") and N, N-diisopropylethylamine (1.4 mL, 7.95 mmol). After stirring for 12 hours, the reaction mixture was concentrated under reduced pressure, added with 30 mL of H$_2$O, extracted with ethyl acetate (30 mL×3). The organic phase was combined, washed with saturated sodium chloride solution (20 mL), dried over anhydrous sodium sulfate and filtered. The filtrate was concentrated under reduced pressure and the resulting residue was purified by thin layer chromatography with elution system A to obtain 4-[[4-fluoro-3-[2-(trifluoromethyl)-6,8-dihydro-5H-[1,2,4]triazolo[1,5-a]pyrazine-7-carbonyl]phenyl]methyl]-2H-phthalazin-1-one 19 (205 mg, yield 16.4%) as a light yellow solid.

MS m/z (ESI): 473.1 [M+1]

$^1$H NMR (400 MHz, CDCl$_3$): δ 10.67 (br. s, 1H), 8.48 (s, 1H), 7.77 (m, 3H), 7.42 (m, 2H), 7.11 (t, 1H), 5.10 (s, 1H), 4.75 (s, 1H), 4.39 (s, 2H), 4.32 (d, 3H), 3.88 (s, 1H)

Example 20

4-[[4-fluoro-3-[1-(morpholine-4-carbonyl)-3-(trifluoromethyl)-6,8-dihydro-5H-imidazo[1,5-a]pyrazine-7-carbonyl]phenyl]methyl]-2H-phthalazin-1-one

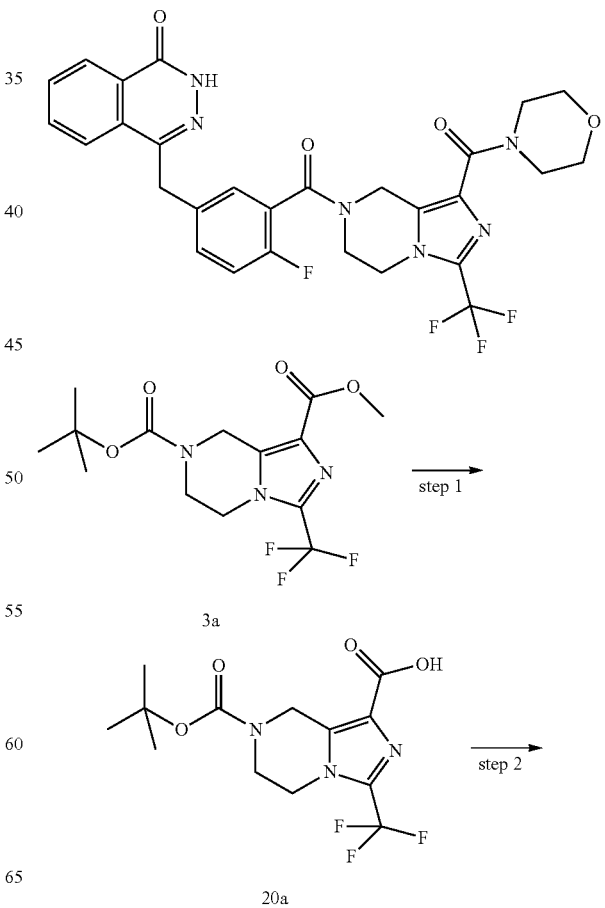

-continued

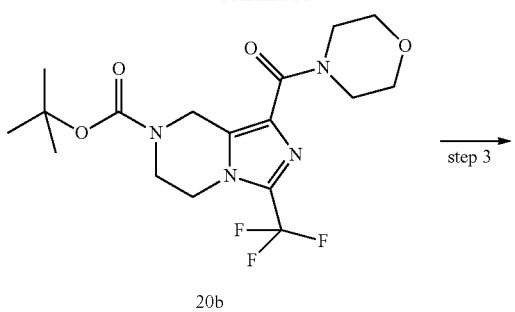

20b

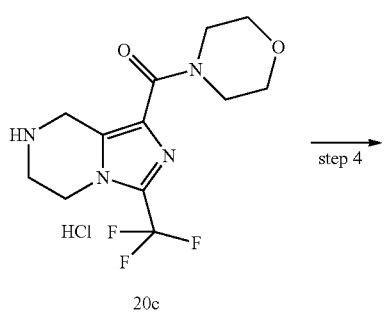

20c

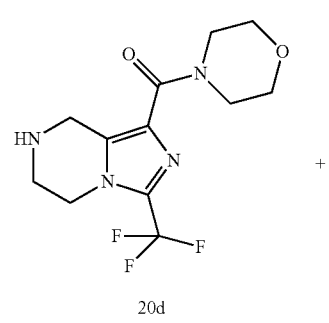

20d

+

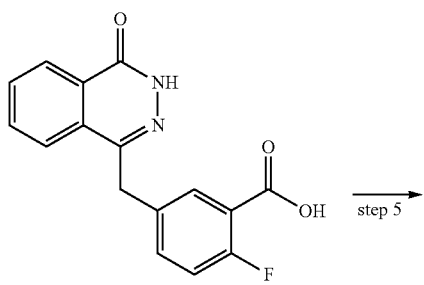

1a

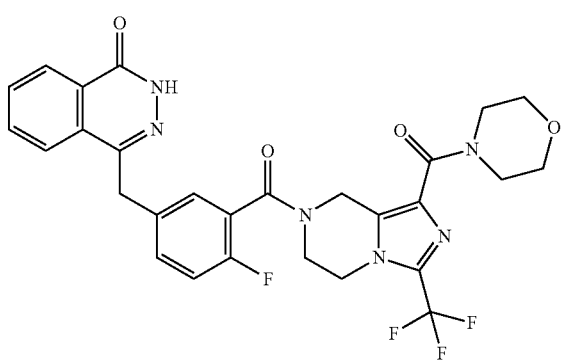

20

Step 1

7-tert-butoxy carbonyl-3-(trifluoromethyl)-6,8-dihydro-5H-imidazo[1,5-a]pyrazine-1-carboxylic acid O-7-tert-butyl-O-1-methyl-3-(trifluoromethyl)-6,8-dihydro-5H-imidazo[1,5-a]pyrazine-1,7-dicarboxylate 3a (4.10 g, 12 mmol) was dissolved in a mixed solvent of 15 mL of tetrahydrofuran and methanol (V/V=2:1), followed by addition of 20 mL of a 2 M sodium hydroxide solution. After stirring for 12 hours, the reaction mixture was concentrated under reduced pressure, and 1 M hydrochloric acid was added dropwise with until the pH of the reaction mixture was between 5 and 7. The reaction mixture was filtered and the filter cake was dried in vacuum to obtain 7-tert-butoxy-carbonyl-3-(trifluoromethyl)-6,8-dihydro-5H-imidazo[1,5-a]pyrazine-1-carboxylic acid 20a (2 g, yield 50.0%) as a light yellow solid.

MS m/z (ESI): 334.1 [M+1]

Step 2 tert-butyl 1-(morpholine-4-carbonyl)-3-(trifluoromethyl)-6,8-dihydro-5H-imidazo[1,5-a]pyrazine-7-carboxylate 7-Tert-butoxycarbonyl-3-(trifluoromethyl)-6,8-dihydro-5H-imidazo[1,5-a]pyrazine-1-carboxylic acid 20a (330 mg, 1 mmol) was dissolved in 5 mL of N, N-dimethylformamide, followed by addition of O-(1-benzotriazolyl)-N,N,N',N'-tetramethyluronium hexafluorophosphate (756 mg, 2 mmol), morpholine (174 mg, 2 mmol) and N, N-diisopropylethylamine (0.5 mL, 3 mmol). After stirring for 12 hours, the reaction mixture was concentrated under reduced pressure, added with 20 mL of saturated ammonium chloride solution, extracted with dichloromethane (20 mL×3). The organic phase was combined, dried over anhydrous sodium sulfate and filtered. The filtrate was concentrated under reduced pressure and the resulting residue was purified by thin layer chromatography with elution system A to obtain tert-butyl 1-(morpholine-4-carbonyl)-3-(trifluoromethyl)-6,8-dihydro-5H-imidazo[1,5-a]pyrazine-7-carboxylate 20b (400 mg, yield 100.0%) as a yellow solid.

MS m/z (ESI): 405.1 [M−1]

Step 3 morpholino-[3-(trifluoromethyl)-5,6,7,8-tetrahydroimidazo[1,5-a]pyrazin-1-yl]methanone hydrochloride Tert-butyl 1-(morpholine-4-carbonyl)-3-(trifluoromethyl)-6,8-dihydro-5H-imidazo[1,5-a]pyrazine-7-carboxylate 20b (470 mg, 1.27 mmol) was dissolved in 20 mL of a 2 M solution of hydrogen chloride in 1,4-dioxane. After stirring for 12 hours, the reaction mixture was concentrated under reduced pressure to obtain crude morpholino-[3-(trifluoromethyl)-5,6,7,8-tetrahydroimidazo[1,5-a]pyrazin-1-yl]methanone hydrochloride 20c (300 mg) as a light yellow oil. The product was used directly in the next reaction without purification.

Step 4 morpholino-[3-(trifluoromethyl)-5,6,7,8-tetrahydroimidazo[1,5-a]pyrazin-1-yl]methanone Crude morpholino-[3-(trifluoromethyl)-5,6,7,8-tetrahydroimidazo[1,5-a]pyrazin-1-yl]methanone hydrochloride 20c (330 mg, 1 mmol) was dissolved in 10 mL of ethyl acetate, followed by addition of potassium carbonate (10 g, 72 mmol). After stirring for 4 hours, the reaction mixture was filtered and the filtrate was concentrated under reduced pressure to obtain crude morpholino-[3-(trifluoromethyl)-5,6,7,8-tetrahydroimidazo[1,5-a]pyrazin-1-yl]methanone 20d (300 mg) as a light yellow solid. The product was used directly in the next reaction without purification.

Step 5

4-[[4-fluoro-3-[1-(morpholine-4-carbonyl)-3-(trifluoromethyl)-6,8-dihydro-5H-imidazo[1,5-a]pyrazine-7-carbonyl]phenyl]methyl]-2H-phthalazin-1-one 2-Fluoro-5-[(4-oxo-3H-phthalazin-1-yl)methyl]benzoic acid 1a (390 mg, 1.30 mmol) was dissolved in 10 mL of N,N-dimethylformamide, followed by addition of O-(1-benzotriazolyl)-N,N,N',N'-tetramethyluronium hexafluorophosphate (983 mg, 2.60 mmol), crude morpholino-[3-(trifluoromethyl)-5,6,7,8-tetrahydroimidazo[1,5-a]pyrazin-1-yl]methanone 20d (400 mg, 1.30 mmol) and N,N-diisopropylethylamine (0.7 mL, 3.90 mmol). After stirring for 12 hours, the reaction mixture was concentrated under reduced pressure and the resulting residue was purified by thin layer chromatography with elution system A to obtain 4-[[4-fluoro-3-[1-(morpholine-4-carbonyl)-3-(trifluoromethyl)-6,8-dihydro-5H-imidazo[1,5-a]pyrazine-7-carbonyl]phenyl]methyl]-2H-phthalazin-1-one 20 (150 mg, yield 20.0%) as a light yellow solid.

MS m/z (ESI): 585.2 [M+1]

$^1$H NMR (400 MHz, DMSO-d$_6$): δ 12.58 (br. s, 1H), 8.27 (d, 1H), 7.83-7.98 (m, 3H), 7.48-7.50 (m, 2H), 7.27-7.32 (m, 1H), 5.07 (s, 1H), 4.82 (s, 1H), 4.27-4.35 (m, 2H), 4.26-4.27 (m, 1H), 4.07-4.12 (m, 3H), 3.59-3.66 (m, 6H), 3.17-3.18 (m, 2H)

Example 21

N-methyl-7-[3-[(4-oxo-3H-phthalazin-1-yl)methyl]benzoyl]-3-(trifluoromethyl)-6,8-dihydro-5H-imidazo[1,5-a]pyrazine-1-carboxamide

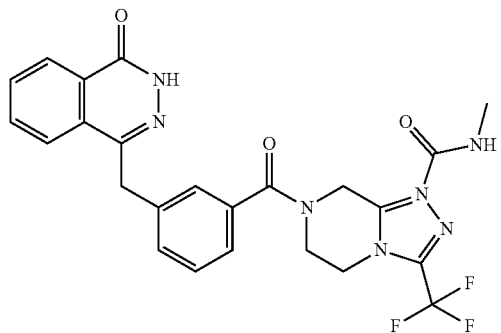

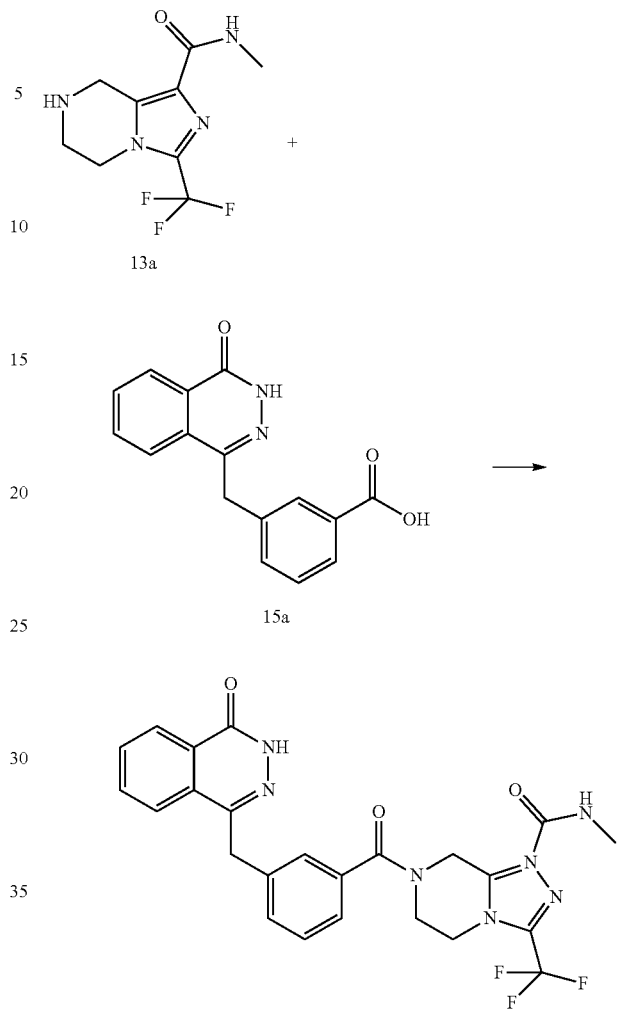

3-[(4-Oxo-3H-phthalazin-1-yl)methyl]benzoic acid 15a (186 mg, 0.67 mmol) was dissolved in 20 mL of N,N-dimethylformamide, followed by addition of 1-hydroxybenzotriazole (98 mg, 0.73 mmol), crude N-methyl-3-(trifluoromethyl)-5,6,7,8-tetrahydroimidazo[1,5-a]pyrazine-1-carboxamide 13a (150 mg, 0.61 mmol), 1-ethyl-(3-dimethylaminopropyl) carbodiimide hydrochloride (173 mg, 0.91 mmol) and triethylamine (253 μL, 1.82 mmol). After stirring for 12 hours, the reaction mixture was was concentrated under reduced pressure, added with 50 mL of H$_2$O and extracted with ethyl acetate (50 mL×3). The organic phase was combined, dried over anhydrous sodium sulfate and filtered. The filtrate was concentrated under reduced pressure and the resulting residue was purified by thin layer chromatography with elution system A to obtain N-methyl-7-[3-[(4-oxo-3H-phthalazin-1-yl)methyl]benzoyl]-3-(trifluoromethyl)-6,8-dihydro-5H-imidazo[1,5-a]pyrazine-1-carboxamide 21 (280 mg, yield 90.0%) as a light yellow solid.

MS m/z (ESI): 511.2 [M+1]

$^1$H NMR (400 MHz, CDCl$_3$): δ 11.80 (br. s, 1H), 8.49 (d, 1H), 7.89 (m, 2H), 7.79 (t, 1H), 7.52 (m, 2H), 7.43 (m, 2H), 5.26 (s, 2H), 4.35 (s, 2H), 4.22 (m, 4H), 3.01 (m, 3H)

Example 22

7-[2-fluoro-5-[(4-oxo-3H-phthalazin-1-yl)methyl]benzoyl]-N,N-dimethyl-3-(trifluoromethyl)-6,8-dihydro-5H-imidazo[1,5-a]pyrazine-1-carboxamide

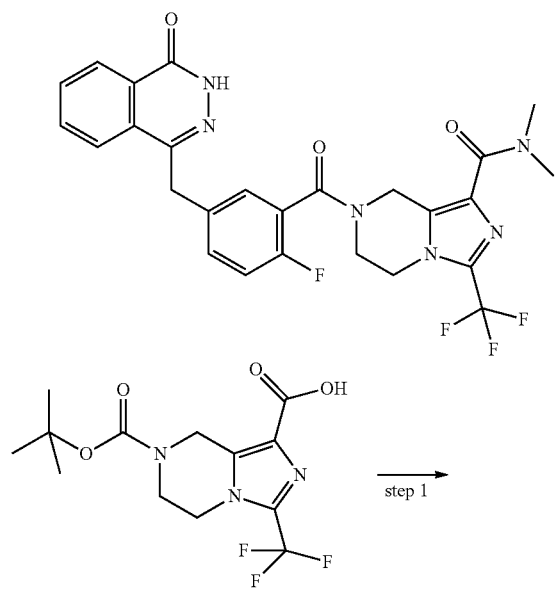

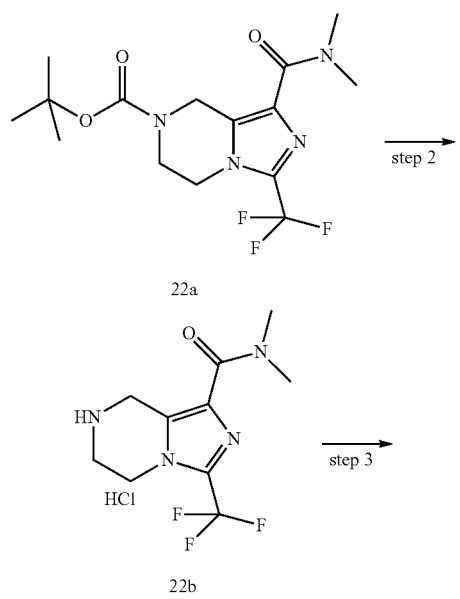

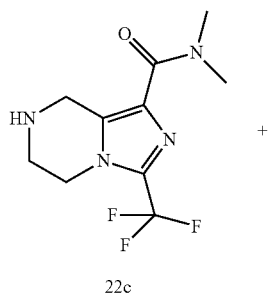

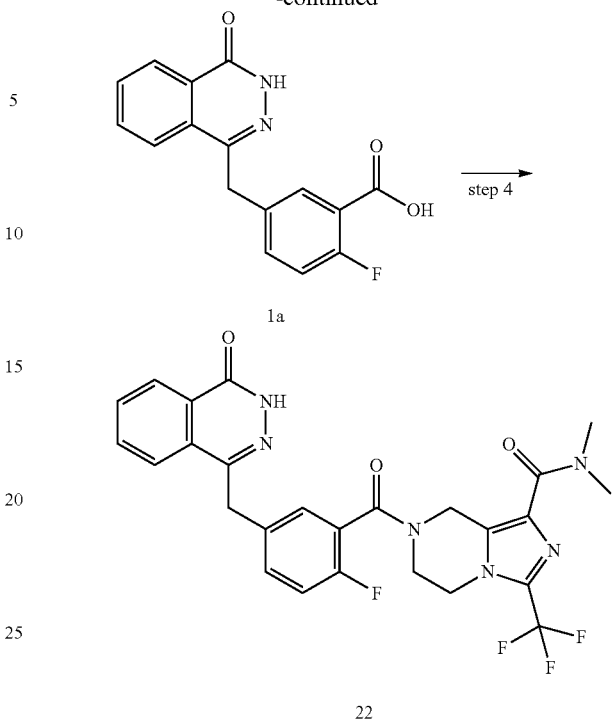

Step 1 tert-butyl 1-(dimethylcarbamoyl)-3-(trifluoromethyl)-6,8-dihydro-5H-imidazo[1,5-a]pyrazine-7-carboxylate 7-Tert-butoxycarbonyl-3-(trifluoromethyl)-6,8-dihydro-5H-imidazo[1,5-a]pyrazine-1-carboxylic acid 20a (330 mg, 1 mmol) was dissolved in 5 mL of N, N-dimethylformamide, followed by addition of 0-(1-benzotriazolyl)-N,N,N',N'-tetramethyluronium hexafluorophosphate (756 mg, 2 mmol), dimethylamine hydrochloride (156 mg, 2 mmol) and N, N-diisopropylethylamine (387 mg, 3 mmol). After stirring for 12 hours, the reaction mixture was concentrated under reduced pressure, added with 50 mL of ethyl acetate, and washed successively with saturated ammonium chloride solution (30 mL) and saturated sodium chloride solution (20 mL×3). The organic phase was combined, dried over anhydrous sodium sulfate and filtered. The filtrate was concentrated under reduced pressure to obtain crude tert-butyl 1-(dimethylcarbamoyl)-3-(trifluoromethyl)-6,8-dihydro-5H-imidazo[1,5-a]pyrazine-7-carboxylate 22a (362 mg) as a light yellow solid. The product was used directly in the next reaction without purification.

MS m/z (ESI): 363.1 [M+1]

Step 2

N,N-dimethyl-3-(trifluoromethyl)-5,6,7,8-tetrahydroimidazo[1,5-a]pyrazine-1-carboxamide hydrochloride Crude tert-butyl 1-(dimethylcarbamoyl)-3-(trifluoromethyl)-6,8-dihydro-5H-imidazo[1,5-a]pyrazine-7-carboxylate 22a (362 mg, 1 mmol) was dissolved in 3 mL of a 2 M solution of hydrogen chloride in 1,4-dioxane. After stirring for 12 hours, the reaction mixture was concentrated under reduced pressure to obtain crude N,N-dimethyl-3-(trifluoromethyl)-5,6,7,8-tetrahydroimidazo[1,5-a]pyrazine-1-carboxamide hydrochloride 22b (262 mg) as a light yellow solid. The product was used directly in the next reaction without purification.

Step 3

N,N-dimethyl-3-(trifluoromethyl)-5,6,7,8-tetrahydroimidazo[1,5-a]pyrazine-1-carboxamide N,N-dimethyl-3-(trifluoromethyl)-5,6,7,8-tetrahydroimidazo[1,5-a]pyrazine-1-carboxamide hydrochloride 22b (234 mg, 0.80 mmol) was dissolved in 10 mL of ethyl acetate, followed by addition of potassium carbonate (10 g, 72 mmol). After stirring for 4 hours, the reaction mixture was filtered and the filtrate was concentrated under reduced pressure to obtain crude N,N-dimethyl-3-(trifluoromethyl)-5,6,7,8-tetrahydroimidazo[1,5-a]pyrazine-1-carboxamide 22c (200 mg) as a light yellow solid. The product was used directly in the next reaction without purification.

Step 4

7-[2-fluoro-5-[(4-oxo-3H-phthalazin-1-yl)methyl]benzoyl]-N,N-dimethyl-3-(trifluoromethyl)-6,8-dihydro-5H-imidazo[1,5-a]pyrazine-1-carboxamide 2-Fluoro-5-[(4-oxo-3H-phthalazin-1-yl)methyl]benzoic acid 1a (300 mg, 1 mmol) was dissolved in 5 mL of N,N-dimethylformamide, followed by addition of O-(1-benzotriazolyl)-N,N,N',N'-tetramethyluronium hexafluorophosphate (756 mg, 2 mmol), N,N-dimethyl-3-(trifluoromethyl)-5,6,7,8-tetrahydroimidazo[1,5-a]pyrazine-1-carboxamide 22c (200 mg, 0.80 mmol) and N,N-diisopropylethylamine (0.5 mL, 3 mmol). After stirring for 12 hours, the reaction mixture was concentrated under reduced pressure and the resulting residue was purified by thin layer chromatography with elution system A to obtain 7-[2-fluoro-5-[(4-oxo-3H-phthalazin-1-yl)methyl]benzoyl]-N,N-dimethyl-3-(trifluoromethyl)-6,8-dihydro-5H-imidazo[1,5-a]pyrazine-1-carboxamide 22 (45 mg, yield 11.0%) as a light yellow solid.

MS m/z (ESI): 543.1 [M+1]

$^1$H NMR (400 MHz, DMSO-$d_6$): δ 12.58 (br. s, 1H), 8.27 (d, 1H), 7.83-7.96 (m, 3H), 7.49-7.51 (m, 2H), 7.27-7.31 (m, 1H), 4.80 (s, 1H), 4.35 (s, 2H), 4.26-4.27 (m, 1H), 4.05-4.07 (m, 1H), 3.66-3.67 (m, 1H), 3.30-3.39 (m, 6H), 2.88-2.97 (m, 2H)

Example 23

4-[[3-[3-(difluoromethyl)-6,8-dihydro-5H-[1,2,4]triazolo[4,3-a]pyrazine-7-carbonyl]-4-fluoro-phenyl]methyl]-2H-phthalazin-1-one

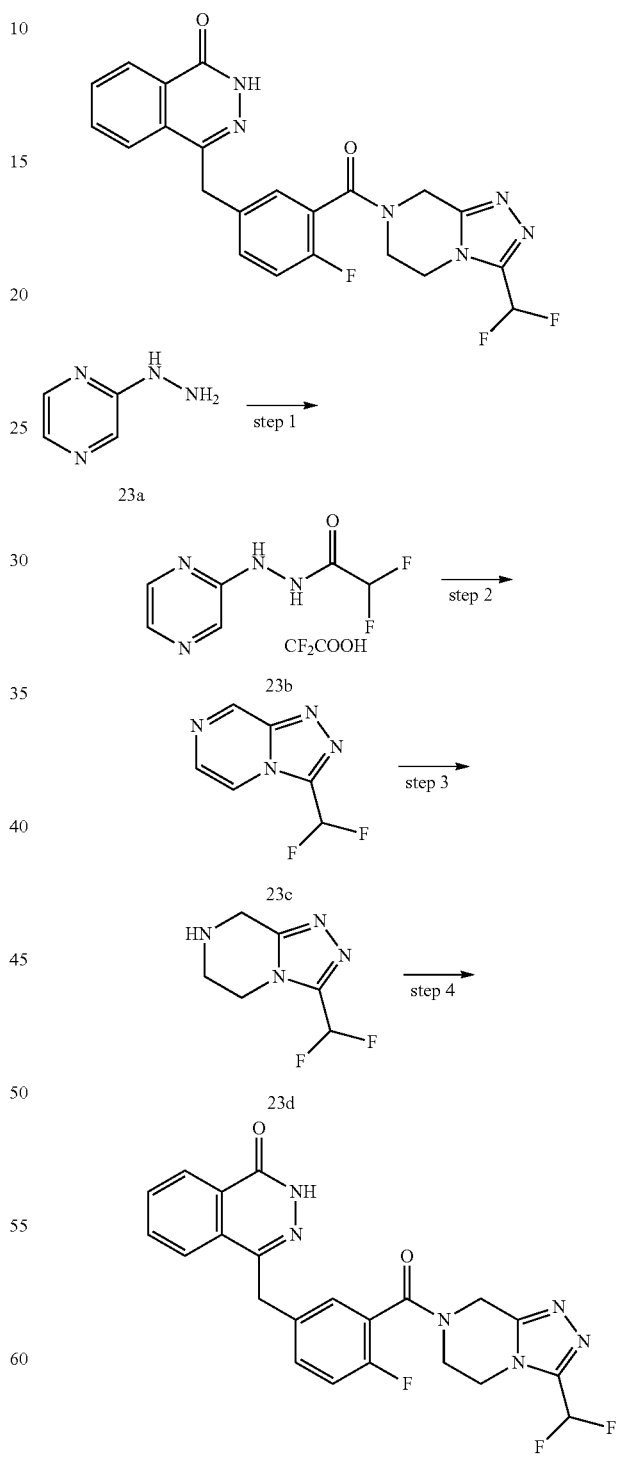

Step 1

2,2-difluoro-N'-pyrazin-2-yl-acetohydrazide difluoroacetate

Pyrazin-2-yl-hydrazine 23a (1 g, 9 mmol) was added in an eggplant-shaped bottle (25 mL), followed by dropwise addition of difluoroacetic anhydride (4 g, 22.98 mmol) at 0° C. After stirring at room temperature for 3 hours, the reaction mixture was concentrated under reduced pressure to obtain crude 2,2-difluoro-N'-pyrazin-2-yl-acetohydrazide difluoroacetate 23b (2 g) as a brown oil. The product was used directly in the next reaction without purification.

Step 2

3-(difluoromethyl)-[1,2,4]triazolo[4,3-a]pyrazine 2,2-Difluoro-N'-pyrazin-2-yl-acetohydrazide difluoroacetate 23b (2 g, 0.01 mol) was dissolved in 10 mL of polyphosphoric acid. After stirring at 140° C. for 7 hours, the reaction mixture was cooled to 50° C. and stirred for another 12 hours. The reaction mixture was poured into 50 mL of ice-water while hot, 30% aqueous ammonia was added dropwise until the pH of the reaction mixture was between 7 and 8, and the solution was extracted with ethyl acetate (30 mL×3). The organic phase was combined, dried over anhydrous sodium sulfate and filtered. The filtrate was concentrated under reduced pressure. The resulting residue was dissolved in 30 mL of ethyl acetate and added with activated carbon. After stirring for 30 minutes, the mixture was filtered and the filtrate was concentrated under reduced pressure to obtain 3-(difluoromethyl)-[1,2,4]triazolo[4,3-a]pyrazine 23c (460 mg, yield 30%) as a yellow solid.

MS m/z (ESI): 171 [M+1]

Step 3

3-(difluoromethyl)-5,6,7,8-tetrahydro-[1,2,4]triazolo [4,3-a]pyrazine 3-(Difluoromethyl)-[1,2,4]triazolo[4,3-a]pyrazine 23c (460 mg, 2.70 mmol) was dissolved in 10 mL of methanol, followed by addition of Pd—C (10%, 46 mg), and the reactor was purged with hydrogen for three times. After stirring for 3 hours, the reaction mixture was filtered and the filter cake was washed with methanol (10 mL). The filtrate was concentrated under reduced pressure to obtain crude 3-(difluoromethyl)-5,6,7,8-tetrahydro-[1,2,4]triazolo[4,3-a] pyrazine 23d (400 mg) as a light yellow oil. The product was used directly in the next reaction without purification.

MS m/z (ESI): 175.0 [M+1]

Step 4

4-[[3-[3-(difluoromethyl)-6,8-dihydro-5H-[1,2,4] triazolo[4,3-a]pyrazine-7-carbonyl]-4-fluoro-phenyl] methyl]-2H-phthalazin-1-one 2-Fluoro-5-[(4-oxo-3H-phthalazin-1-yl)methyl]benzoic acid 1a (685 mg, 2.30 mmol) was dissolved in 10 mL of N,N-dimethylformamide, followed by addition of O-(1-benzotriazolyl)-N,N,N',N'-tetramethyluronium hexafluorophosphate (1.10 g, 3.45 mmol), crude 3-(difluoromethyl)-5, 6,7,8-tetrahydro-[1,2,4]triazolo[4,3-a]pyrazine 23d (400 mg, 2.30 mmol) and N, N-diisopropylethylamine (1.2 mL, 6.90 mmol). After stirring for 12 hours, the reaction mixture was concentrated under reduced pressure and the resulting residue was purified by thin layer chromatography with elution system A to obtain 4-[[3-[3-(difluoromethyl)-6,8-dihydro-5H-[1,2,4]triazolo[4,3-a]pyrazine-7-carbonyl]-4-fluoro-phenyl]methyl]-2H-phthalazin-1-one 23 (200 mg, yield 20.0%) as a white solid.

MS m/z (ESI): 454.6 [M+1]

Example 24

N-(cyclopropylmethyl)-7-[2-fluoro-5-[(4-oxo-3H-phthalazin-1-yl)methyl]benzoyl]-3-(trifluoromethyl)-6,8-dihydro-5H-imidazo[1,5-a]pyrazine-1-carboxamide

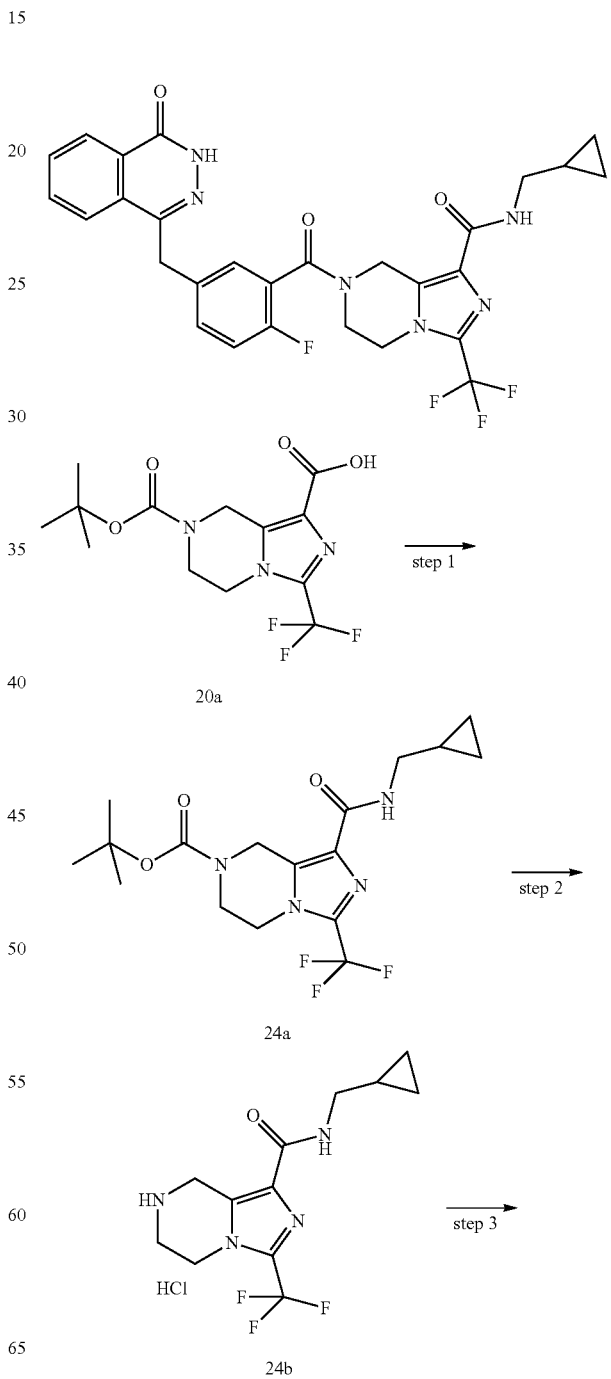

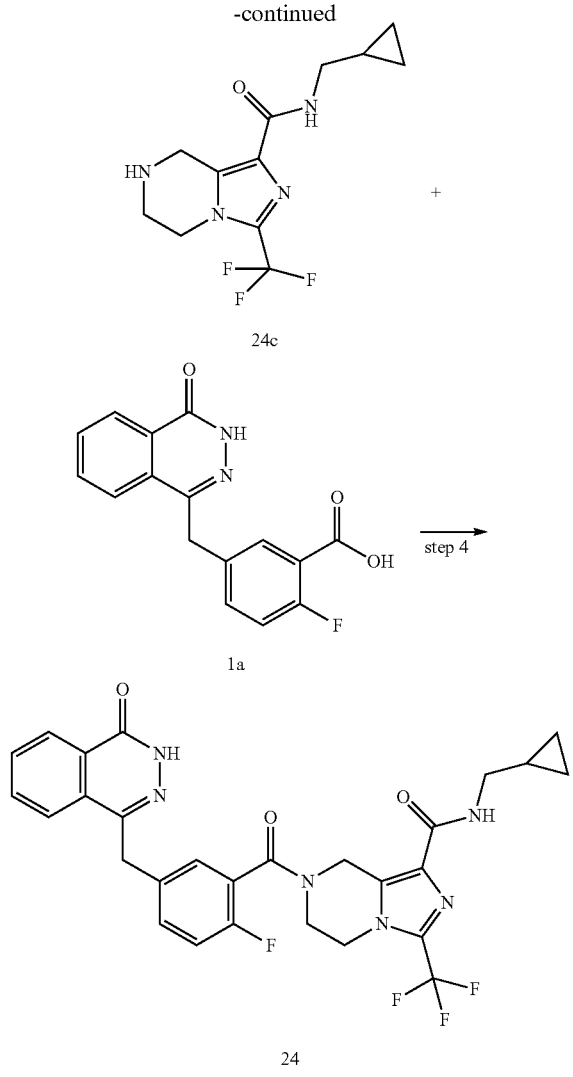

Step 1 tert-butyl 1-(cyclopropylmethylcarbamoyl)-3-(trifluoromethyl)-6,8-dihydro-5H-imidazo[1,5-a]pyrazine-7-carboxylate 7-Tert-butoxycarbonyl-3-(trifluoromethyl)-6,8-dihydro-5H-imidazo[1,5-a]pyrazine-1-carboxylic acid 20a (330 mg, 1 mmol) was dissolved in 5 mL of N, N-dimethylformamide, followed by addition of O-(1-benzotriazolyl)-N,N,N', N'-tetramethyluronium hexafluorophosphate (756 mg, 2 mmol), cyclopropylmethylamine (142 mg, 2 mmol) and N, N-diisopropylethylamine (0.5 mL, 3 mmol). After stirring for 12 hours, the reaction mixture was concentrated under reduced pressure and added with 50 mL of ethyl acetate and washed successively with saturated ammonium chloride (15 mL×3) and saturated sodium chloride solution (10 mL). The organic phase was collected, dried over anhydrous sodium sulfate and filtered. The filtrate was concentrated under reduced pressure to obtain crude tert-butyl 1-(cyclopropylmethylcarbamoyl)-3-(trifluoromethyl)-6,8-dihydro-5H-imidazo[1,5-a]pyrazine-7-carboxylate 24a (300 mg) as a brown-red oil. The product was used directly in the next reaction without purification.

MS m/z (ESI): 389.1 [M+1]

Step 2

N-(cyclopropylmethyl)-3-(trifluoromethyl)-5,6,7,8-tetrahydroimidazo[1,5-a]pyrazine-1-carboxamide hydrochloride Crude tert-butyl 1-(cyclopropylmethylcarbamoyl)-3-(trifluoromethyl)-6,8-dihydro-5H-imidazo[1,5-a]pyrazine-7-carboxylate 24a (300 mg, 0.77 mmol) was dissolved in 20 mL of a 2 M solution of hydrogen chloride in 1,4-dioxane. After stirring for 12 hours, the reaction mixture was concentrated under reduced pressure to obtain crude N-(cyclopropylmethyl)-3-(trifluoromethyl)-5,6,7,8-tetrahydroimidazo[1,5-a]pyrazine-1-carboxamide hydrochloride 24b (250 mg) as a light yellow oil. The product was used directly in the next reaction without purification.

MS m/z (ESI): 289.1 [M+1]

Step 3

N-(cyclopropylmethyl)-3-(trifluoromethyl)-5,6,7,8-tetrahydroimidazo[1,5-a]pyrazine-1-carboxamide N-(cyclopropylmethyl)-3-(trifluoromethyl)-5,6,7,8-tetrahydroimidazo[1,5-a]pyrazine-1-carboxamide hydrochloride 24b (250 mg, 0.77 mmol) was dissolved in 10 mL of dichloromethane, followed by addition of potassium carbonate (320 mg, 2.30 mmol). After stirring for 4 hours, the reaction mixture was filtered and the filtrate was concentrated under reduced pressure to obtain crude N-(cyclopropylmethyl)-3-(trifluoromethyl)-5,6,7,8-tetrahydroimidazo[1,5-a]pyrazine-1-carboxamide 24c (250 mg) as a yellow solid. The product was used directly in the next reaction without purification.

Step 4

N-(cyclopropylmethyl)-7-[2-fluoro-5-[(4-oxo-3H-phthalazin-1-yl)methyl]benzoyl]-3-(trifluoromethyl)-6,8-dihydro-5H-imidazo[1,5-a]pyrazine-1-carboxamide 2-Fluoro-5-[(4-oxo-3H-phthalazin-1-yl)methyl]benzoic acid 1a (300 mg, 1 mmol) was dissolved in 5 mL of N,N-dimethylformamide, followed by addition of O-(1-benzotriazolyl)-N,N,N',N'-tetramethyluronium hexafluorophosphate (756 mg, 2 mmol), crude N-(cyclopropylmethyl)-3-(trifluoromethyl)-5,6,7,8-tetrahydroimidazo[1,5-a]pyrazine-1-carboxamide 24c (250 mg, 0.87 mmol) and N, N-diisopropylethylamine (0.5 mL, 3 mmol). After stirring for 12 hours, the reaction mixture was concentrated under reduced pressure and the resulting residue was purified by thin layer chromatography with elution system A to obtain N-(cyclopropylmethyl)-7-[2-fluoro-5-[(4-oxo-3H-phthalazin-1-yl)methyl]benzoyl]-3-(trifluoromethyl)-6,8-dihydro-5H-imidazo[1,5-a]pyrazine-1-carboxamide 24 (150 mg, yield 30.0%) as a light yellow solid.

MS m/z (ESI): 569.2 [M+1]

Example 25

7-[2-fluoro-5-[(4-oxo-3H-phthalazin-1-yl)methyl]benzoyl]-3-(trifluoromethyl)-6,8-dihydro-5H-imidazo[1,5-a]pyrazine-1-carbonitrile

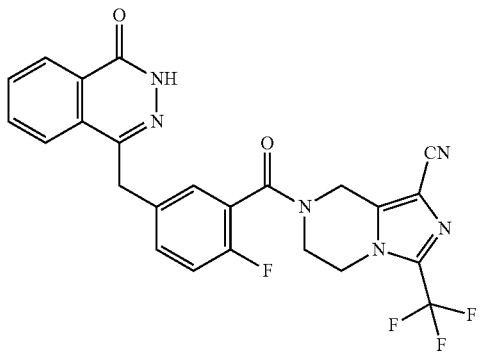

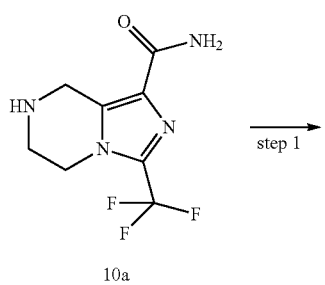
10a

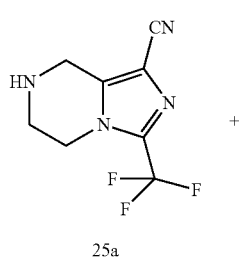
25a
+

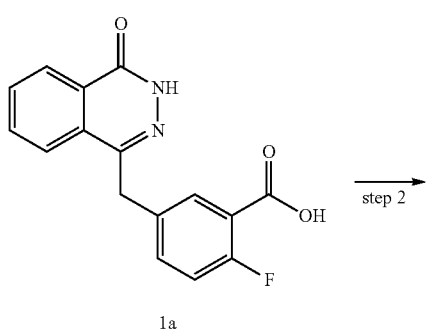
1a

→ step 2

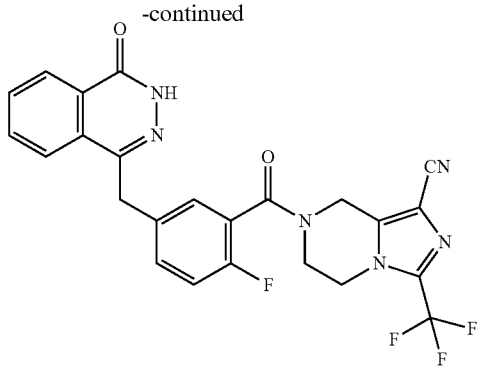
25

Step 1

3-(trifluoromethyl)-5,6,7,8-tetrahydroimidazo[1,5-a]pyrazine-1-carbonitrile 3-(Trifluoromethyl)-5,6,7,8-tetrahydroimidazo[1,5-a]pyrazine-1-carboxamide 10a (100 mg, 0.43 mmol) was dissolved in 5 mL of phosphorus oxychloride. The reaction mixture was heated to reflux for 4 hours. The reaction mixture was concentrated under reduced pressure, added with 10 mL of saturated sodium carbonate solution and extracted with ethyl acetate (25 mL×3). The organic phase was combined, dried over anhydrous sodium sulfate and filtered. The filtrate was concentrated under reduced pressure to obtain crude 3-(trifluoromethyl)-5,6,7,8-tetrahydroimidazo[1,5-a]pyrazine-1-carbonitrile 25a (100 mg) as a brown solid. The product was used directly in the next reaction without purification.

MS m/z (ESI): 217.0 [M+1]

Step 2

7-[2-fluoro-5-[(4-oxo-3H-phthalazin-1-yl)methyl]benzoyl]-3-(trifluoromethyl)-6,8-dihydro-5H-imidazo[1,5-a]pyrazine-1-carbonitrile 2-Fluoro-5-[(4-oxo-3H-phthalazin-1-yl)methyl]benzoic acid 1a (210 mg, 0.70 mmol) was dissolved in 5 mL of N,N-dimethylformamide, followed by addition of O-(1-benzotriazolyl)-N,N,N',N'-tetramethyluronium hexafluorophosphate (350 mg, 0.92 mmol), crude 3-(trifluoromethyl)-5,6,7,8-tetrahydroimidazo[1,5-a]pyrazine-1-carbonitrile 25a (100 mg, 0.46 mmol), and N, N-diisopropylethylamine (250 μL, 1.18 mmol). After stirring for 12 hours, the reaction mixture was concentrated under reduced pressure and the resulting residue was purified by thin layer chromatography with elution system A to obtain 7-[2-fluoro-5-[(4-oxo-3H-phthalazin-1-yl)methyl]benzoyl]-3-(trifluoromethyl)-6,8-dihydro-5H-imidazo[1,5-a]pyrazine-1-carbonitrile 25 (50 mg, yield 21.9%) as a white solid.

MS m/z (ESI): 496.6 [M+1]

Example 26

4-[[4-fluoro-3-[3-(2,2,2-trifluoroethyl)-6,8-dihydro-5H-[1,2,4]triazolo[4,3-a]pyrazine-7-carbonyl]phenyl]methyl]-2H-phthalazin-1-one

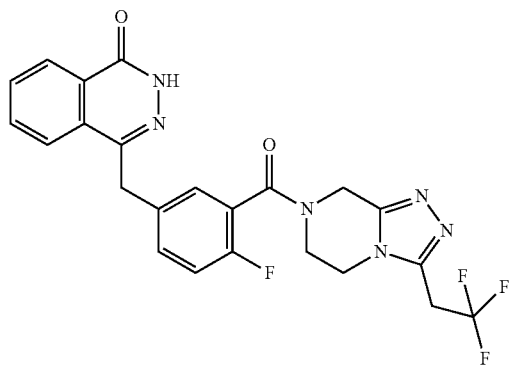

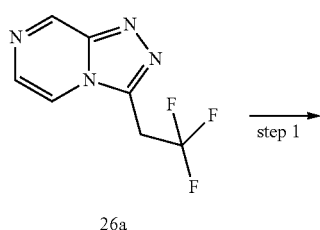

26a

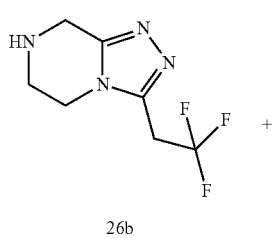

26b

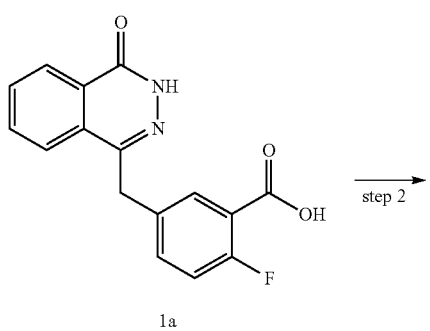

1a

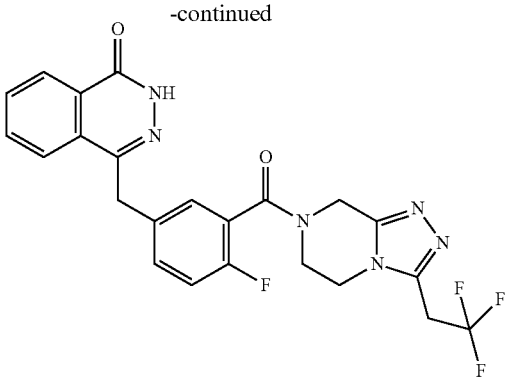

26

Step 1

3-(2,2,2-trifluoroethyl)-5,6,7,8-tetrahydro-[1,2,4]triazolo[4,3-a]pyrazine 3-(2,2,2-trifluoroethyl)-[1,2,4]triazolo[4,3-a]pyrazine 26a (464 mg, 2.29 mmol, prepared according to a known method "Journal of Medicinal Chemistry, 2005, 48(1), 141-151") was dissolved in 20 mL of methanol, followed by addition of Pd—C (10%, 200 mg), and the reactor was purged with hydrogen for three times. After stirring for 3 hours, the reaction mixture was filtered and the filtrate was concentrated under reduced pressure to obtain crude 3-(2,2,2-trifluoroethyl)-5,6,7,8-tetrahydro-[1,2,4]triazolo[4,3-a]pyrazine 26b (480 mg) as a colorless oil. The product was used directly in the next reaction without purification.

Step 2

4-[[4-fluoro-3-[3-(2,2,2-trifluoroethyl)-6,8-dihydro-5H-[1,2,4]triazolo[4,3-a]pyrazine-7-carbonyl]phenyl]methyl]-2H-phthalazin-1-one 2-Fluoro-5-[(4-oxo-3H-phthalazin-1-yl)methyl]benzoic acid 1a (801 mg, 2.69 mmol) was dissolved in 25 mL of N,N-dimethylformamide, followed by addition of O-(1-benzotriazolyl)-N,N,N',N'-tetramethyluronium hexafluorophosphate (1.27 g, 3.36 mmol), crude 3-(2,2,2-trifluoroethyl)-5,6,7,8-tetrahydro-[1,2,4]triazolo[4,3-a]pyrazine 26b (460 mg, 2.24 mmol) and N, N-diisopropylethylamine (0.8 mL, 4.48 mmol). After stirring for 12 hours, the reaction mixture was concentrated under reduced pressure, added with 30 mL of H$_2$O and extracted with ethyl acetate (30 mL×3). The organic phase was combined, concentrated under reduced pressure, added with 30 mL of ethyl acetate, washed with saturated sodium chloride solution (20 mL), dried over anhydrous sodium sulfate and filtered. The filtrate was concentrated under reduced pressure and the resulting residue was purified by thin layer chromatography with elution system A to obtain 4-[[4-fluoro-3-[3-(2,2,2-trifluoroethyl)-6,8-dihydro-5H-[1,2,4]triazolo[4,3-a]pyrazine-7-carbonyl]phenyl]methyl]-2H-phthalazin-1-one 26 (240 mg, yield 22.1%) as a white solid.

MS m/z (ESI): 486.6 [M+1]

Test Examples

Biological Assays

Example 1

Assay for Determining the Enzyme Activity of PARP

The following in vitro screening assay is used to determine the activity of the compounds of the present invention for inhibiting the enzyme activity of PARP.

The assay described below is to determine the activity of the compounds of the present invention for inhibiting the enzyme activity of PARP by using the Trevigen HT F homologous poly (adenosine diphosphate-ribose) polymerase inhibition assay kit (TREVIGEN HT F homogeneous PARP Inhibition Assay Kit, No. 4690-096-K). The assays are based on the $NAD^+$ amount needed to be consumed during the DNA repair process, which is also used in another reaction for catalyzing the substrate without fluorescence activity into molecules with high fluorescence activity. Therefore, the $NAD^+$ level in the reaction system can be learned by measuring the enhancement degree of the fluorescence signal, and then the inhibition degree of the test compound on the enzyme activity of PARP was calculated.

The instructions of TREVIGEN HT F homologous poly (adenosine diphosphate-ribose) polymerase inhibition assay kit can be used as reference for the detailed operation of the assays as well as the preparation of the reagents, such as the reaction mixture (reaction mix), cycling reaction mixture (cycling mix), a buffer solution (buffer), and the like.

The procedures for the assay are summarized as follows: The tested compounds were dissolved in dimethylsulfoxide and then diluted with 1× buffer to the concentration desired in the experiment. 25 μL of a 200 nM $NAD^+$ solution was added to a 96-well round bottomed plate, followed by the addition of 1 μL of tested compounds solution, and the control of replicate wells were installed. Then 25 pt of the reaction mixture containing DNA, PARP enzyme and reaction buffer was added into each well. After incubating for 30 minutes at room temperature, 50 μL of cycling reaction mixture was added into each well and incubated in the dark at room temperature for 15 to 40 minutes. Then 50 pt of stop solution was added into each well and the fluorescence values of each well were read on an ELISA (Ex544 nm, Em590 nm). The inhibition rate of the test compound on the enzyme activity of PARP could be calculated by the standard curve equation of $NAD^+$.

The $IC_{50}$ values of the compounds could be calculated by the inhibition rate at different concentrations.

| Example compounds No. | $IC_{50}$ (PARP-1)/μM |
|---|---|
| 1 | 0.015 |
| 2 | 0.005 |
| 3 | 0.052 |
| 15 | 0.0023 |
| 19 | 0.0102 |

Conclusion: The preferable compounds of the present invention have significant inhibition activity on the proliferation inhibition of PARP-1 kinase.

Example 2

Cell Proliferation Inhibition Assay

The following assay is to determine the activity of the compounds of the present invention for inhibiting the proliferation of triple negative phenotype of breast cancer cell line MDA-MB-436 in vitro.

The in vitro cellular assay described below is to determine the activity of the tested compounds for inhibiting the proliferation of triple negative phenotype of breast cancer cell. The inhibition activity is represented by the $IC_{50}$ value.

The procedures for the assay are summarized as follows: The MDA-MB-436 cells were seeded to a 96-well cell culture plate at a suitable cell concentration (e.g. 3000 cells/ml medium) by using DMEM F12 with 10% FBS (both purchased from Gibco) as complete medium. Under the conditions of 37° C. and 5% carbon dioxide, the cells were cultured in constant temperature incubator and grew overnight. The tested compounds were dissolved in dimethylsulfoxide and then diluted with culture medium without FBS to the concentration desired in the assays. After the cells adhered to the walls, the cell culture medium was replaced by fresh culture medium, in which the tested compounds at serial concentrations (general 7 to 9 concentrations) were contained. Then the cell plates were cultured for continuously for 72 hours under the conditions of 37° C. and 5% carbon dioxide. 72 hours later, the activity of the tested compounds for inhibiting the cell proliferation was determined by using CCK8 (Cell Counting kit-8, No.: CK04, purchased from Dojindo) method.

$IC_{50}$ values of the tested compounds were calculated by the data of inhibition rates of the tested compounds at different concentrations.

| Example compounds No. | $IC_{50}$ (MDA-MB-436)/μM |
|---|---|
| 1 | 0.0008 |
| 3 | 0.19 |
| 5 | 0.32 |
| 7 | 0.071 |
| 10 | 0.14 |
| 12 | 0.59 |
| 13 | 0.12 |
| 15 | 0.0009 |
| 16 | 0.099 |
| 17 | 0.061 |
| 18 | 0.61 |
| 19 | 0.049 |
| 21 | 0.78 |
| 22 | 0.65 |
| 23 | 0.002 |
| 24 | 0.072 |
| 26 | 0.003 |

Conclusion: The preferable compounds of the present invention have significantly inhibition activity on the proliferation inhibition of MDA-MB-436 cell.

Pharmacokinetics Assay

Test Example 1

The Pharmacokinetics Assay of the Compounds of Example 7, Example 13 and Example 19 of the Invention 1. Abstract The compounds of Example 7, Example 13 and Example 19 were administrated intragastrically or by intravenous injection to rats to determine the drug concentration in plasma at different time points by LC/MS/MS method and using SD rats as test animals.

The pharmacokinetic behavior of the compounds of the present invention was studied and evaluated in rats.

analyzed by LC-MS/MS. The main pharmacokinetic parameters were calculated by software DAS 2.0.

4. Results of Pharmacokinetic Parameters

Pharmacokinetic Parameters of the compounds of the present invention were shown as follows:

| Pharmacokinetics Assay (15 mg/kg) | | | | | | | |
|---|---|---|---|---|---|---|---|
| Number | oral bioavailability | | Plasma Conc. Cmax (ng/mL) | Area Under Curve AUC (ng/mL*h) | Half-Life t½(h) | Mean Residence Time MRT(h) | Clearance CL/F (l/h/kg) | Apparent Distribution Volume Vz/F (l/kg) |
| Example 7 | 12.9% | 971 ± 1400 oral gavage | 4495 ± 6671 | 3.87 ± 4.03 | 12.7 ± 15.4 | 15.4 ± 12.4 | 103 ± 134 |
|  |  | intravenous injection | 34820 ± 15454 | 0.94 ± 0.26 | 1.25 ± 0.53 | 0.52 ± 0.29 | 0.64 ± 0.19 |
| Example 13 | 16.8% | 3073 ± 719 oral gavage | 4298 ± 3252 | 6.01 ± 2.27 | 1.87 ± 0.53 | 4.47 ± 3.78 | 49.9 ± 52.9 |
|  |  | intravenous injection | 29414 ± 18543 | 5.05 ± 1.34 | 0.89 ± 0.44 | 0.72 ± 0.45 | 4.70 ± 2.17 |
| Example 19 |  | 2335 ± 1652 oral gavage | 12557 ± 12372 | 9.79 ± 4.82 | 3.50 ± 1.46 | 3.45 ± 3.21 | 7.97 ± 5.38 |

2. Protocol
2.1 Samples
Compounds of Example 7, Example 13 and Example 19
2.2 Test Animals
24 Healthy adult SD rats, male and female in half, were purchased from SINO-BRITSH SIPPR/BK LAB. ANIMAL LTD., CO, Certificate No.: SCXK (Shanghai) 2003-0002.
2.3 Preparation of the Tested Compounds The intragastrical administration group: the right amount of tested compounds were weighed and dissolved in 0.5 mL of DMSO, diluted with physiological saline to 10 mL and prepared to 1.5 mg/mL.

The intravenous injection administration group: the right amount of tested compounds were weighed and added into 0.5% CMC-Na to prepare a 1.5 mg/mL suspension.
2.4 Administration After an overnight fast, 24 healthy adult SD rats, male and female in half, were administered intragastrically at a dose of 15.0 mg/kg and an administration volume of 10 mL/kg.
2.5 Sample Collection The intragastrical administration group: blood samples (0.2 mL) were taken from orbital sinus at pre administration and at 0.25 hour, 0.5 hour, 1.0 hour, 1.5 hours, 2.0 hours, 3.0 hours, 4.0 hours, 6.0 hours, 7.0 hours, 9.0 hours, 12.0 hours and 24.0 hours post administration, stored in heparinized tubes and centrifuged for 20 minutes at 3,500 rpm to separate plasma. The plasma samples were stored at −20° C. The rats were fed at 2 hours after administration.

The intravenous injection administration group: blood samples (0.2 mL) were taken from orbital sinus at pre administration and at 2 minutes, 15 minutes, 0.5 hour, 1.0 hour, 2.0 hours, 3.0 hours, 4.0 hours, 6.0 hours, 8.0 hours, 12.0 hours and 24.0 hours post administration, stored in heparinized tubes and centrifuged for 20 minutes at 3,500 rpm to separate plasma. The plasma samples were stored at −20° C.
3. Operation 20 µL of rat blank plasmas taken at various time points after administration were added with 50 µL of internal standard solution and 140 pt of methanol and mixed for 3 minutes by a vortexer. The mixture was centrifuged for 10 minutes at 13,500 rpm. 20 µL of the supernatant was Conclusion: The example compounds of the present invention had better pharmacokinetic data and significantly improved pharmacokinetic properties.

Antitumor Effect Assay

Test Example 2

The Assay is to Determine the Antitumor Effect of the Compounds of the Present Invention in Mice 1. Purpose The therapeutic effect of the compounds of the present invention administered in combination with temozolomide (TMZ) on transplanted tumors of human colon carcinoma SW620 or human breast cancer cells MX-1 in nude mice was evaluated by using BALB/cA-nude mice as test animals.
2. Test Drug The compounds of Example 1 and Example 19
3. Test Animals BALB/cA-nude mice, SPF, 16-20 g, female( ) were purchased from SINO-BRITSH SIPPR/BK LAB. ANIMAL LTD., CO. Certificate No.: SCXK(Shanghai) 2008-0016.
4. Experimental Procedures
4.1 Nude mice were adapted to the lab environment for three days.
4.2 The right rib of the nude mice was subcutaneously inoculated with colon carcinoma cells SW620. After tumors grew to 339±132 mm³, mice were randomly divided into teams (d0).

Nude mice were subcutaneously inoculated with human breast cancer cells MX-1. After tumors grew to 100 to 200 mm³, mice were randomly divided into teams (d0).
4.3 Dosage and dosage regimens were shown in the table below. The volume of tumors and the weight of the mice were measured and recorded for 2 to 3 times per week.

The volume of tumor (V) was calculated by the follow equation:

$$V = \tfrac{1}{2} \times a \times b^2$$

wherein: a, b represents length and width respectively.

The antitumor rate (%) = $(C-T)/C$ (%)

wherein: T, C represents the tumor volume of the experimental group (tested compounds) and blank control group at the end of the experiment respectively.

5. Dosage, Dosage Regimens and the Results

| Compound | cell | TMZ dosage (mg/kg) | dosage (mg/kg) | Time (day) | antitumor rate (%) |
|---|---|---|---|---|---|
| Example 1 (oral gavage) + TMZ (oral gavage) | colon carcinoma | 50 | 1 | 44 | ++ |
| Example 19 (oral gavage) + TMZ (oral gavage) | colon carcinoma | 50 | 10 | 52 | ++ |
| Example 19 (oral gavage) + TMZ (oral gavage) | breast cancer | 50 | 1 | 8 | +++ |
|  |  | 50 | 3 | 8 | +++ |
|  |  | 50 | 10 | 8 | +++ |

Conlusion: the range of antitumor rate data (%) was shown as follows: "+": 50%~60%; "++": 60%~80%; "+++": 80%~100%. The tested compounds of the present invention administered in combination with temozolomide (TMZ) had significant antitumor rates on colon cancer cell SW620 and human breast carcinoma cell MX-1, which were all higher than 60%.

We claim:

1. A method for inhibiting poly (ADP-ribose) polymerase (PARP) in a subject in need thereof, comprising administering to the subject a pharmaceutical composition comprising one or more pharmaceutically acceptable carriers or excipients, and a therapeutically effective amount of a compound of formula (I) or a pharmaceutically acceptable salt thereof:

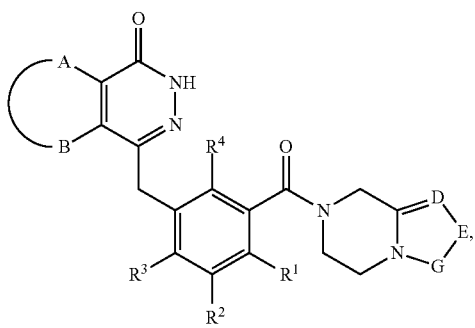

(I)

wherein
A and B are taken together with the attached carbon atoms to form an aryl or heteroaryl, wherein the aryl or heteroaryl is each independently and optionally substituted with one or more groups selected from the group consisting of an alkyl, halogen, hydroxyl, alkoxyl, cycloalkyl, heterocyclyl, aryl, heteroaryl, —C(O)OR$^5$, —OC(O)R$^5$, —O(CH$_2$)$_n$C(O)OR$^5$, —C(O)R$^5$, —NHC(O)R$^5$, —NR$^6$R$^7$, —OC(O)NR$^6$R$^7$ and —C(O)NR$^6$R$^7$;

R$^1$, R$^2$, R$^3$ and R$^4$ are each independently selected from the group consisting of hydrogen, a halogen, alkyl, cyano and alkoxyl, wherein the alkyl or alkoxyl is each independently and optionally substituted with one or more groups selected from the group consisting of a halogen, hydroxyl, alkyl and alkoxyl;

D, E, and G are each independently selected from the group consisting of a nitrogen atom and C(R$^8$);

R$^5$ is selected from the group consisting of hydrogen, alkyl, cycloalkyl, heterocyclyl, aryl and heteroaryl, wherein the alkyl, cycloalkyl, heterocyclyl, aryl or heteroaryl is each independently and optionally substituted with one or more groups selected from the group consisting of an alkyl, halogen, hydroxyl, alkoxyl, cycloalkyl, heterocyclyl, aryl, heteroaryl, carboxyl and alkoxycarbonyl;

R$^6$ and R$^7$ are each independently selected from the group consisting of hydrogen, alkyl, cycloalkyl, heterocyclyl, aryl and heteroaryl, wherein the alkyl, cycloalkyl, heterocyclyl, aryl or heteroaryl is each independently and optionally substituted with one or more groups selected from the group consisting of an alkyl, halogen, hydroxyl, alkoxyl, cycloalkyl, heterocyclyl, aryl, heteroaryl, carboxyl and alkoxycarbonyl;

alternatively, R$^6$ and R$^7$ are taken together with the attached N atom to form a heterocyclyl, wherein the heterocyclyl contains one or more N, O or S(O)$_m$ heteroatoms, and the heterocyclyl is optionally substituted with one or more groups selected from the group consisting of an alkyl, halogen, hydroxyl, alkoxyl, cycloalkyl, heterocyclyl, aryl, heteroaryl, carboxyl and alkoxycarbonyl;

R$^8$ is selected from the group consisting of hydrogen, alkyl, halogen, hydroxyl, cyano, alkoxyl, cycloalkyl, heterocyclyl, aryl, heteroaryl, benzyl, —C(O)R$^5$, —OC(O)R$^5$, —O(CH$_2$)$_n$C(O)OR$^5$, —(CH$_2$)$_n$NR$^6$R$^7$, —C(O)R$^5$, —NHC(O)R$^5$, —NR$^6$R$^7$, —OC(O)NR$^6$R$^7$ and —C(O)NR$^6$R$^7$, wherein the alkyl, alkoxyl, cycloalkyl, heterocyclyl, aryl, heteroaryl or benzyl is each independently and optionally substituted with one or more groups selected from the group consisting of an alkyl, halogen, hydroxyl, alkoxyl, cycloalkyl, heterocyclyl, aryl, heteroaryl, oxo, —C(O)OR$^5$, —OC(O)R$^5$, —O(CH$_2$)$_n$C(O)OR$^5$, —C(O)R$^5$, —NHC(O)R$^5$, —NR$^6$R$^7$, —OC(O)NR$^6$R$^7$ and —C(O)NR$^6$R$^7$;

m is selected from the group consisting of 0, 1 and 2; and
n is selected from the group consisting of 0, 1 and 2.

2. The method according to claim 1, wherein A and B are taken together with the attached carbon atoms to form an aryl.

3. The method according to claim 1, wherein R$^1$ is hydrogen or halogen.

4. The method according to claim 1, wherein G is C(R$^8$) and R$^8$ is trifluoromethyl.

5. The method according to claim 1, wherein the compound of formula (I) is selected from the group consisting of:

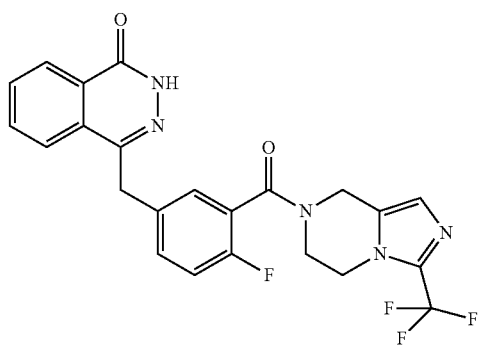

-continued
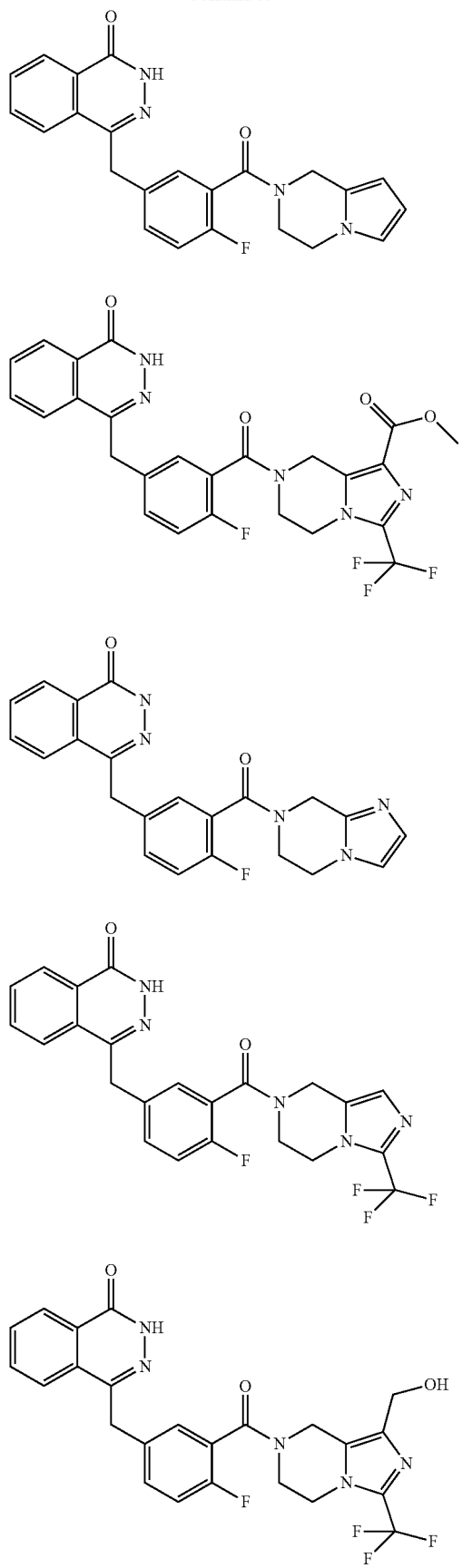
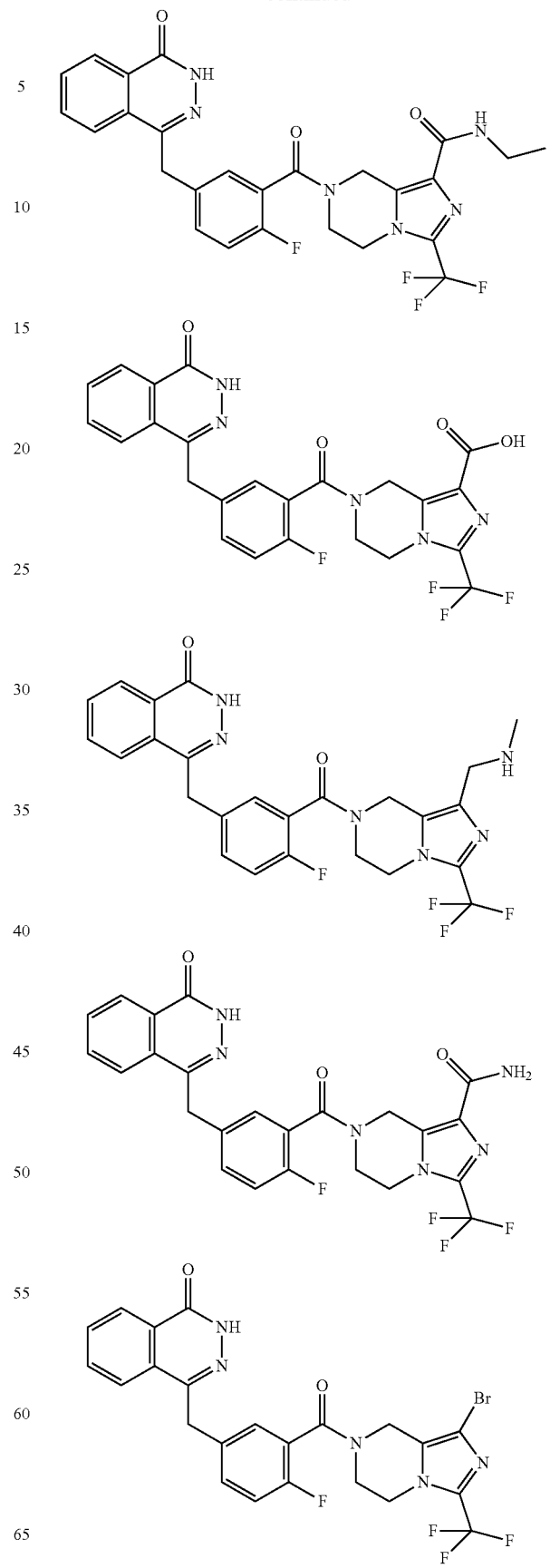

83
-continued
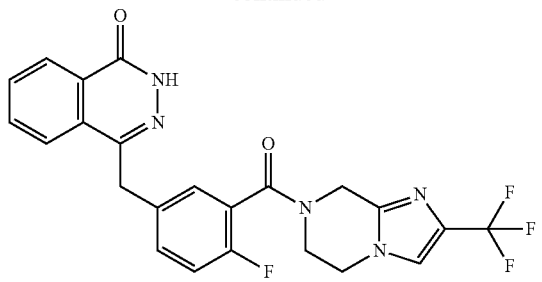
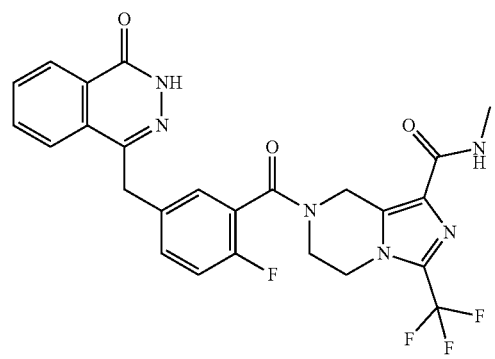 [SMILES: CNC(=O)c1nc(C(F)(F)F)n2c1CN(C(=O)c1cc(Cc3n[nH]c(=O)c4ccccc34)ccc1F)CC2]
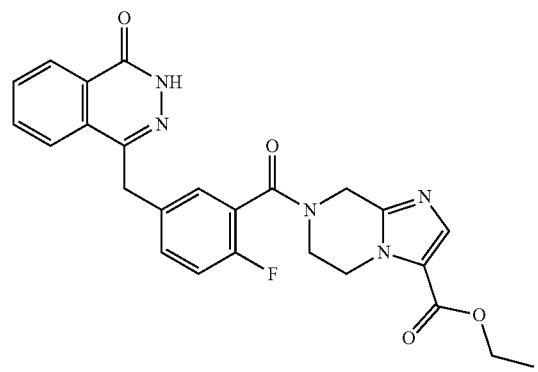
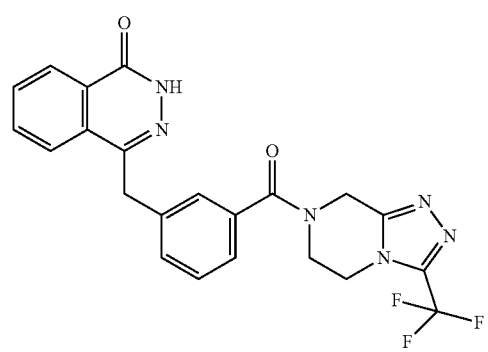 [SMILES: O=C(c1cccc(Cc2n[nH]c(=O)c3ccccc23)c1)N1CCn2c(nnc2C(F)(F)F)C1]
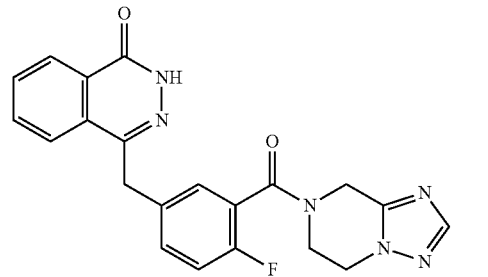 [SMILES: O=C(c1cc(Cc2n[nH]c(=O)c3ccccc23)ccc1F)N1CCn2ncnc2C1]
84
-continued
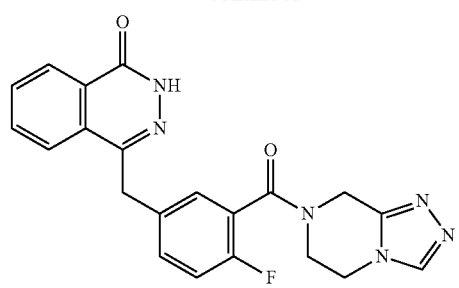 [SMILES: O=C(c1cc(Cc2n[nH]c(=O)c3ccccc23)ccc1F)N1CCn2cnnc2C1]
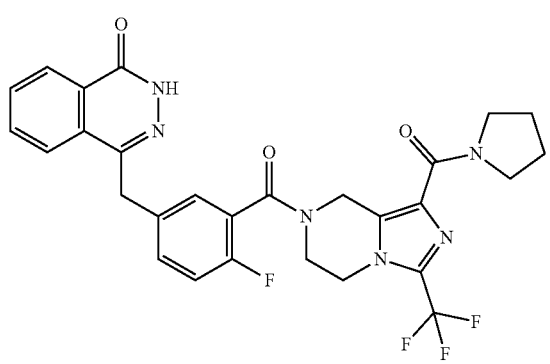
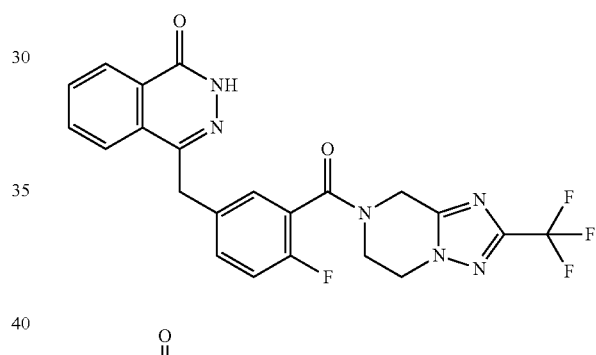
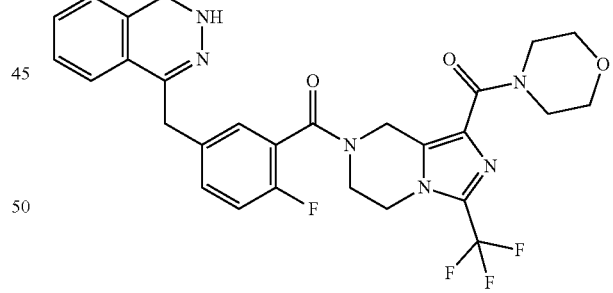
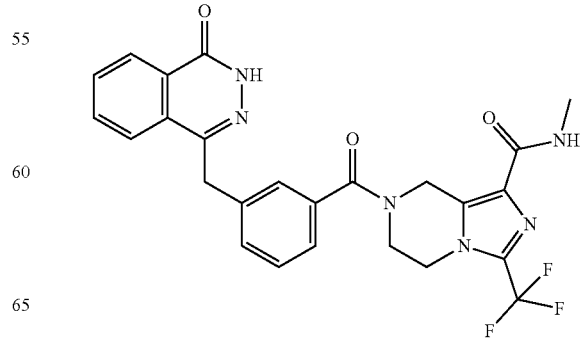

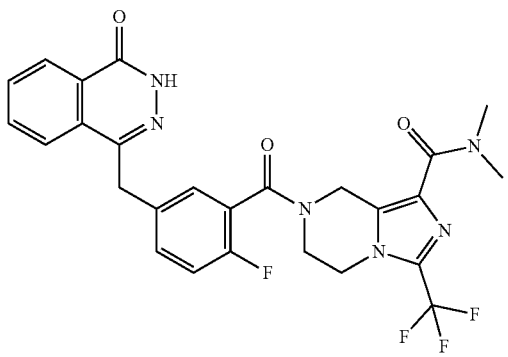 [SMILES: CN(C)C(=O)c1nc(C(F)(F)F)n2c1CN(C(=O)c1cc(Cc3n[nH]c(=O)c4ccccc34)ccc1F)CC2]

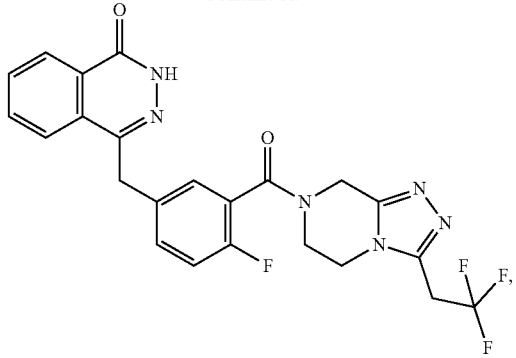

or a pharmaceutically acceptable salt thereof.

6. A method for treating a cancer in a subject in need thereof, wherein the cancer is selected from the group consisting of breast cancer, ovarian cancer, pancreatic cancer, prostate cancer, rectal cancer, and colon cancer, the method comprising administering to the subject a pharmaceutical composition comprising one or more pharmaceutically acceptable carriers or excipients, and a therapeutically effective amount of a compound of formula (I) or a pharmaceutically acceptable salt thereof:

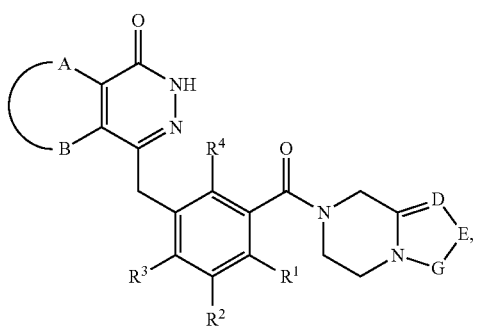

(I)

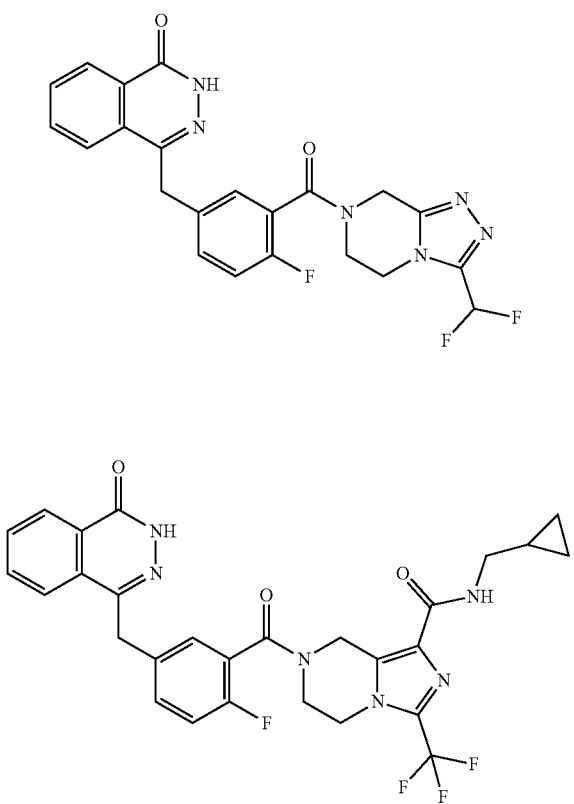

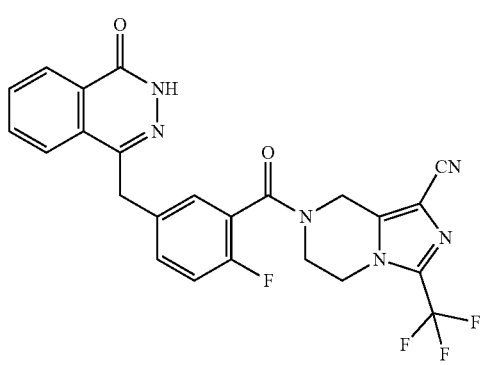 [SMILES: N#Cc1nc(C(F)(F)F)n2c1CN(C(=O)c1cc(Cc3n[nH]c(=O)c4ccccc34)ccc1F)CC2]

and wherein
A and B are taken together with the attached carbon atoms to form an aryl or heteroaryl, wherein the aryl or heteroaryl is each independently and optionally substituted with one or more groups selected from the group consisting of an alkyl, halogen, hydroxyl, alkoxyl, cycloalkyl, heterocyclyl, aryl, heteroaryl, —C(O)OR$^5$, —OC(O)R$^5$, —O(CH$_2$)$_n$C(O)OR$^5$, —C(O)R$^5$, —NHC(O)R$^5$, —NR$^6$R$^7$, —OC(O)NR$^6$R$^7$ and —C(O)NR$^6$R$^7$;
R$^1$, R$^2$, R$^3$ and R$^4$ are each independently selected from the group consisting of hydrogen, a halogen, alkyl, cyano and alkoxyl, wherein the alkyl or alkoxyl is each independently and optionally substituted with one or more groups selected from the group consisting of a halogen, hydroxyl, alkyl and alkoxyl;
D, E, and G are each independently selected from the group consisting of a nitrogen atom and C(R$^8$);
R$^5$ is selected from the group consisting of hydrogen, alkyl, cycloalkyl, heterocyclyl, aryl and heteroaryl, wherein the alkyl, cycloalkyl, heterocyclyl, aryl or heteroaryl is each independently and optionally substituted with one or more groups selected from the group consisting of an alkyl, halogen, hydroxyl, alkoxyl, cycloalkyl, heterocyclyl, aryl, heteroaryl, carboxyl and alkoxycarbonyl;

R⁶ and R⁷ are each independently selected from the group consisting of hydrogen, alkyl, cycloalkyl, heterocyclyl, aryl and heteroaryl, wherein the alkyl, cycloalkyl, heterocyclyl, aryl or heteroaryl is each independently and optionally substituted with one or more groups selected from the group consisting of an alkyl, halogen, hydroxyl, alkoxyl, cycloalkyl, heterocyclyl, aryl, heteroaryl, carboxyl and alkoxycarbonyl;

alternatively, R⁶ and R⁷ are taken together with the attached N atom to form a heterocyclyl, wherein the heterocyclyl contains one or more N, O or S(O)$_m$ heteroatoms, and the heterocyclyl is optionally substituted with one or more groups selected from the group consisting of an alkyl, halogen, hydroxyl, alkoxyl, cycloalkyl, heterocyclyl, aryl, heteroaryl, carboxyl and alkoxycarbonyl;

R⁸ is selected from the group consisting of hydrogen, alkyl, halogen, hydroxyl, cyano, alkoxyl, cycloalkyl, heterocyclyl, aryl, heteroaryl, benzyl, —C(O)OR⁵, —OC(O)R⁵, —O(CH$_2$)$_n$C(O)OR⁵, —(CH$_2$)$_n$NR⁶R⁷, —C(O)R⁵, —NHC(O)R⁵, —NR⁶R⁷, —OC(O)NR⁶R⁷ and —C(O)NR⁶R⁷, wherein the alkyl, alkoxyl, cycloalkyl, heterocyclyl, aryl, heteroaryl or benzyl is each independently and optionally substituted with one or more groups selected from the group consisting of an alkyl, halogen, hydroxyl, alkoxyl, cycloalkyl, heterocyclyl, aryl, heteroaryl, oxo, —C(O)OR⁵, —OC(O)R⁵, —O(CH$_2$)$_n$C(O)OR⁵, —C(O)R⁵, —NHC(O)R⁵, —NR⁶R⁷, —OC(O)NR⁶R⁷ and —C(O)NR⁶R⁷;

m is selected from the group consisting of 0, 1 and 2; and
n is selected from the group consisting of 0, 1 and 2.

7. The method according to claim 6 further comprising administering to the subject a therapeutically effective amount of a drug selected from the group consisting of Temozolomide, Adriamycin, Taxol, Cisplatin, Carboplatin, Dacarbazine, Topotecan, Irinotecan, Gemcitabine and Bevacizumab.

8. The method according to claim 6, wherein the cancer is breast cancer, pancreatic cancer, ovarian cancer, prostate cancer, or colon cancer.

9. The method according to claim 6, wherein A and B are taken together with the attached carbon atoms to form an aryl.

10. The method according to claim 6, wherein R¹ is hydrogen or halogen.

11. The method according to claim 6, wherein G is C(R⁸) and R⁸ is trifluoromethyl.

12. The method according to claim 6, wherein the compound of formula (I) is selected from the group consisting of:

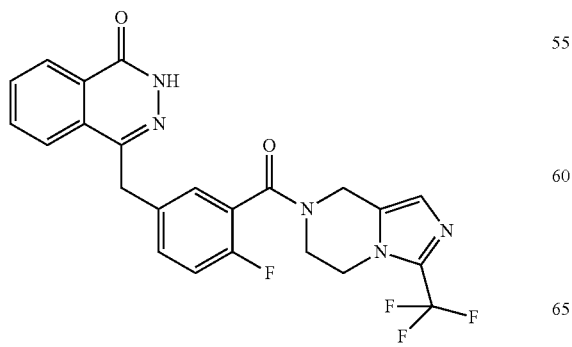

-continued

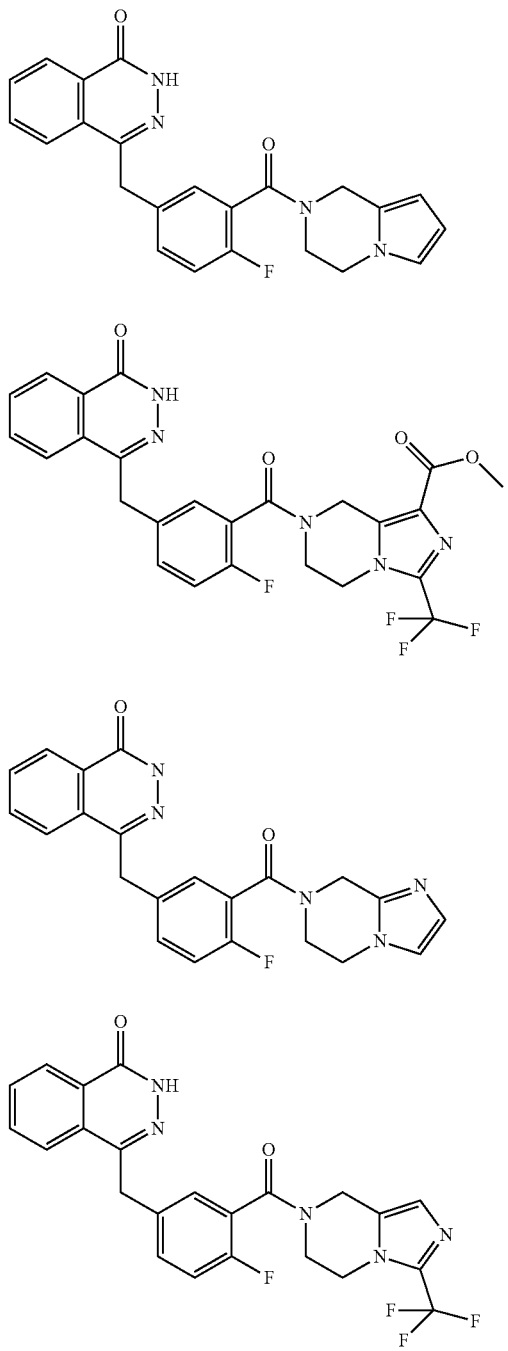

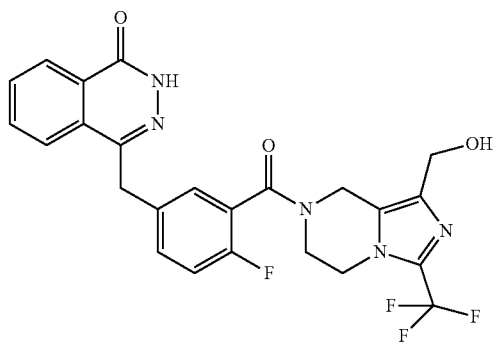

89
-continued
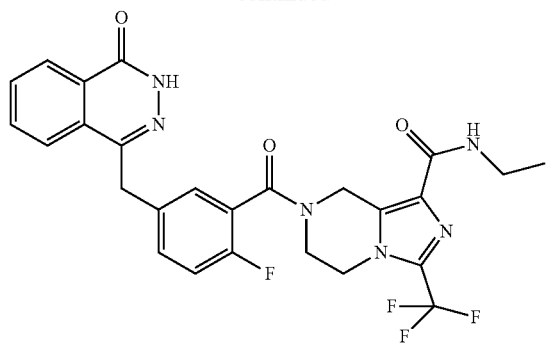
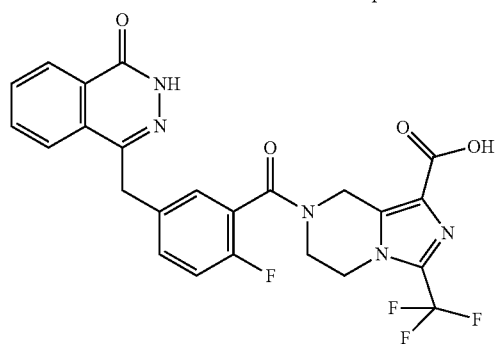
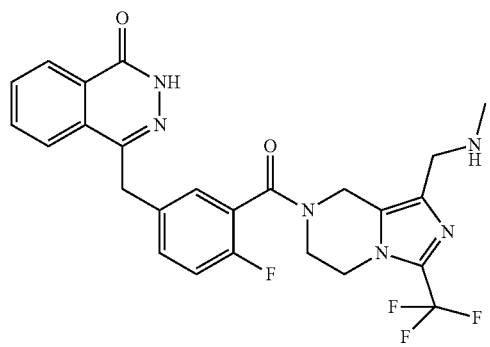
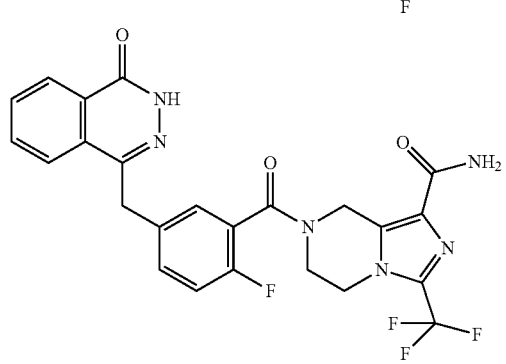
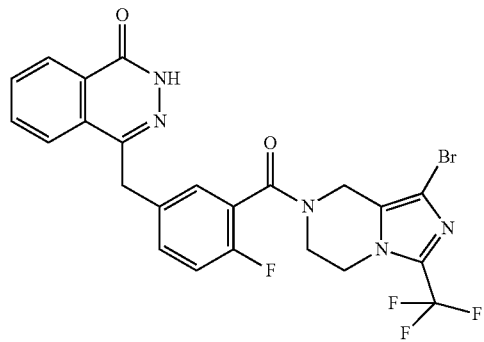
90
-continued
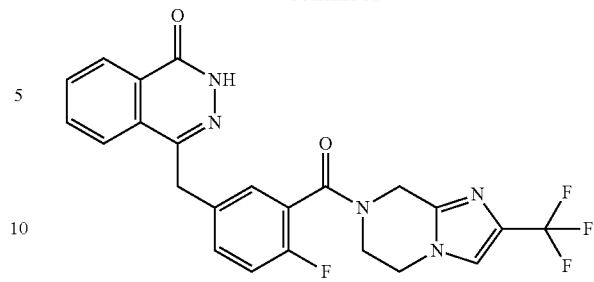
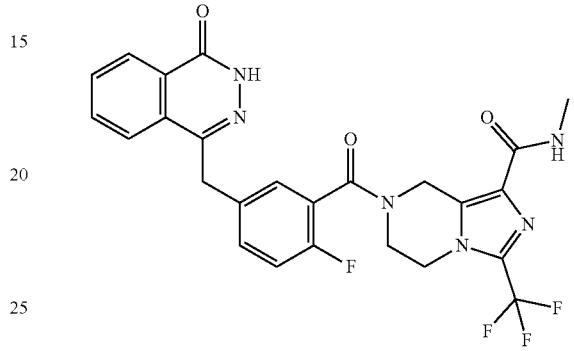
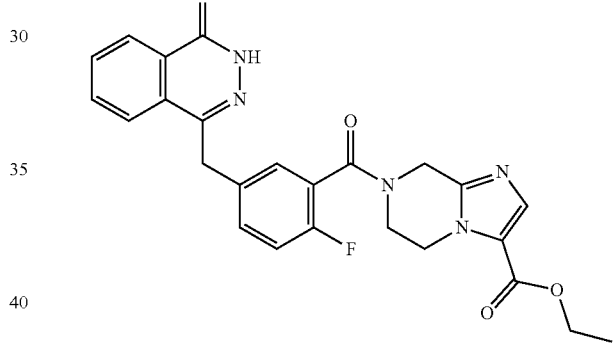
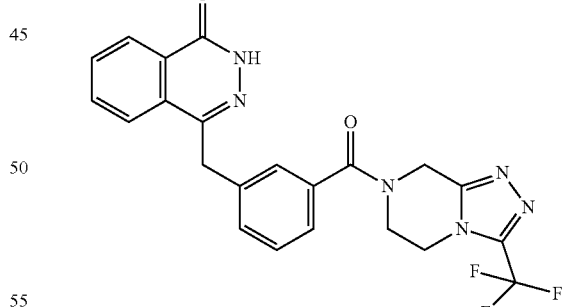
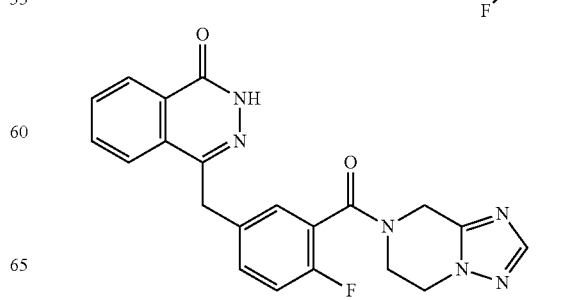

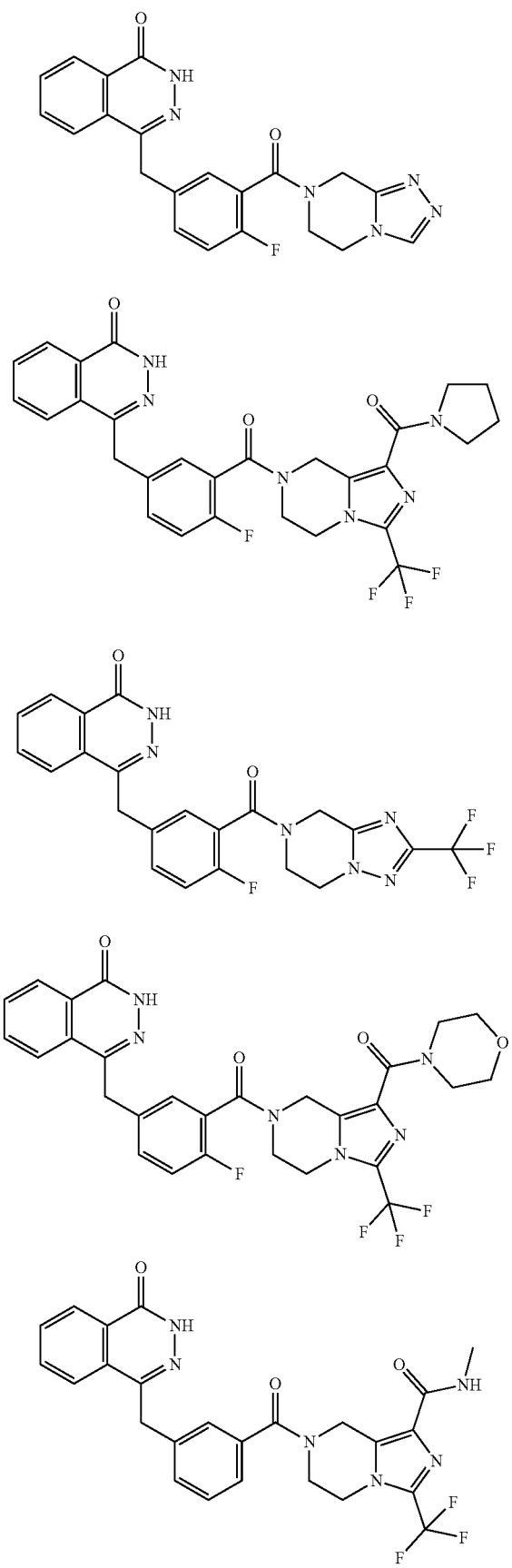
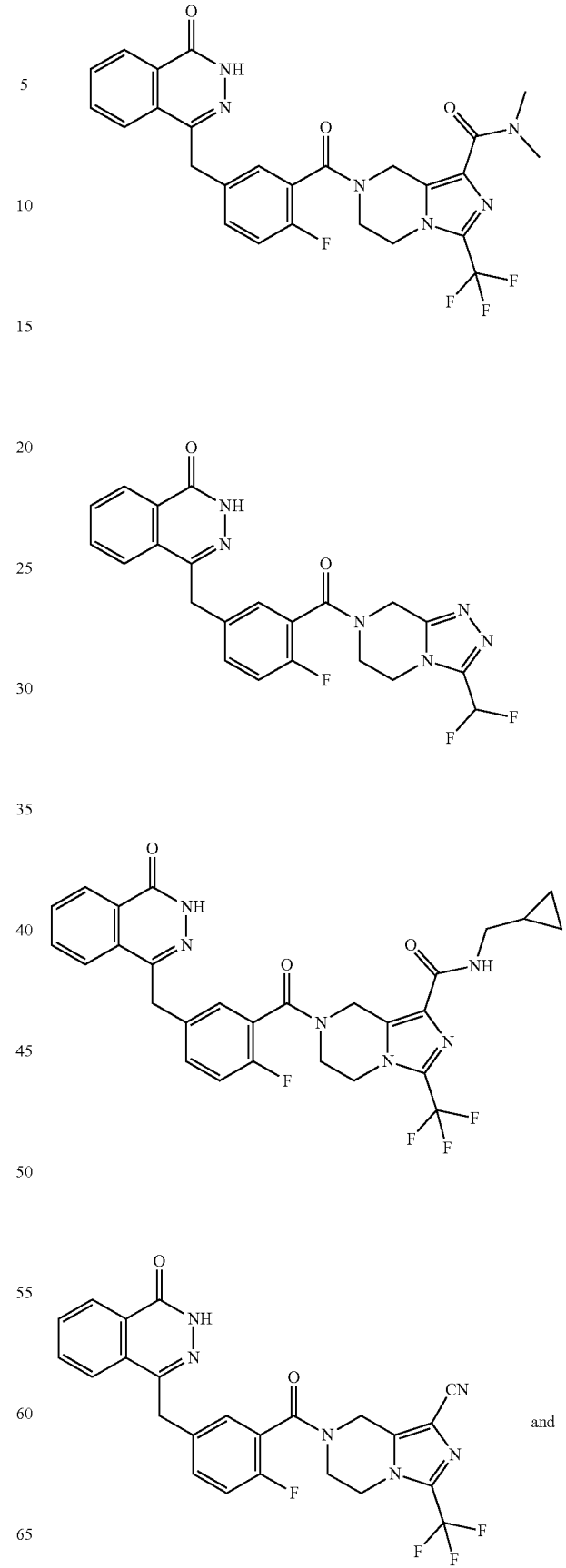

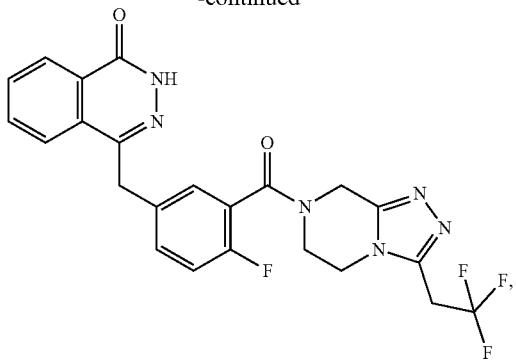

or a pharmaceutically acceptable salt thereof.

13. A method for treating breast cancer or colon cancer in a subject in need thereof, comprising administering to the subject a pharmaceutical composition comprising one or more pharmaceutically acceptable carriers or excipients, and a therapeutically effective amount of a compound of formula (I) or a pharmaceutically acceptable salt thereof:

(I)

wherein
A and B are taken together with the attached carbon atoms to form an aryl or heteroaryl, wherein the aryl or heteroaryl is each independently and optionally substituted with one or more groups selected from the group consisting of an alkyl, halogen, hydroxyl, alkoxyl, cycloalkyl, heterocyclyl, aryl, heteroaryl, —C(O)OR$^5$, —OC(O)R$^5$, —O(CH$_2$)$_n$C(O)OR$^5$, —C(O)R$^5$, —NHC(O)R$^5$, —NR$^6$R$^7$, —OC(O)NR$^6$R$^7$ and —C(O)NR$^6$R$^7$;
R$^1$, R$^2$, R$^3$ and R$^4$ are each independently selected from the group consisting of hydrogen, a halogen, alkyl, cyano and alkoxyl, wherein the alkyl or alkoxyl is each independently and optionally substituted with one or more groups selected from the group consisting of a halogen, hydroxyl, alkyl and alkoxyl;
D, E, and G are each independently selected from the group consisting of a nitrogen atom and C(R$^8$);
R$^5$ is selected from the group consisting of hydrogen, alkyl, cycloalkyl, heterocyclyl, aryl and heteroaryl, wherein the alkyl, cycloalkyl, heterocyclyl, aryl or heteroaryl is each independently and optionally substituted with one or more groups selected from the group consisting of an alkyl, halogen, hydroxyl, alkoxyl, cycloalkyl, heterocyclyl, aryl, heteroaryl, carboxyl and alkoxycarbonyl;
R$^6$ and R$^7$ are each independently selected from the group consisting of hydrogen, alkyl, cycloalkyl, heterocyclyl, aryl and heteroaryl, wherein the alkyl, cycloalkyl, heterocyclyl, aryl or heteroaryl is each independently and optionally substituted with one or more groups selected from the group consisting of an alkyl, halogen, hydroxyl, alkoxyl, cycloalkyl, heterocyclyl, aryl, heteroaryl, carboxyl and alkoxycarbonyl;
alternatively, R$^6$ and R$^7$ are taken together with the attached N atom to form a heterocyclyl, wherein the heterocyclyl contains one or more N, O or S(O)$_m$ heteroatoms, and the heterocyclyl is optionally substituted with one or more groups selected from the group consisting of an alkyl, halogen, hydroxyl, alkoxyl, cycloalkyl, heterocyclyl, aryl, heteroaryl, carboxyl and alkoxycarbonyl;
R$^8$ is selected from the group consisting of hydrogen, alkyl, halogen, hydroxyl, cyano, alkoxyl, cycloalkyl, heterocyclyl, aryl, heteroaryl, benzyl, —C(O)OR$^5$, —OC(O)R$^5$, —O(CH$_2$)—C(O)OR$^5$, —(CH$_2$)$_n$NR$^6$R$^7$, —C(O)R$^5$, —NHC(O)R$^5$, —NR$^6$R$^7$, —OC(O)NR$^6$R$^7$ and —C(O)NR$^6$R$^7$, wherein the alkyl, alkoxyl, cycloalkyl, heterocyclyl, aryl, heteroaryl or benzyl is each independently and optionally substituted with one or more groups selected from the group consisting of an alkyl, halogen, hydroxyl, alkoxyl, cycloalkyl, heterocyclyl, aryl, heteroaryl, oxo, —C(O)OR$^5$, —OC(O)R$^5$, —O(CH$_2$)$_n$C(O)OR$^5$, —C(O)R$^5$, —NHC(O)R$^5$, —NR$^6$R$^7$, —OC(O)NR$^6$R$^7$ and —C(O)NR$^6$R$^7$;
m is selected from the group consisting of 0, 1 and 2; and
n is selected from the group consisting of 0, 1 and 2.

14. The method according to claim 13 further comprising administering to the subject a therapeutically effective amount of a drug selected from the group consisting of Temozolomide, Adriamycin, Taxol, Cisplatin, Carboplatin, Dacarbazine, Topotecan, Irinotecan, Gemcitabine and Bevacizumab.

15. The method according to claim 13, wherein A and B are taken together with the attached carbon atoms to form an aryl.

16. The method according to claim 13, wherein R$^1$ is hydrogen or halogen.

17. The method according to claim 13, wherein G is C(R$^8$) and R$^8$ is trifluoromethyl.

18. The method according to claim 13, wherein the compound of formula (I) is selected from the group consisting of:

95
-continued
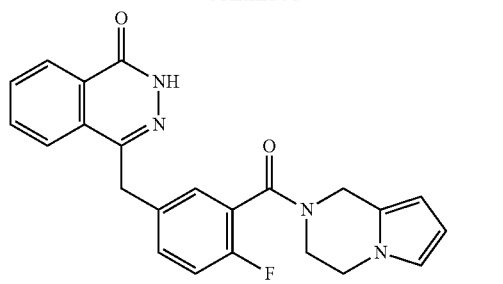
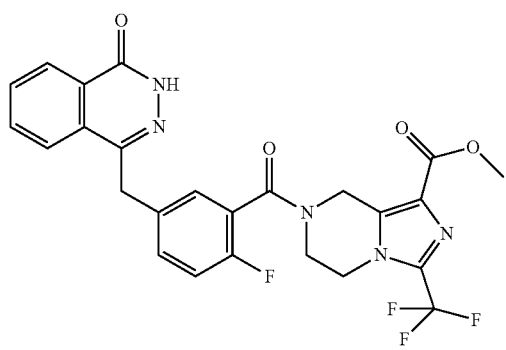
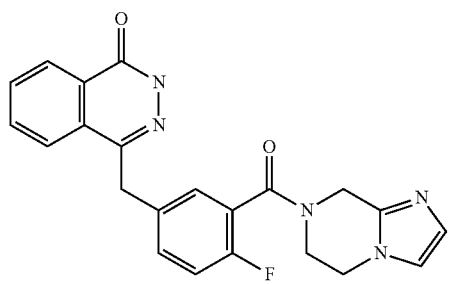
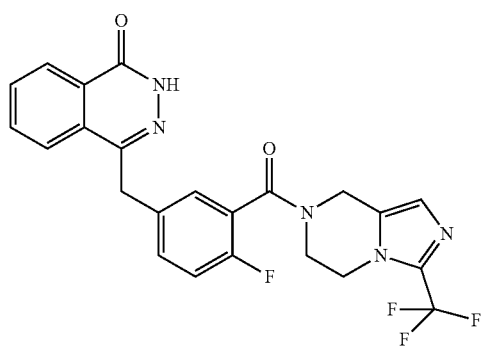
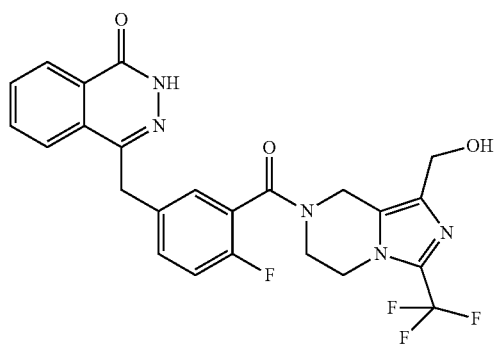
96
-continued
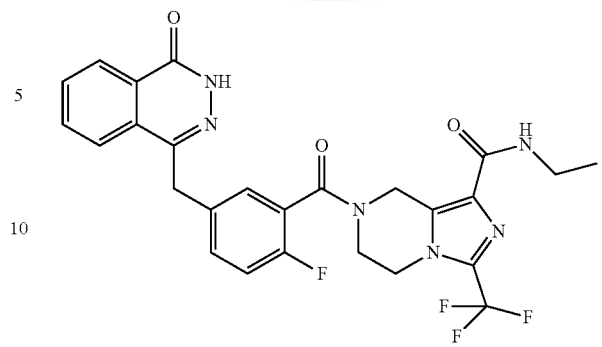
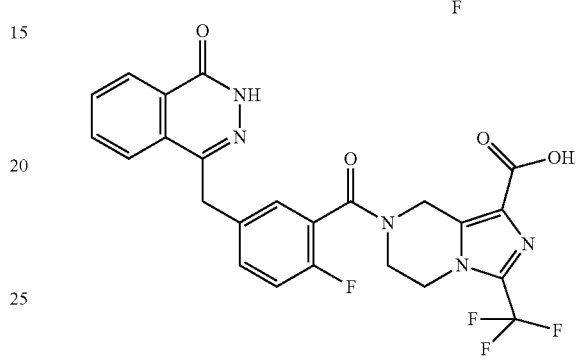
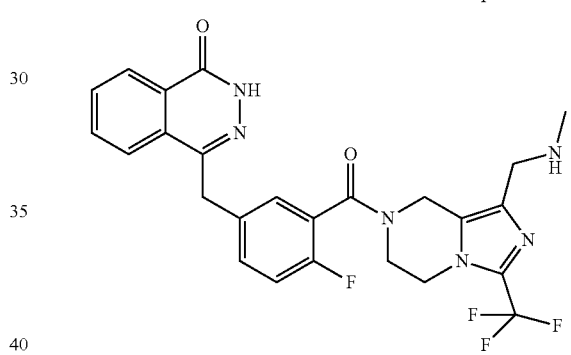
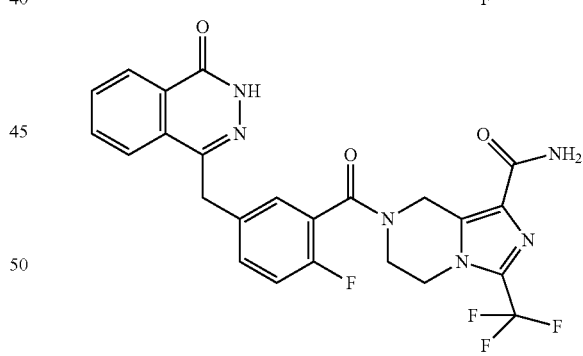
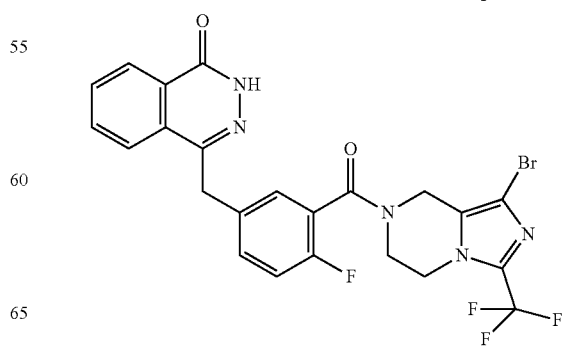

| 97 | 98 |
|---|---|
| -continued | -continued |
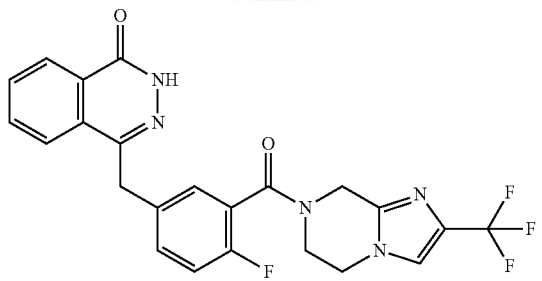
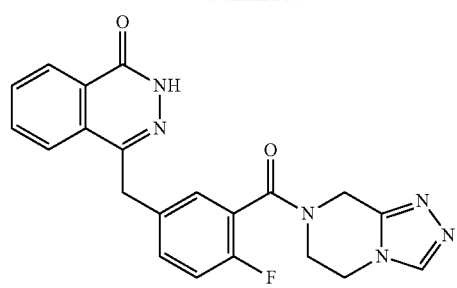
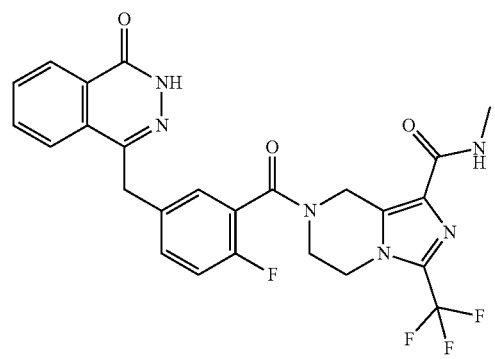
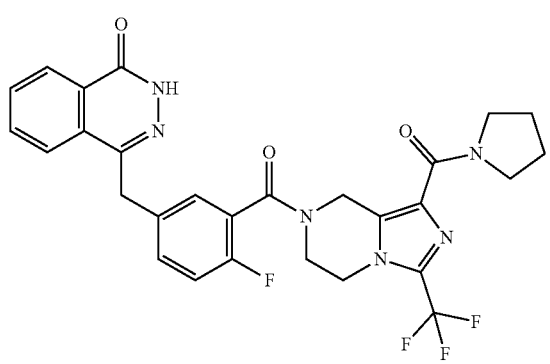
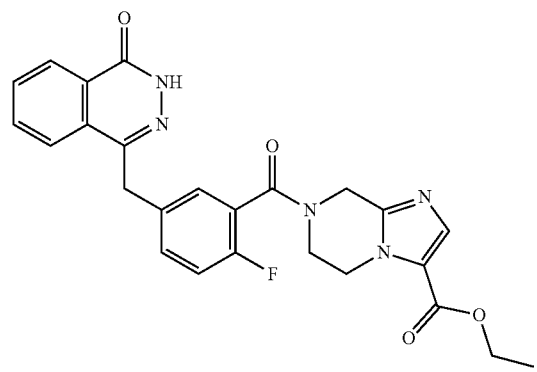
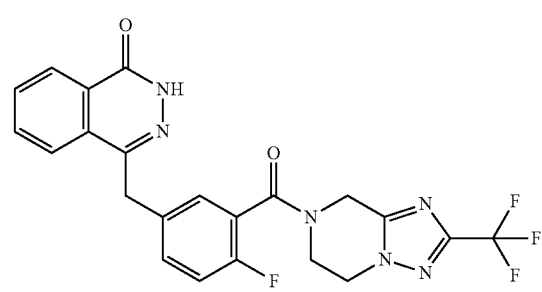
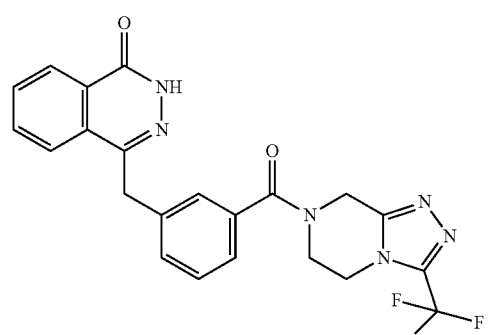
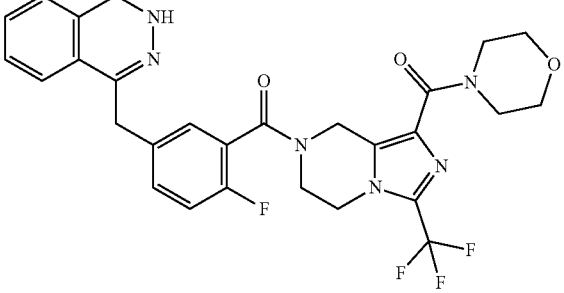
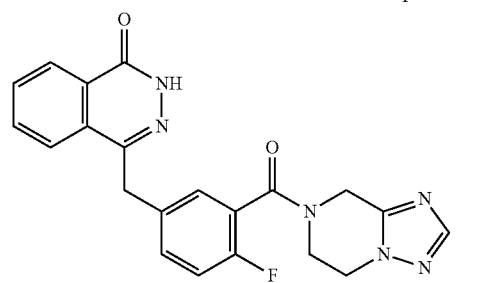
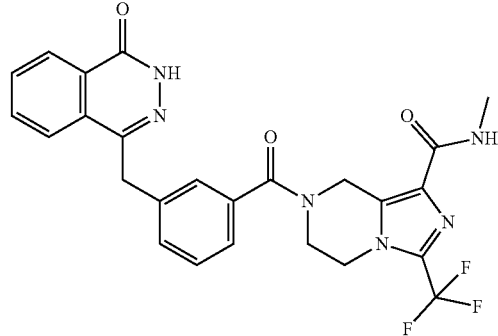

99
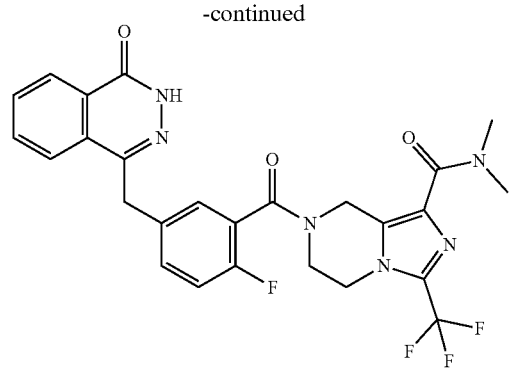
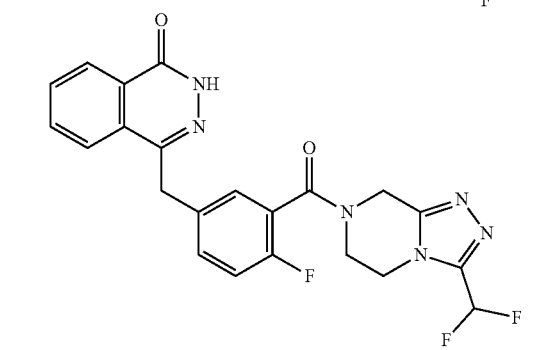
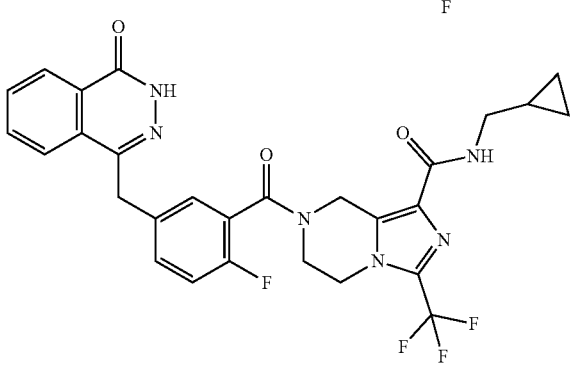
100
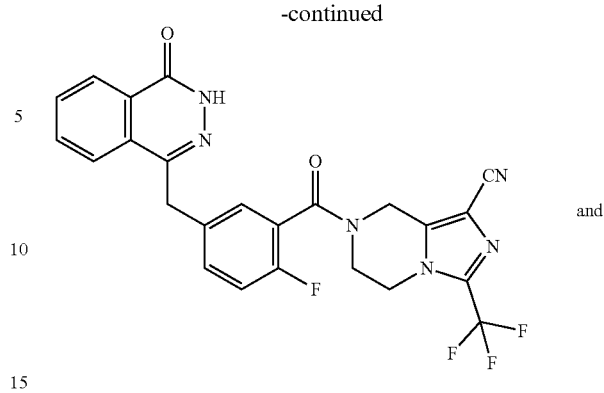
and
or a pharmaceutically acceptable salt thereof.
* * * * *